United States Patent [19]

Mimura et al.

[11] Patent Number: 5,210,266
[45] Date of Patent: May 11, 1993

[54] N-SUBSTITUTED MERCAPTOPROPANAMIDE DERIVATIVES

[75] Inventors: Tetsutaro Mimura, Osaka; Yasuhisa Nakamura, Takatsuki; Junko Nishino, Higashi-Osaka; Tadahiro Sawayama, Kawanishi; Takashi Sasagawa, Ikeda; Takashi Deguchi, Toyonaka; Hideo Nakamura, Tenri, all of Japan

[73] Assignee: Dainippon Pharmaceutical Co., Ltd., Osaka, Japan

[21] Appl. No.: 609,450

[22] Filed: Nov. 5, 1990

Related U.S. Application Data

[60] Continuation-in-part of Ser. No. 503,969, Apr. 4, 1990, abandoned, which is a continuation-in-part of Ser. No. 274,843, Nov. 22, 1988, abandoned, and a continuation-in-part of Ser. No. 504,654, Apr. 4, 1990, Pat. No. 5,179,125, which is a division of Ser. No. 274,843, Nov. 22, 1988, abandoned.

[30] Foreign Application Priority Data

Dec. 3, 1987 [JP] Japan .................. 62-306763
Aug. 10, 1988 [JP] Japan .................. 63-200697

[51] Int. Cl.$^5$ .................. C07C 323/60; C07C 327/32; A61K 31/95
[52] U.S. Cl. .................. 558/254; 544/169; 546/224; 548/557; 541/77; 541/493
[58] Field of Search .................. 558/254; 514/514, 503, 514/969, 274, 843, 504, 654

[56] References Cited

U.S. PATENT DOCUMENTS

| | | | |
|---|---|---|---|
| 4,299,842 | 11/1981 | Cavazza | 558/254 |
| 4,722,810 | 2/1988 | Delaney et al. | 558/254 |

FOREIGN PATENT DOCUMENTS

| | | | |
|---|---|---|---|
| 568628 | 1/1988 | Australia | 558/254 |
| 890948 | 2/1982 | Belgium | 558/254 |
| 0038046 | 10/1981 | European Pat. Off. | 558/254 |
| 0072868 | 2/1982 | European Pat. Off. | 558/254 |
| 0115997 | 8/1984 | European Pat. Off. | 558/254 |
| 0361365 | 4/1990 | European Pat. Off. | 558/254 |
| 2349707 | 4/1974 | Fed. Rep. of Germany | 558/254 |
| 2372624 | 5/1977 | France | 558/254 |
| 2556721 | 12/1983 | France | 558/254 |
| 400670A | 1/1984 | South Africa | 558/254 |

OTHER PUBLICATIONS

B. P. Roques et al., The Enkephalinase Inhibitor Thiorphan Shows Anti-nociceptive Activity in Mice, Nature vol. 288, Nov. 20, 1980, pp. 286–288.

Derwet Abstract to Roussel-UCLAF, Omega Amino Acid Omega Mercaptopropanamide(s), are Enkephalinase Inhibitors, Useful as Analgesics (Dec. 14, 1983).

*Primary Examiner*—Floyd D. Higel
*Attorney, Agent, or Firm*—Birch, Stewart, Kolasch & Birch

[57] ABSTRACT

Novel N-substituted mercaptopropanamide derivatives of the formula:

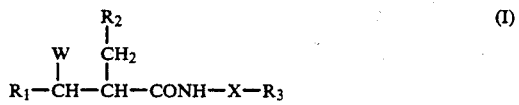

wherein $R_1$ is mercapto or a group convertible into mercapto when cleaved within the biobody, W is hydrogen atom, an alkyl or an aralkyl, $R_2$ is an aryl which may optionally have substituent(s), a heterocyclic group which may optionally have substituent(s), or an alkyl which may optionally have substituent(s), X is a cycloalkylene, a cycloalkylidene, or a phenylene which may optionally have substituent(s) or may optionally be fused with other ring, and $R_3$ is carboxyl or a group convertible into carboxyl when cleaved within the biobody, or a pharmaceutically acceptable salt thereof, and a solid solution of said N-substituted mercaptopropanamide derivative with an amino acid, which have excellent enkephalinase inhibitory activity and are useful for the treatment of mild to moderate pain, and a pharmaceutical composition containing said compounds as an active ingredient, and processes for preparing these compounds.

13 Claims, No Drawings

N-SUBSTITUTED MERCAPTOPROPANAMIDE DERIVATIVES

CROSS-REFERENCE TO RELATED APPLICATION

This is a continuation-in-part application of U.S. Ser. No. 503,969 filed on Apr. 4, 1990, now abandoned which is in turn a continuation-in-part application of U.S. Ser. No. 274,843 filed on Nov. 22, 1988, now abandoned, and of U.S. Ser. No. 504,654 filed on Apr. 4, 1990 now U.S. Pat. No. 5,179,125 which is a divisional application of U.S. Ser. No. 274,843 filed on Nov. 22, 1988 now abandoned.

This invention relates to novel N-substituted mercaptopropanamide derivatives or a salt thereof and a solid solution of the derivative with an amino acid, which are useful as an enkephalinase inhibitor. More particularly, it relates to N-substituted mercaptopropanamide derivatives of the formula:

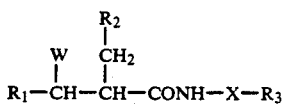

wherein $R_1$ is mercapto or a group convertible into mercapto when cleaved within the biobody, W is hydrogen atom, an alkyl or an aralkyl, $R_2$ is an aryl which may optionally have substituent(s), a heterocyclic group which may optionally have substituent(s), or an alkyl which may optionally have substituent(s), X is a cycloalkylene, a cycloalkylidene, or a phenylene which may optionally have substituent(s) or may optionally be fused with other ring, and $R_3$ is carboxyl or a group convertible into carboxyl when cleaved within the biobody, or a pharmaceutically acceptable salt thereof, and a solid solution of said N-substituted mercaptopropanamide derivative with an amino acid.

PRIOR ART

Enkephalin is an endogenous peptide which binds specifically with morphine receptors and exhibits morphine-like activity and has the following formula:

wherein A is Met or Leu.

Although the physiological meaning thereof is still unclear, it is assumed that it shows control of pain sensation, thermoregulation, regulation of neuroendocrine function and further central action such as effects on feeding or drinking behavior. Enkephalinase decomposes enkephalin by cleaving $Gly^3$-$Phe^4$ bond thereof.

The compounds of this invention inhibit enkephalinase and thereby maintain the activity of enkephalin, by which the compounds show analegesic activity and so on.

It is disclosed in Nature, 288, 286-288 (1980) that thiorphan, i.e. [(D,L)-2-mercaptomethyl-3-phenylpropionyl]glycine shows analgesic activity due to enkephalinase inhibitory activity by cerebroventricular administration or parenteral administration. It is also known that various other mercaptoalkanoylamide derivatives show analgesic activity due to enkaphalinase inhibitory activity (cf. Japanese Patent First Publication (Kokai) Nos. 158746/1981, 148759/1984 and 136554/1985, French Patent Publication No. 2,556,721, South African Patent 8400670, etc.)

The above literatures except Japanese Patent First Publication (Kokai) No. 148759/1984 disclose the compounds of the above formula (I) wherein X is an unsubstituted or substituted alkylene, and Japanese Patent First Publication (Kokai) No. 148759/1984 (=European Patent Publication 0115997 and Australian Patent Publication 568628) discloses the compounds of the formula (I) wherein X is -(benzene)-$CH_2$-. On the other hand, the compounds of this invention are different from these known compounds and are characteristic in the X moiety, that is, they have the formula (I) wherein X is a cycloalkylene, a cycloalkylidene or a phenylene which may optionally have substituent(s) or may optionally be fused with other ring.

SUMMARY DESCRIPTION OF THE INVENTION

An object of the invention is to provide novel N-substituted mercaptopropanamide derivatives or a salt thereof, and a solid solution of the N-substituted mercaptopropanamide derivative with an amino acid, which can show analgesic activity even by oral administration. Another object of the invention is to provide a pharmaceutical composition comprising as an active ingredient the compound as set forth above. A further object of the invention is to provide a method for treating aches by administering the active compound to the patients. A still further object of the invention is to provide a method for preparing the solid solution. These and other objects and advantages of the invention will be apparent to those skilled in the art from the following description.

DETAILED DESCRIPTION OF THE INVENTION

The N-substituted mercaptopropanamide derivatives of the invention have the formula (I) described hereinbefore.

The salts of the N-substituted mercaptopropanamide derivatives include pharmaceutically acceptable salts, for example, salts with alkali metals such as sodium, potassium, etc., salts with alkaline earth metals such as calcium, magnesium, etc., salts with basic amino acids such as lysine, arginine, etc., salts with organic bases such as triethylamine, dicyclohexylamine, etc., and the like.

The "group convertible into mercapto when cleaved within the biobody" includes, for example, $R_4$—CO—S— (wherein $R_4$ is hydrogen atom, an alkyl, a cycloalkyl, a cycloalkyl-alkyl, an alkoxy, or an aryl, aralkyl, heterocyclic group, heterocyclic group-substituted alkyl, or aryloxyalkyl, these ring-containing groups having optionally substitutent(s) on the ring, or an N-($C_1$-$C_4$) alkyl substituted or unsubstituted amino group), $R_5$—S—S— (wherein $R_5$ is hydrogen atom, an alkyl, a cycloalkyl, a cycloalkyl-alkyl, or an aryl, aralkyl, heterocyclic group, or heterocyclic group-substituted alkyl, these ring-containing groups having optionally substituent(s) on the ring), or $R_6CO$—S— (wherein $R_6CO$— is a residue of an N-substituted or unsubstituted amino acid).

The "alkyl" denotes an alkyl having 1 to 4 carbon atoms, such as methyl, ethyl, propyl, isopropyl or butyl.

The substituent in the alkyl includes amino, a mono- or di-($C_1$-$C_4$) alkyl substituted amino, hydroxy, a halogen (e.g. fluorine, chlorine, bromine or iodine), cyano, an acyloxy, and the like.

The "aralkyl" denotes a ($C_1$-$C_4$) alkyl substituted by aryl as mentioned above, such as benzyl, phenyethyl, naphthylmethyl, indenylmethyl, and the like.

The "aryl" includes, for example, phenyl, naphthyl, indenyl, and the like.

The "heterocyclic group" includes, for example, nitrogen-containing heterocyclic groups such as pyridyl, pyrrolyl, pyrazinyl, imidazolyl, indolyl, quinolyl, dihydropyridyl, pyrrolidinyl, or piperidyl; oxygen-containing heterocyclic groups such as furyl, pyranyl, dihydropyranyl, chromanyl, or 1,3-dioxolanyl; sulfur-containing heterocyclic groups such as thienyl; two or more hetero atoms-containing heterocyclic groups such as isothiazolyl, benzisoxazolyl, or morpholinyl.

The "cycloalkylene" denotes a cycloalkylene having 3 to 7 carbon atoms, such as cyclopropylene, cyclobutylene, cyclopentylene, cyclohexylene, or cycloheptylene.

The "cycloalkylidene" denotes a cycloalkylidene having 3 to 7 carbon atoms, such as cyclopropylidene, cyclobutylidene, cyclopentylidene, cyclohexylidene, or cycloheptylidene.

The "substituent on the ring" in aryl, aralkyl, heterocyclic group, heterocyclic group-substituted alkyl, aryloxyalkyl, heterocyclic amidoalkyl and benzene-fused lactonyl includes, the substituted or unsubstituted alkyl as mentioned above, phenyl, heterocyclic group, heterocyclic group-substituted alkyl, hydroxy, a lower alkoxy, a lower alkylthio, nitro, cyano, a halogen, a mono- or di-($C_1$-$C_4$) alkyl substituted or unsubstituted amino, an N-($C_1$-$C_4$) alkyl substituted or unsubstituted amino-($C_1$-$C_4$) alkoxy, and the like.

The "ring to be fused with phenylene" includes benzene, pyridine, piperidine, imidazole, oxazole, and the like.

The "group convertible into carboxyl when cleaved within the biobody" includes, for example, —$COOR_7$ (wherein $R_7$ is a cycloalkyl, a cycloalkyl-alkyl, an alkoxycarbonylalkyl, an N-substituted or unsubstituted aminocarbonylalkyl, an acyloxyalkyl, a substituted or unsubstituted alkyl, an alkoxycarbonyl, or an aryl, aralkyl, aryloxyalkyl, heterocyclic group, heterocyclic group-substituted alkyl, heterocyclic amidoalkyl, or benzene-fused lactonyl, these ring-containing groups having optionally substituent(s), or an N-substituted or unsubstituted aminocarbonyl), or —$CONHR_8$ (wherein —$NHR_8$ means a residue of natural amino acids which may optionally be esterified).

The "residue of N-substituted amino acids" denotes residues of amino acids N-substituted by an acyl group such as acetyl, propionyl, pivaloyl, benzoyl or cyclohexanecarbonyl, or by an N-protecting group such as t-butyloxycarbonyl or benzyloxycarbonyl, and includes, for example, N-(cyclohexanecarbonyl)-D-alanine, N-(t-butyloxycarbonyl)-glycine, N-(benzyloxycarbonyl)-L-phenylalanine, and the like.

The "acyl" in acyloxy and acyloxyalkyl includes acetyl, propionyl, pivaloyl, benzoyl, and the like.

The "lower alkoxy" denotes an alkoxy having 1 to 4 carbon atoms, such as methoxy, ethoxy, propoxy, and butoxy.

The "lower alkylthio" denotes an alkylthio having 1 to 4 carbon atoms, such as methylthio, ethylthio, propylthio, and butylthio.

The "halogen" includes fluorine, chlorine, bromine, and iodine.

The "mono- or di-($C_1$-$C_4$) alkyl substituted amino" includes methylamino, ethylamino, isopropylamino, dimethylamino and diethylamino.

The "N-($C_1$-$C_4$) alkyl substituted or unsubstituted amino-($C_1$-$C_4$) alkoxy" includes methylaminomethoxy, dimethylaminomethoxy, isopropylaminomethoxy, 2-(dimethylamino)-ethoxy, aminomethoxy and 2-aminoethoxy.

The "cycloalkyl" denotes a cycloalkyl having 3 to 7 carbon atoms, such as cyclopropyl, cyclobutyl, cyclopentyl, cyclohexyl, and cycloheptyl.

The compounds of this invention contain asymmetric carbon and hence may be present in the form of optical isomers. Thus, the compounds of this invention include R-isomer, S-isomer, and a mixture of these isomers.

The compounds of this invention may also be present in the form of a hydrate, which is included in this invention.

Moreover, the compounds of the formula (I) wherein $R_1$ is mercapto may be present in the form of a dimer which is bonded via —S—S— bond, which is also included in this invention.

The preferred compounds of this invention are the compounds of the formula (I) wherein X is a ($C_1$-$C_4$) alkyl-substituted phenylene or unsubstituted phenylene, more preferably, $R_1$ is mercapto or acetylthio, W is hydrogen atom, $R_2$ is phenyl or isopropyl, and $R_3$ is carboxyl.

Particularly preferred compounds of this invention are the compounds of the formula:

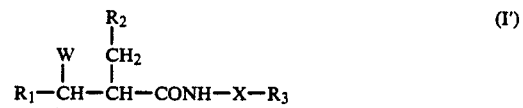

wherein $R_1$ is —S—$COR_4$ ($R_4$ is $C_1$-$C_4$ alkyl), W is hydrogen atom, $R_2$ is phenyl, X is 5-methylated 1,3-phenylene, and $R_3$ is carboxyl, or a pharmaceutically acceptable salt thereof.

Specifically preferred compounds are as follows.

3-[(2-Acetylthiomethyl-3-phenylpropionyl)amino]-5-methylbenzoic acid (compound of Example 1)

3-[(2-Mercaptomethyl-3-phenylpropionyl)amino]-5-methylbenzoic acid (compound of Example 2)

3-[(2-Acetylthiomethyl-3-phenylpropionyl)amino]-2-methylbenzoic acid (compound of Example 3)

3-[(2-Mercaptomethyl-3-phenylpropionyl)amino]-2-methylbenzoic acid (compound of Example 7)

3-[(2-Acetylthiomethyl-3-phenylpropionyl)amino]-5-ethylbenzoic acid (compound of Example 64)

3-[(2-Mercaptomethyl-3-phenylpropionyl)amino]-5-ethylbenzoic acid (compound of Example 65)

3-[(2-Acetylthiomethyl-4-methylpentanonyl)amino]-2-methylbenzoic acid (compound of Example 175)

3-[(2-Acetylthiomethyl-4-methylpentanonyl)amino]-5-methylbenzoic acid (compound of Example 176)

3-[(2-Mercaptomethyl-4-methylpentanonyl)amino]-benzoic acid (compound of Example 186)

3-[(2-Mercaptomethyl-4-methylpentanonyl)amino]-2-methylbenzoic acid (compound of Example 187)

3-[(2-Propionylthiomethyl-3-phenylpropionyl)amino]-5-methylbenzoic acid (compound of Example 196)

The solid solution of the compound (I) of this invention with an amino acid can be prepared by mixing a solution of the compound (I) of this invention in dioxane or t-butanol and a solution of an amino acid in water or a mixture of water and dioxane or t-butanol, followed by lyophilization of the mixture. The amino acid includes, for example, glycine, phenylalanine, leucine, asparagine, aspartic acid, 3-aminobenzoic acid.

Preferred solid solution is one with glycine. More preferably, the solid solution is one of the compound of the formula (I) wherein $R_1$ is mercapto or acethylthio, W is hydrogen atom, $R_2$ is phenyl, and X is a ($C_1$–$C_4$) alkyl-substituted phenylene or unsubstituted phenylene with glycine.

Specifically preferred solid solutions are as follows.

Solid solution of 3-[(2-mercaptomethyl-3-phenylpropionyl)amino]benzoic acid with glycine (compound of Example 87)

Solid solution of 3-[(2-acetylthiomethyl-3-phenylpropionyl)amino]-5-ethylbenzoic acid with glycine (compound of Example 103)

Solid solution of 3-[(2-mercaptomethyl-3-phenylpropionyl)amino]-2-methylbenzoic acid with glycine (compound of Example 104)

Solid solution of 3-[(2-mercaptomethyl-3-phenylpropionyl)amino]-5-methylbenzoic acid with glycine (compound of Example 105)

The compounds (I) of this invention can be prepared by various processes, for example, by the following processes.

(1) The compounds (I) of this invention are prepared by reacting a compound of the formula:

$$H_2N-X-R_3 \qquad (II)$$

wherein X and $R_3$ are as defined above, with a compound of the formula:

wherein $R_1$, $R_2$ and W are as defined above, or a reactive derivative thereof.

The above reaction can be carried out by the conventional methods which are usually used in peptide synthesis, as disclosed in Houben and Weil, "Methoden der Organischen Chemie, 15, second edition (1974); Nobuo Izumiya, "Primer and Experiment in Peptide Synthesis", issued by Maruzen (1985), and others.

More specifically, the reaction can be carried out by reacting the compound (II) and the compound (III) in the presence of a condensing agent or by reacting a reactive derivative of the compound (III) with the compound (II). The condensing agent includes dicyclohexylcarbodiimide (abbreviated as "DCC"), 1-ethyl-3-(3-dimethylaminopropyl)-carbodiimide hydrochloride (abbreviated as "EDC.HCl"), carbonyldiimidazole, 1-ethoxycarbonyl-2-ethoxy-1,2-dihydroquinoline, and the like. Other reagents such as 1-hydroxybenzotriazole (abbreviated as "HOBt") may be added to the reaction system.

The reactive derivative of the compound (III) includes acid anhydride, mixed acid anhydride, activated ester, acid halide, and the like.

The mixed acid anhydride includes, for example, mixed anhydrides with alkyl chloroformates (e.g. ethyl chloroformate, isobutyl chloroformate, etc.), mixed anhydrides with aryl chloroformates (e.g. phenyl chloroformate, etc.), mixed anhydrides with aliphatic carboxylic acids (e.g. pivalic acid, isovaleric acid, etc.), and the like. The activated ester includes, for example, esters with alcohols or phenols such as 1-hydroxybenzotriazole, N-hydroxysuccinimide, N-hydroxyphthalimide, cyanomethanol, pentachlorophenol, 2,4,5-trichlorophenol, 2,4-dinitrophenol, p-nitrophenol, and the like. The acid halide includes, for example, acid chloride, acid bromide, and the like, preferably acid chloride.

The above reaction is usually carried out in a solvent at a temperature of $-50°$ to $150°$ C., preferably $-30°$ to $60°$ C. Suitable solvent may vary depending on the kinds of the starting compounds and others, but includes, for example, aromatic hydrocarbons (e.g. benzene, toluene, etc.), halogenated hydrocarbons (e.g. dichloromethane, chloroform, etc.), ethers (e.g. tetrahydrofuran, dioxane, etc.), acetone, acetonitrile, ethyl acetate, dimethylformamide (abbreviated as "DMF"), dimethylsulfoxide, pyridine, water, or a mixture of these solvents. In case of a two phase solvent system, the reaction may be carried out in the presence of a phase transfer catalyst (e.g. tetra-n-butyl-ammonium bromide, etc.).

When an acid is produced as a by-product in the reaction, the reaction is preferably carried out in the presence of an acid acceptor such as an base. The base includes, for example, alkali metal hydroxides (e.g. sodium hydroxide, potassium hydroxide, etc.), alkali metal carbonates (e.g. sodium carbonate, potassium carbonate, etc.), alkali metal hydrogen carbonates (e.g. sodium hydrogen carbonate, potassium hydrogen carbonate, etc.), organic amines (e.g. triethylamine, N-methylmorpholine, N,N-dimethylaniline, etc.), and the like.

The starting compound (II) may optionally be used in the form of an acid addition salt.

When the starting compound (II) and/or (III) contains an amino group which does not participate in the reaction, the amino group may optionally be protected, and the protecting group is removed after completion of the reaction. The protecting group includes any groups which are usually used in peptide synthesis, for example, t-butyloxycarbonyl, benzyloxycarbonyl, and the like.

The starting compounds (II) and (III) can be prepared by known methods or a modified method thereof.

The compounds of the formula (I) wherein $R_1$ is mercapto and/or $R_3$ is carboxyl can preferably be prepared by hydrolysis of the corresponding compound (I) wherein the mercapto is protected by a lower alkanoyl or benzoyl, and/or the carboxyl is protected by a lower alkyl or benzyl, or alternatively by catalytic reduction of the corresponding compound (I) wherein $R_1$ is benzylthio.

The hydrolysis can be carried out by contacting the protected compound (I) above-mentioned with water, usually in the presence of a base. The base includes, for example, alkali metal hydroxides (e.g. sodium hydroxide, potassium hydroxide, etc.), alkali metal carbonates (e.g. sodium carbonate, potassium carbonate, etc.), ammonia, pyrrolidine, triethylamine, and the like. The reaction is usually carried out in water, but may optionally be carried out in a mixture of water and other solvents such as methanol, ethanol, dioxane, ethyleneglycol dimethyl ether, benzene, pyridine, acetonitrile, and the like. The reaction temperature is usually in the range of 0° to 150° C.

The catalytic reduction is carried out, for example, by treating the compound (I) wherein $R_1$ is benzylthio with sodium metal in liquid ammonia.

The compounds (I) wherein $R_1$ is mercapto may be converted into various derivatives as follows. That is, the compound is reacted with a compound of the formula: $R_4$—COOH (wherein $R_4$ is as defined above), $R_6$CO—OH (wherein $R_6$CO— is as defined above) or a reactive derivative thereof by a conventional method to give the corresponding compound (I) wherein $R_1$ is $R_4$—CO—S— (wherein $R_4$ is as defined above) or $R_6$CO—S— (wherein $R_6$CO— is as defined above).

Besides, the compound (I) wherein $R_1$ is mercapto is oxidized by a conventional method to give a dimer thereof which is bonded via —S—S— bond. Reversely, the dimer bound via —S—S— bond may be reduced by a conventional method to give the compound (I) wherein $R_1$ is mercapto.

(2) Alternatively, the compounds (I) of this invention can be prepared by reacting a compound of the formula:

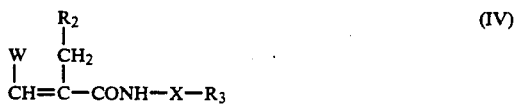

wherein $R_2$, W, X and $R_3$ are as defined above, or a compound of the formula:

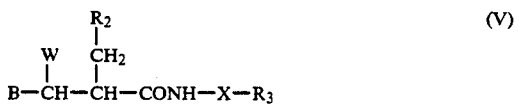

wherein B is a reactive group, and $R_2$, W, X and $R_3$ are as defined above, with a compound of the formula:

wherein $R_1$ is as defined above.

The reactive group (B) in the compound (V) includes, for example, halogen atoms (e.g. chlorine, bromine, or iodine), lower alkylsulfonyloxy (e.g. methanesulfonyloxy, etc.), arylsulfonyloxy (e.g. benzenesulfonyloxy, p-toluenesulfonyloxy, etc.).

The reaction is usually carried out by stirring a mixture of the starting compound (IV) or (V) and the starting compound (VI) in a solvent or without using any solvent at a temperature of 20° to 150° C. The solvent includes the same solvents as used in the above process (1). When an acid is produced as a by-product, the reaction is preferably carried out in the presence of an acid acceptor such as a base like in the above process (1). The starting compounds (IV) and (V) can be prepared by a known method or a modified method thereof.

(3) The compounds (I) wherein $R_3$ is a group convertible into carboxyl when cleaved in the biobody can also be prepared by reacting a compound of the formula:

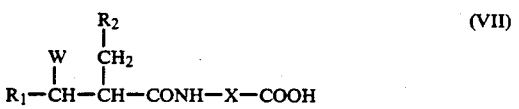

wherein $R_1$, $R_2$, W and X are as defibed above, or a reactive derivative thereof with a compound of the formula:

wherein $R_7$ is as defined above, or a reactive derivative thereof, or with a compound of the formula:

wherein $R_8$ is as defined above.

The above reaction is usually carried out by reacting the compound (VII) and the compound (VIII) or (IX) in the presence of a condensing agent, reacting a reactive derivative of the compound (VII) and the compound (VIII) or (IX), or reacting a reactive derivative of the compound (VIII) and the compound (VII). The condensing agent includes DCC, EDC.HCl, and the like. An agent such as 4-dimethylaminopyridine may also be added to the reaction system.

When the compound (VII) is used in the form of a reactive derivative thereof, the reaction is carried out in the same manner as in the above process (1). Besides, when the compound (VIII) is used in the form of a reactive derivative thereof, the reaction is carried out in the same manner as described in the above process (2).

The compounds (I) of this invention as prepared by the above processes can be isolated and purified by conventional methods such as chromatography, recrystallization, or reprecipitation. Depending on the conditions of isolation and purification, the desired product may be obtained in the form of a salt or in a free form, but these may be converted into each other form by conventional method.

The optically active compounds of this invention may be isolated by resolution of the racemic mixture in usual manner. Besides, when optically active starting compounds are used, the desired compounds can be obtained in the optically active form.

Pharmacological Activities (1) Analgesic activity (mouse phenylquinone writhing test)

Female Std:ddy mice (weighing 18-22 g) were used. Each animal was given intraperitoneally 10 ml/kg of 0.03% phenylquinone in 5% aqueous ethanol, and the number of writhes was counted for 15 minutes, beginning 5 minutes after the injection of phenylquinone. Test compounds, suspended or dissolved in 0.5% gum tragacanth aqueous solution, were given orally 30 minutes before the injection of phenylquinone. A reduction in writhes counts greater than 50% of the vehicle control value was considered to be effective. The $ED_{50}$-value was calculated from the effective rate according to the method of Litchfield and Wilcoxon.

Besides, the inhibitory rate (%) of the test compounds was also calculated when the test compounds were orally administered in a dose of 100 mg/kg according to the following formula:

$$\text{Inhibitory rate (\%)} = \frac{A - B}{A} \times 100$$

wherein

A is average writhe counts of the vehicle control group,

B is average writhe counts of the test compound group.

The test results are shown in Table 1.

As is shown in Table 1, the test compounds showed much stronger analgesic activity than the reference compound, thiorphan.

TABLE 1

| Test compounds | $ED_{50}$ (mg/kg, p.o.) | Inhibitory rate % (100 mg/kg, p.o.) |
|---|---|---|
| 1* | 22.3 | 92.0 |
| 2 | 16.6 | — |
| 3 | 21.6 | — |
| 7 | 17.9 | — |
| 64 | 11.0 | — |
| 65 | 22.9 | — |
| 87 | 10.1 | — |
| 103 | 9.3 | — |
| 104 | 6.0 | — |
| 105 | 7.3 | — |
| 175 | 21.1 | — |
| 176 | 22.9 | — |
| 186 | 15.0 | — |
| 187 | 20.1 | — |
| 196 | 12.4 | 78.0 |
| 197 | — | 67.1 |
| 198 | 50.0 | 66.4 |
| 199 | 90.9 | 58.6 |
| 200 | — | 63.6 |
| Thiorphan | 137 | 32.7 |

*This means the number of working examples. (hereinafter the same)

(2) Enkephalinase inhibitory activity in vivo (Potentiation of the analgesic activity of DAME)

Pressure pain was induced by pressing the tail of male Std:ddy mice (weighing 20–26 g) using an apparatus for pressure measurement. The pressure pain threshold (biting response) was measured as mm. Test compound, dissolved or suspended in 0.5% gum tragacanth aqueous solution, was given orally 30 minutes before intracisternaly administration of D-Ala$^2$-Met$^5$-enkephalin (DAME). Five minutes after administration of DAME, the pressure pain threshold was measured, and the potentiation activity of test compounds on the analgesic effect of DAME was tested. The results are shown in Table 2.

As is clear from the results, the analgesic activity of DAME was potentiated by the test compounds in a dose-dependent manner. Accordingly, the test compounds showed enkephalinase inhibitory activity in vivo.

TABLE 2

| Test compounds | $ED_{50}$ (mg/kg, p.o.) |
|---|---|
| 2 | 20.2 |
| 7 | 38.3 |
| 64 | 20.8 |
| 68 (a)-[2] | 51.0 |
| 87 | 26.5 |

(3) Enkephalinase inhibitory activity in vitro (i) Separation of enzyme

Enkephalin degrading enzymes were separated according to the method described by Gorenstein and Snyder (Life Science, 25, 2065 (1979)).

Male Std:Wistar rats were decapitated and the striata were removed. These were homogenized in 30 volumes of 50 mM Tris-HCl buffer (pH 7.4) and centrifuged for 15 minutes at 1,000×g. The supernatant was centrifuged for 15 minutes at 50,000×g. The pellet was washed three times with the same buffer and then suspended in 15 volumes of 50 mM Tris-HCl buffer (pH 7.4) containing 1% Triton X-100, followed by incubation for 45 minutes at 37° C. After centrifugation for 1 hour at 100,000×g, the supernatant was applied onto DEAE-cellulose ion exchange chromatography column. The fraction containing enkephalin dipeptidylcarboxypeptidase was used as enkephalinase sample.

(ii) Measurement of inhibitory activity

After preincubation of test compound and enkephalinase for 5 minutes at 37° C., [$^3$H]-leucine-enkephalin (substrate) was added to the reaction mixture and then the mixture was incubated for 1 hour at 37° C. (final volume: 100 µl, final concentration of substarate: 20 nM). Ice-cold 0.2 N HCl was added to the mixture to stop the reaction. Substrate and metabolites were separated with TLC and Porapak Q® column by the method of Vogel and Alstein [FEBS Letters, 80, 332 (1977)]. Enzyme activity was estimated from the production rate of [$^3$H]-Tyr-Gly-Gly. The $IC_{50}$-value of test compounds was calculated from the inhibitory rates, estimated from the difference between the enzyme activities in the absence and the presence of test compound. The results are shown in Table 3.

As is clear from the results, the test compounds showed enkephalinase inhibitory activity in vitro.

TABLE 3

| Test compounds | $IC_{50}$ (nM) |
|---|---|
| 2 | 5.4 |
| 7 | 7.5 |
| 65 | 4.6 |
| 68 (a)-[2] | 2.1 |
| 186 | 8.4 |
| 187 | 7.8 |

As is clear from the above experiments (1) to (3), the compounds of this invention show excellent analgesic activity due to enkephalinase inhibitory activity and hence are useful as a medicament for the treatment of variety of mild to moderate pain such as postoperative pain, post-trauma pain, dental pain and chronic pain associated with arthritic diseases and musculoskeletal disorders. Moreover, the compounds of this invention have low toxicity, and even by administration of the compounds in a far larger amount than the therapeutically effective amount, no death of the experimental animals was observed.

The dosage of the compounds of this invention may vary in accordance with the kinds of the compounds, age and weight of the patients, the severity of the diseases, and the administration routes, but is usually in the range of 20 mg to 2 g per day. They can be administered by oral or parenteral route.

The compounds of this invention are usually used in a pharmaceutical preparation. The pharmaceutical preparation includes, for example, tablets, capsules, granules, fine granules, powders, syrups, solutions, suspensions, injections, suppositories, and the like. These preparations are prepared by admixing the compounds of this invention with conventional pharmaceutical carriers or diluents in a usual manner. The pharmaceutical carriers and diluents include any conventional carriers or diluents which are used in the field of pharmaceutical preparations and are not affective to the compounds of this invention. Suitable examples of the carriers and diluents are lactose, sugar, glucose, starch, mannitol, dextrin, cyclodextrins, crystalline cellulose, methylcellulose, carboxymethyl cellulose sodium, water, ethanol, glycerin, propylene glycol, polyvinylpyrrolidone, magnesium stearate, bentonite, talc, gum arabic, gelatin, gum tragacanth, cacao butter, sodium laurylsulfate, white vaseline, paraffin, silicon, and the like.

The liquid preparations may be in the form which is dissolved or suspended in water or any other solvent when used. Besides, the tablets, granules and fine granules may optionally be subjected to conventional coating.

The compounds and preparations of this invention are illustrated by the following Examples but should not be construed to be limited thereto.

EXAMPLE 1

Preparation of
3-[(2-acetylthiomethyl-3-phenylpropionyl)amino]-5-methylbenzoic acid:

3-Amino-5-methylbenzoic acid (1.9 g) is dissolved in a 60% aqueous solution of tetrahydrofuran (30 ml) containing triethylamine (2.3 g), and to the mixture is added dropwise a solution of 2-acetylthiomethyl-3-phenylpropionyl chloride (3.2 g) in tetrahydrofuran (20 ml) with stirring under ice cooling, and the mixture is stirred at room temperature for 2 hours. Tetrahydrofuran is distilled off under reduced pressure, and the residue is extracted with ethyl acetate (100 ml). The extract is washed with saturated aqueous sodium chloride solution and dried over anhydrous sodium sulfate, and then ethyl acetate is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (2.4 g).

m.p.: 160°-161° C. (amorphous)

IR (KBr; cm$^{-1}$): 1680, 1650

Elementary analysis for $C_{20}H_{21}NO_4S$: Calcd. (%): C,64.67; H,5.70; N,3.77; S,8.63 Found (%): C,64.82; H,5.82; N,3.82; S,8.64

EXAMPLE 2

Preparation of
3-[(2-mercaptomethyl-3-phenylpropionyl)amino]-5-methylbenzoic acid 3-[(2-Acetylthiomethyl-3-phenylpropionyl)amino]-5-methylbenzoic acid (compound of Example 1) (1.7 g) is dissolved in methanol (9 ml), and thereto is added 1 N aqueous sodium hydroxide solution (9 ml) under nitrogen, and the mixture is stirred at room temperature for 30 minutes. The reaction mixture is adjusted to pH 1 by adding dropwise conc. hydrochloric acid, and the residue is purified by a medium pressure column chromatography with CHP-20P (eluant, water-acetonitrile). The fractions containing the desired compound are collected and concentrated into dryness under reduced pressure to give the title compound (0.9 g).

m.p.: 177°-178° C. (amorphous)

IR (KBr; cm$^{-1}$): 1680, 1650

Elementary analysis for $C_{18}H_{19}NO_3S$: Calcd. (%): C,65.63; H,5.81; N,4.25; S,9.73 Found (%): C,65.87; H,6.02; N,4.25; S,9.61

EXAMPLE 3

Preparation of
3-[(2-acetylthiomethyl-3-phenylpropionyl)amino]-2-methylbenzoic acid (1) 2-Methyl-3-nitrobenzoic acid (5 g) is dissolved in ethanol (50 ml) and the mixture is subjected to catalytic reduction with 5% palladium carbon (0.25 g) at room temperature for 5 hours. The catalyst is removed by filtration, and the filtrate is concentrated to give 3-amino-2-methylbenzoic acid (4.4 g).

m.p.: 188°-189° C.

IR (KBr; cm$^{-1}$): 1620

Elementary analysis for $C_8H_9NO_2$: Calcd. (%): C,63.56; H,6.00; N,9.27 Found (%): C,63.32; H,6.05; N,9.43

(2) The compound prepared in the above (1) (1.9 g) is dissolved in a 60% aqueous solution of tetrahydrofuran (30 ml) containing triethylamine (2.3 g), and to the mixture is added dropwise a solution of 2-acetylthiomethyl-3-phenylpropionyl chloride (3.2 g) in tetrahydrofuran (20 ml) with stirring under ice cooling, and the mixture is stirred at room temperature for 2 hours. Tetrahydrofuran is distilled off under reduced pressure, and the residue is dissolved in acetonitrile and purified by a medium pressure column chromatography with CHP-20P (eluant, water-acetonitrile). The fractions containing the desired compound are collected and concentrated into dryness under reduced pressure to give the title compound (1.8 g).

m.p.: 162°-163° C. (amorphous)

IR (KBr; cm$^{-1}$): 1680, 1650

Elementary analysis for $C_{20}H_{21}NO_4S \cdot 0.25H_2O$: Calcd. (%): C,63.90; H,5.76; N,3.73; S,8.53 Found (%): C,64.01; H,5.71; N,3.82; S,8.74

EXAMPLE 4

Preparation of
2-[(2-acetylthiomethyl-3-phenylpropionyl)amino]-5-chlorobenzoic acid In the same manner as described in Example 3 except that 5-chloro-2-nitrobenzoic acid is used, there is prepared the title compound as an oily substance.

IR (film; cm$^{-1}$): 1680

Elementary analysis for $C_{19}H_{18}ClNO_4S \cdot 0.25H_2O$: Calcd. (%): C,57.57; H,4.70; Cl,8.94; N,3.53; S,8.09 Found (%): C,57.77; H,4.81; Cl,8.91; N,3.50; S,7.93

EXAMPLE 5

Preparation of
2-[(2-acetylthiomethyl-3-phenylpropionyl)amino]-3-chlorobenzoic acid In the same manner as described in Example 3 except that 3-chloro-2-nitrobenzoic acid is used, there is prepared the title compound.

m.p.: 123°-127° C. (amorphous)

IR (KBr; cm$^{-1}$): 1680, 1650

Elementary analysis for $C_{19}H_{18}ClNO_4S$: Calcd. (%): C,58.24; H,4.63; Cl,9.05; N,3.57; S,8.18 Found (%): C,58.28; H,4.76; Cl,9.33; N,3.53; S,8.15

EXAMPLE 6

Preparation of
2-[(2-acetylthiomethyl-3-phenylpropionyl)amino]-4-chlorobenzoic acid In the same manner as described in Example 3 except that 4-chloro-2-nitrobenzoic acid is used, there is prepared the title compound.
m.p.: 143°-144° C. (amorphous)
IR (KBr; cm$^{-1}$): 1660
Elementary analysis for $C_{19}H_{18}ClNO_4S$: Calcd. (%): C,58.24; H,4.63; Cl,9.05; N,3.57; S,8.18 Found (%): C,58.27; H,4.77; Cl,8.99; N,3.52; S,8.18

EXAMPLE 7

Preparation of
3-[(2-mercaptomethyl-3-phenylpropionyl)amino]-2-methylbenzoic acid In the same manner as described in Example 2 except that 3-[(2-acetylthiomethyl-3-phenylpropionyl)amino]-2-methylbenzoic acid (compound of Example 3) is used, there is prepared the title compound
m.p.: 179°-181° C. (amorphous)
IR (KBr; cm$^{-1}$): 1670, 1630
Elementary analysis for $C_{18}H_{19}NO_3S$: Calcd. (%): C,65.63; H,5.81; N,4.25; S,9.73 Found (%): C,65.72; H,5.95; N,4.16; S,9.92

EXAMPLE 8

Preparation of
2-[(2-mercaptomethyl-3-phenylpropionyl)amino]-5-chlorobenzoic acid In the same manner as described in Example 2 except that 2-[(2-acetylthiomethyl-3-phenylpropionyl)amino]-5-chlorobenzoic acid (compound of Example 4) is used, there is prepared the title compound.
m.p.: 157°-158° C. (amorphous)
IR (KBr; cm$^{-1}$): 1680, 1620
Elementary analysis for $C_{17}H_{16}ClNO_3S$: Calcd. (%): C,58.37; H,4.61; Cl,10.13; N,4.00; S,9.17 Found (%): C,58.41; H,4.65; Cl,10.21; N,3.96; S,8.91

EXAMPLE 9

Preparation of
2-[(2-mercaptomethyl-3-phenylpropionyl)amino]-4-chlorobenzoic acid In the same manner as described in Example 2 except that 2-[(2-acetylthiomethyl-3-phenylpropionyl)amino]-4-chlorobenzoic acid (compound of Example 6) is used, there is prepared the title compound.
m.p.: 134°-136° C. (amorphous)
IR (KBr; cm$^{-1}$) 1650
Elementary analysis for $C_{17}H_{16}ClNO_3S$: Calcd. (%): C,58.37; H,4.61; Cl,10.13; N,4.00; S,9.17 Found (%): C,58.22; H,4.67; Cl,10.35; N,4.01; S,9.06

EXAMPLE 10

Preparation of
3-[(2-acetylthiomethyl-3-phenylpropionyl)amino]-4-(1-pyrrolidinyl)benzoic acid (1) 4-Chloro-3-nitrobenzoic acid (5.0 g) is suspended in xylene (50 ml), and thereto are added triethylamine (2.5 g) and pyrrolidine (2.0 g), and the mixture is refluxed for 2 hours. To the reaction mixture is added 10% aqueous citric acid solution, and the precipitated crystals are separated by filtration, washed with water and dried to give 3-nitro-4-(1-pyrrolidinyl)benzoic acid (5.6 g).

(2) The compound prepared in the above (1) (5 g) is dissolved in ethanol (100 ml) and the mixture is subjected to catalytic reduction with 10% palladium carbon (0.275 g) at 50° C for 5 hours. The catalyst is removed by filtration, and in the filtrate is dissolved oxalic acid (2.3 g), and the mixture is concentrated under reduced pressure. The resulting crystals are separated by filtration and dried to give 3-amino-4-(1-pyrrolidinyl)benzoic acid.hemioxalate (5.7 g).

(3) The compound prepared in the above (2) (1.6 g) is dissolved in water (10 ml) containing sodium hydrogen carbonate (1.3 g), and to the mixture is added dropwise a solution of 2-acetylthiomethyl-3-phenylpropionyl chloride (1.6 g) in tetrahydrofuran (15 ml) with stirring under ice cooling, and the mixture is stirred at room temperature for one hour. Tetrahydrofuran is distilled off under reduced pressure, and the residue is extracted with chloroform (50 ml). The extract is washed with 10% aqueous citric acid soltuion, 5% aqueous sodium hydrogen carbonate solution, and saturated aqueous sodium chloride solution in this order, dried over anhydrous sodium sulfate, and chloroform is distilled off under reduced pressure. The residue is dissolved in acetonitrile-water and purified by a medium pressure column chromatography with CHP-20P (eluant, water-acetonitrile). The fractions containing the desired compound are collected and concentrated into dryness under reduced pressure to give the title compound (0.9 g).
m.p.: 217°-222° C. (amorphous)
IR (KBr; cm$^{-1}$): 1650
Elementary analysis for $C_{23}H_{26}N_2O_4S$: Calcd. (%): C,64.77; H,6.14; N,6.57; S,7.52 Found (%): C,65.00; H,6.19; N,6.80; S,7.11

EXAMPLE 11

Preparation of
3-[(2-acetylthiomethyl-3-phenylpropionyl)amino]-4-piperidinobenzoic acid In the same manner as described in Example 10, there is prepared the title compound.
m.p.: 170°-174° C. (amorphous)
IR (KBr; cm$^{-1}$): 1660
Elementary analysis for $C_{24}H_{28}N_2O_4S$: Calcd. (%): C,65.43; H,6.41; N,6.36; S,7.28 Found (%): C,65.48; H,6.51; N,6.19; S,7.29

EXAMPLE 12

Preparation of
5-[(2-acetylthiomethyl-3-phenylpropionyl)amino]-2-(1-pyrrolidinyl)benzoic acid In the same manner as described in Example 10, there is prepared the title compound.
m.p.: 176°-178° C. (amorphous)
IR (KBr; cm$^{-1}$): 1660
Elementary analysis for $C_{23}H_{26}N_2O_4S$: Calcd. (%) C,64.77; H,6.14; N,6.57; S,7.52 Found (%): C,64.75; H,6.33; N,6.47; S,7.25

EXAMPLE 13

Preparation of 5-[(2-acetylthiomethyl-3-phenylpropionyl)amino]-2-dimethylaminobenzoic acid In the same manner as described in Example 10, there is prepared the title compound.
m.p.: 168°–169° C. (amorphous)
IR (KBr; cm$^{-1}$): 1670
Elementary analysis for $C_{21}H_{24}N_2O_4S$: Calcd. (%): C,62.98; H,6.04; N,6.99; S,8.01 Found (%): C,62.84; H,6.15; N,7.10; S,8.25

EXAMPLE 14

Preparation of methyl 3-[(2-acetylthiomethyl-3-phenylpropionyl)amino]-4-(1-pyrrolidinyl)benzoate (1) 3-Amino-4-(1-pyrrolidinyl)benzoic acid.hemioxalate (5.0 g) is suspended in methanol (40 ml) and thereto is added p-toluenesulfonic acid (2.5 g), and the mixture is refluxed for 3 hours. Mathanol is distilled off under reduced pressure, and the residue is extracted with ethyl acetate (100 ml). The extract is washed with 5% aqueous sodium hydrogen carbonate solution and saturated aqueous sodium chloride solution in this order, dried over anhydrous sodium sulfate, and ethyl acetate is distilled off to give methyl 3-amino-4-(1-pyrrolidinyl)-benzoate (3.4 g).

(2) The compound prepared in the above (1) (3.0 g) is dissolved in chloroform (40 ml), and to the mixture is added dropwise a solution of 2-acetylthiomethyl-3-phenylpropionyl chloride (3.2 g) in chloroform (20 ml) with stirring under ice cooling, and the mixture is stirred at room temperature for 5 hours. The reaction mixture is diluted with chloroform, washed with 5% aqueous sodium hydrogen carbonate solution and saturated aqueous sodium chloride solution in this order, dried over anhydrous sodium sulfate, and chloroform is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (1.1 g).
m.p.: 72°–75° C. (amorphous)
IR (KBr; cm$^{-1}$): 1680, 1640
Elementary analysis for $C_{24}H_{28}N_2O_4S$: Calcd. (%): C,65.43; H,6.41; N,6.36; S,7.28 Found (%): C,65.39; H,6.54; N,6.31; S,7.37

EXAMPLE 15

Preparation of methyl 3-[(2-acetylthiomethyl-3-phenylpropionyl)amino]-4-morpholinobenzoate (1) 4-Morpholino-3-nitrobenzoic acid prepared in the same manner as in Example 10(1) (3.0 g) is dissolved in methanol (15 ml), and thereto is added dropwise a 10% solution of trimethylsilyldiazomethane in n-hexane in an equimolar amount, and the mixture is stirred at room temperature for one hour. Methanol is distilled off under reduced pressure, and the residue is extracted with ethyl acetate. The extract is washed with 5% aqueous sodium hydrogen carbonate solution and saturated aqueous sodium chloride solution in this order, dried over anhydrous sodium sulfate, and ethyl acetate is distilled off under reduced pressure to give methyl 4-morpholino-3-nitrobenzoate (3.2 g).

(2) The compound prepared in the above (1) (3.2 g) is dissolved in methanol (65 ml) and the mixture is subjected to catalytic reduction with 10% palladium carbon (0.16 g) at room temperature under atmospheric pressure for 2 hours. The catalyst is removed by filtration, and the filtrate is distilled under reduced pressure to give methyl 3-amino-4-morpholinobenzoate (3.0 g).

(3) The compound prepared in the above (2) (3.0 g) is dissolved in chloroform (40 ml), and thereto is added dropwise a solution of 2-acetylthiomethyl-3-phenylpropionyl chloride (3.2 g) in chloroform (20 ml) with stirring under ice cooling, and the mixture is stirred at room temperature for 2 hours. The reaction mixture is diluted with chloroform, washed with 5% aqueous sodium hydrogen carbonate solution and saturated aqueous sodium chloride solution in this order, dried over anhydrous sodium sulfate, and chloroform is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (2.0 g) as an oily substance.
IR (film; cm$^{-1}$): 1720, 1680
Elementary analysis for $C_{24}H_{28}N_2O_5S.H_2O$: Calcd. (%): C,60.74; H,6.37; N,5.90; S,6.76 Found (%): C,60.61; H,6.14; N,5.66; S,6.50

EXAMPLE 16

Preparation of 3-[(2-mercaptomethyl-3-phenylpropionyl)amino]-4-(1-pyrrolidinyl)benzoic acid Metyl 3-[(2-acetylthiomethyl-3-phenylpropionyl)-amino]-4-(1-pyrrolidinyl)benzoate (compound of Example 14) (0.8 g) is dissolved in methanol (5 ml), and thereto is added 1 N aqueous sodium hydroxide solution (5.5 ml) under nitrogen, and the mixture is stirred at room temperature for 30 minutes. The reaction mixture is acidified with hydrochloric acid and purified by a medium pressure column chromatography with CHP-20P (eluant, water-acetonitrile). The fractions containing the desired compound are collected and concentrated into dryness under reduced pressure to give the title compound (0.3 g).
m.p.: 229°–234° C. (amorphous, decomp.)
IR (KBr; cm$^{-1}$): 1650 (broad)
Elementary analysis for $C_{21}H_{24}N_2O_3S$: Calcd. (%): C,65.60; H,6.29; N,7.29; S,8.34 Found (%): C,65.33; H,6.16; N,7.24; S,8.23

EXAMPLE 17

Preparation of 3-[(2-mercaptomethyl-3-phenylpropionyl)amino]-4-morpholinobenzoic acid In the same manner as described in Example 16, there is prepared the title compound.
m.p.: 218°–222° C. (amorphous)
IR (KBr; cm$^{-1}$): 1700, 1660
Elementary analysis for $C_{21}H_{24}N_2O_4S$: Calcd. (%): C,62.98; H,6.04; N,6.99; S,8.01 Found (%): C,62.98; H,6.04; N,7.01; S,8.29

EXAMPLE 18

Preparation of
3-[(2-mercaptomethyl-3-phenylpropionyl)amino]-4-piperidinobenzoic acid In the same manner as described in Example 2, there is prepared the title compound.
m.p.: 142°–146° C. (amorphous, decomp.)
IR (KBr; cm$^{-1}$): 1660
Elementary analysis for $C_{22}H_{26}N_2O_3S \cdot 0.75H_2O$: Calcd. (%): C,64.13; H,6.73; N,6.80; S,7.78 Found (%) C,63.72; H,6.43; N,6.61; S,7.70

EXAMPLE 19

Preparation of
5-[(2-mercaptomethyl-3-phenylpropionyl)amino]-2-(1-pyrrolidinyl)benzoic acid In the same manner as described in Example 2, there is prepared the title compound.
m.p.: 196°–198° C. (amorphous)
IR (KBr; cm$^{-1}$): 1660
Elementary analysis for $C_{21}H_{24}N_2O_3S$: Calcd. (%): C,65.60; H,6.29; N,7.29; S,8.34 Found (%): C,65.65; H,6.42; N,7.19; S,8.49

EXAMPLE 20

Preparation of
5-[(2-mercaptomethyl-3-phenylpropionyl)amino]-2-dimethylaminobenzoic acid In the same manner as described in Example 2, there is prepared the title compound.
m.p.: 85°–89° C. (amorphous)
IR (KBr; cm$^{-1}$): 1670 (broad)
Elementary analysis for $C_{19}H_{22}N_2O_3S$: Calcd. (%): C,62.87; H,6.25; N,7.72; S,8.83 Found (%): C,62.81; H,6.33; N,7.83; S,8.86

EXAMPLE 21

Preparation of
3-[(2-acetylthiomethyl-3-phenylpropionyl)amino]-4-methylbenzoic acid 3-Amino-4-methylbenzoic acid (1.5 g) is dissolved in a solution of sodium hydrogen carbonate (1.68 g) in water (25 ml), and to the mixture is added dropwise a solution of 2-acetylthiomethyl-3-phenylpropionyl chloride (2.86 g) in tetrahydrofuran (8 ml) with vigorously stirring, and the mixture is stirred at room temperature for 3 hours. Tetrahydrofuran is distilled off at a low temperature under reduced pressure, and the residue is washed with diethyl ether and acidified with hydrochloric acid, and the resulting oily substance is extracted with ethyl acetate. The extract is washed with saturated aqueous sodium chloride solution and dried over anhydrous sodium sulfate, and then the solvent is distilled off under reduced pressure. The oily residue is purified by a medium pressure column chromatography with CHP-20P (eluant, water-acetonitrile). The fractions containing the desired compound are collected, and acetonitrile is distilled off under reduced pressure, and the precipitated crystals are separated by filtration to give the title compound (1.93 g).
m.p.: 214°–216° C. (amorphous)
IR (KBr; cm$^{-1}$): 1680, 1650
Elementary analysis for $C_{20}H_{21}NO_4S$: Calcd. (%): C,64.67; H,5.70; N,3.77; S,8.63 Found (%): C,64.73; H,5.69; N,3.78; S,8.66

EXAMPLE 22

Preparation of
1-[(2-acetylthiomethyl-3-phenylpropionyl)amino]cyclopropanecarboxylic acid In the same manner as described in Example 21, there is prepared the title compoud.
m.p.: 169°–171° C. (amorphous)
IR (KBr; cm$^{-1}$): 1680, 1650
Elementary analysis for $C_{16}H_{19}NO_4S$: Calcd. (%): C,59.79; H,5.96; N,4.36; S,9.98 Found (%): C,59.75; H,6.05; N,4.27; S,10.03

EXAMPLE 23

Preparation of
3-[(2-acetylthiomethyl-3-phenylpropionyl)amino]-4-hydroxybenzoic acid In the same manner as described in Example 21, there is prepared the title compound.
m.p.: 202°–206° C. (amorphous)
IR (KBr; cm$^{-1}$): 1680, 1670
Elementary analysis for $C_{19}H_{19}NO_5S$: Calcd. (%): C,61.11; H,5.13; N,3.75; S,8.59 Found (%): C,61.26; H,5.15; N,3.42; S,8.87

EXAMPLE 24

Preparation of
3-[(2-acetylthiomethyl-3-phenylpropionyl)amino]-4-chlorobenzoic acid In the same manner as described in Example 21, there is prepared the title compound.
m.p.: 204°–206° C. (amorphous)
IR (KBr; cm$^{-1}$): 1680, 1660
Elementary analysis for $C_{19}H_{18}ClNO_4S$: Calcd. (%): C,58.24; H,4.63; Cl,9.05; N,3.57; S,8.18 Found (%): C,58.33; H,4.73; Cl,8.61; N,3.76; S,8.03

EXAMPLE 25

Preparation of
4-[(2-acetylthiomethyl-3-phenylpropionyl)amino]-3-methylbenzoic acid In the same manner as described in Example 21, there is prepared the title compound.
m.p.: 183°–186° C. (amorphous)
IR (KBr; cm$^{-1}$): 1680, 1650
Elementary analysis for $C_{20}H_{21}NO_4S$: Calcd. (%): C,64.67; H,5.70; N,3.77; S,8.63 Found (%): C,65.06; H,5.70; N,3.82; S,8.31

EXAMPLE 26

Preparation of
3-[(2-acetylthiomethyl-3-phenylpropionyl)amino]-4-methoxybenzoic acid In the same manner as described in Example 21, there is prepared the title compound.
m.p.: 172°–175° C. (amorphous)
IR (KBr; cm$^{-1}$): 1680, 1650
Elementary analysis for $C_{20}H_{21}NO_5S$: Calcd. (%): C,62.00; H,5.46; N,3.62; S,8.28 Found (%): C,62.38; H,5.52; N,3.64; S,7.93

EXAMPLE 27

Preparation of 5-[(2-acetylthiomethyl-3-phenylpropionyl)amino]-2-chlorobenzoic acid 2-Acetylthiomethyl-3-phenylpropionic acid (2.4 g) is dissolved in chloroform (20 ml) containing a few drops of DMF, and to the mixture is added thionyl chloride (2 ml), and the mixture is refluxed for 30 minutes. Excess thionyl chloride is distilled off under reduced pressure, and the oily residue is dissolved in tetrahydrofuran (20 ml). To the mixture is added a solution of 5-amino-2-chlorobenzoic acid (1.8 g) in 2 N aqueous sodium hydroxide solution with stirring under ice cooling which is kept at pH 7.6. After 30 minutes, the mixture is acidified with hydrochloric acid and thereto is added water. The mixture is extracted with ethyl acetate. The extract is washed with saturated aqueous sodium chloride solution and dried over anhydrous sodium sulfate, and then the solvent is distilled off under reduced pressure. The oily residue is purified by a medium pressure column chromatography with CHP-20P (eluant, water-acetonitrile). The fractions containing the desired compound are collected, and acetonitrile is distilled off under reduced pressure, and the precipitated crystals are separated by filtration to give the title compound (2.6 g).

m.p.: 163°–165° C. (amorphous)
IR (KBr; cm$^{-1}$): 1670
Elementary analysis for $C_{19}H_{18}ClNO_4S$: Calcd. (%) C,58.24; H,4.63; Cl,9.05; N,3.57; S,8.18 Found (%): C,58.47; H,4.76; Cl,8.97; N,3.54; S,7.97

EXAMPLE 28

Preparation of 3-[(2-mercaptomethyl-3-phenylpropionyl)amino]-4-methylbenzoic acid In the same manner as described in Example 2, there is prepared the title compound.
m.p.: 192°–194° C. (amorphous)
IR (KBr; cm$^{-1}$): 1680, 1640
Elementary analysis for $C_{18}H_{19}NO_3S$: Calcd. (%) C,65.63; H,5.81; N,4.25; S,9.73 Found (%): C,65.39; H,5.87; N,4.12; S,9.83

EXAMPLE 29

Preparation of 1-[(2-mercaptomethyl-3-phenylpropionyl)amino]cyclopropanecarboxylic acid In the same manner as described in Example 2, there is prepared the title compound.
m.p.: 222°–224° C. (amorphous)
IR (KBr; cm$^{-1}$): 1680, 1640
Elementary analysis for $C_{14}H_{17}NO_3S$: Calcd. (%) C,60.19; H,6.13; N,5.01; S,11.48 Found (%): C,60.34; H,6.14; N,4.99; S,11.52

EXAMPLE 30

Preparation of 3-[(2-mercaptomethyl-3-phenylpropionyl)amino]-4-hydroxybenzoic acid In the same manner as described in Example 2, there is prepared the title compound.
m.p.: 226°–227° C. (amorphous)
IR (KBr; cm$^{-1}$): 1660
Elementary analysis for $C_{17}H_{17}NO_4S$: Calcd. (%): C,61.62; H,5.17; N,4.23; S,9.68 Found (%): C,62.04; H,5.22; N,4.24; S,9.28

EXAMPLE 31

Preparation of 3-[(2-mercaptomethyl-3-phenylpropionyl)amino]-4-chlorobenzoic acid In the same manner as described in Example 2, there is prepared the title compound.
m.p.: 189°–191° C. (amorphous)
IR (KBr; cm$^{-1}$): 1690, 1660
Elementary analysis for $C_{17}H_{16}ClNO_3S$: Calcd. (%): C,58.37; H,4.61; Cl,10.13; N,4.00; S,9.17 Found (%): C,58.49; H,4.62; Cl,10.05; N,4.01; S,9.38

EXAMPLE 32

Preparation of 4-[(2-mercaptomethyl-3-phenylpropionyl)amino]-3-methylbenzoic acid In the same manner as described in Example 2, there is prepared the title compound.
m.p. 217°–218° C. (amorphous)
IR (KBr; cm$^{-1}$): 1670, 1650
Elementary analysis for $C_{18}H_{19}NO_3S$: Calcd. (%) C,65.63; H,5.81; N,4.25; S,9.73 Found (%): C,65.36; H,5.86; N,4.37; S,9.73

EXAMPLE 33

Preparation of 3-[(2-mercaptomethyl-3-phenylpropionyl)amino]-4-methoxybenzoic acid In the same manner as described in Example 2, there is prepared the title compound.
m.p.: 188°–192° C. (amorphous)
IR (KBr; cm$^{-1}$): 1680, 1650
Elementary analysis for $C_{18}H_{19}NO_4S$: Calcd. (%): C,62.59; H,5.54; N,4.06; S,9.28 Found (%): C,62.68; H,5.62; N,4.08; S,9.03

EXAMPLE 34

Preparation of 5-[(2-mercaptomethyl-3-phenylpropionyl)amino]-2-chlorobenzoic acid In the same manner as described in Example 2, there is prepared the title compound.
m.p.: 190°–192° C. (amorphous)
IR (KBr; cm$^{-1}$): 1690, 1650
Elementary analysis for $C_{17}H_{16}ClNO_3S$: Calcd. (%): C,58.37; H,4.61; Cl,10.13; N,4.00; S,9.17 Found (%): C,58.50; H,4.70; Cl,10.06; N,4.03; S,8.97

EXAMPLE 35

Preparation of benzyl 3-[(2-acetylthiomethyl-3-phenylpropionyl)amino]-4-methylbenzoate 3-[(2-Acetylthiomethyl-3-phenylpropionyl)amino]-4-methylbenzoic acid (compound of Example 21) (0.5 g), 4-dimethylaminopyridine (0.05 g), benzyl alcohol (0.17 g) and dichloromethane (20 ml) are mixed, and to the mixture is added EDC.HCl (0.27 g) with stirring under ice cooling, and the mixture is stirred at room temperature overnight. Dichloromethane is distilled off under reduced pressure, and the residue is dissolved in ethyl acetate, and the mixture is washed with 5% aqueous sodium hydrogen carbonate solution, 10% hydrochloric acid and saturated aqueous sodium chloride solution in this order and dried over anhydrous magnesium sulfate, and then ethyl acetate is distilled off under reduced pressure. The residue is dissolved in acetonitrile and purified by a medium pressure column chromatography with CHP-20P (eluent, water-acetonitrile). The fractions containing the desired compound are collected and the water and acetonitrile are distilled off under reduced pressure to give the title compound (0.40 g).

m.p.: 134°–135° C. (amorphous)
IR (KBr; cm$^{-1}$): 1720, 1680, 1650
Elementary analysis for $C_{27}H_{27}NO_4S$:
Calcd. (%): C,70.26; H,5.90; N,3.03; S,6.95
Found (%): C,70.25; H,5.92; N,3.08; S,6.94

EXAMPLE 36

Preparation of 3-[[2-acetylthiomethyl-3-(4-methoxyphenyl)propionyl]amino]benzoic acid sodium salt A mixture of 2-acetylthiomethyl-3-(4-methoxyphenyl)propionic acid (5 g), thionyl chloride (5 ml) and chloroform (50 ml) is refluxed for 30 minutes. The reaction mixture is concentrated under reduced pressure, and the residue is dissolved in tetrahydrofuran (50 ml). 3-Aminobenzoic acid (2.61 g) is suspended in water (20 ml) and the mixture is adjusted to pH 9.0 with 10% aqueous sodium hydroxide solution and thereto is added dropwise the above tetrahydrofuran solution. While maintaining pH 7.5–8.0 with 1 N aqueous sodium hydroxide solution, the mixture is stirred under ice cooling for 30 minutes and further at room temperature for one hour. Tetrahydrofuran is distilled off under reduced pressure, and the resulting aqueous solution is purified by a medium pressure column chromatography with CHP-20P (eluant, water-dioxane). The fractions containing the desired compound are collected and lyophilized to give the title compound (4.2 g).

m.p.: 161°–163° C. (amorphous)
IR (KBr; cm$^{-1}$): 1675, 1655
Elementary analysis for $C_{20}H_{20}NO_5SNa$: Calcd. (%): C,58.67; H,4.92; N,3.42; S,7.83; Na,5.62 Found (%): C,58.37; H,5.10; N,3.36; S,8.07; Na,5.78

EXAMPLE 37

Preparation of 3-[[2-acetylthiomethyl-3-(4-methoxyphenyl)propionyl]amino]benzoic acid 3-[[2-Acetylthiomethyl-3-(4 methoxyphenyl)-propionyl]amino]benzoic acid sodium salt (compound of Example 36) (1.5 g) is dissolved in water (30 ml), and the mixture is adjusted to pH 3.0 with 1 N hydrochloric acid with stirring under ice cooling, and the mixture is extracted with ethyl acetate (50 ml). The extract is washed with water and dried over anhydrous magnesium sulfate, and then distilled under reduced pressure to give the title compound (1.0 g).

m.p.: 124°–126° C. (amorphous)
IR (KBr; cm$^{-1}$): 1680, 1650
Elementary analysis for $C_{20}H_{21}NO_5S$: Calcd. (%): C,62.00; H,5.46; N,3.62; S,8.28 Found (%): C,61.98; H,5.44; N,3.47; S,8.48

EXAMPLE 38

Preparation of 3-[(2-acetylthiomethyl-5-phenylpentanoyl)amino]benzoic acid sodium salt A mixture of 2-acetylthiomethyl-5-phenylvaleric acid (5.5 g), thionyl chloride (6 ml) and chloroform (50 ml) is refluxed for one hour. The reaction mixture is concentrated under reduced pressure. The residue is dissolved in tetrahydrofuran (50 ml). 3-Aminobenzoic acid (2.9 g) is suspended in water (20 ml) and the mixture is adjusted to pH 9.0 with 10% aqueous sodium hydroxide solution. To the mixture is added dropwise the above tetrahydrofuran solution with stirring under ice cooling. While maintaining at pH 7.5 with 1 N aqueous sodium hydroxide solution, the mixture is stirred under ice cooling for 30 minutes and further at room temperature for one hour. Tetrahydrofuran is distilled off under reduced pressure, and the resulting aqueous solution is purified by a medium pressure column chromatography with CHP-20P (eluant, water-dioxane). The fractions containing the desired compound are collected and lyophilized to give the title compound (3.4 g).

m.p.: 150°–153° C. (amorphous)
IR (KBr; cm$^{-1}$): 1680, 1650
Elementary analysis for $C_{21}H_{23}NO_4SNa \cdot 0.25H_2O$:
Calcd. (%): C,61.08; H,5.74; N,3.39; S,7.76; Na,5.57
Found (%): C,60.91; H,5.58; N,3.42; S,7.85; Na,5.82

EXAMPLE 39

Preparation of 3-[(2-acetylthiomethyl-5-phenylpentanoyl)amino]benzoic acid

3-[(2-Acetylthiomethyl-5-phenylpentanoyl)amino]benzoic acid sodium salt (compound of Example 38) (1.5 g) is dissolved in water (30 ml), and the mixture is adjusted to pH 2.5 with 10% hydrochloric acid under ice cooling, and the mixture is extracted with ethyl acetate (50 ml). The extract is washed with water and dried over anhydrous magnesium sulfate, and then ethyl acetate is distilled off to give the title compound (1.1 g).

m.p.: 142°–145° C. (amorphous)
IR (KBr; cm$^{-1}$): 1680, 1650
Elementary analysis for $C_{21}H_{24}NO_4S$: Calcd. (%) C,65.26; H,6.26; N,3.62; S,8.30 Found (%): C,65.51; H,6.09; N,3.47; S,8.46

EXAMPLE 40

Preparation of 3-[[2-acetylthiomethyl-3-(4-fluorophenyl)propionyl]amino]benzoic acid sodium salt A mixture of 2-acetylthiomethyl-3-(4-fluorophenyl)propionic acid (5.7 g), thionyl chloride (6 ml) and chloroform (50 ml) is refluxed for one hour. The reaction mixture is concentrated under reduced pressure. The residue is dissolved in tetrahydrofuran (50 ml). 3-Aminobenzoic acid (3.05 g) is suspended in water (20 ml) and the mixture is adjusted to pH 9.0 with 10% aqueous sodium hydroxide solution. To the mixture is added dropwise the above tetrahydrofuran solution. While maintaining at pH 8.0 with 1 N aqueous sodium hydroxide solution, the mixture is stirred under ice cooling for 30 minutes and further at room temperature for one hour. Tetrahydrofuran is distilled off under reduced pressure, and the resulting aqueous solution is purified by a medium pressure column chromatography with CHP-20P (eluant, water-dioxane). The fractions containing the desired compound are collected and lyophilized to give the title compound (5.6 g).

m.p.: 155°–157° C. (amorphous)
IR (KBr; cm$^{-1}$): 1680, 1650
Elementary analysis for $C_{19}H_{17}FNO_4SNa.0.5H_2O$: Calcd. (%): C,56.15; H,4.46; F,4.67; N,3.45; S,7.89; Na,5.66 Found (%): C,55.91; H,4.67; F,4.61; N,3.38; S,7.98; Na,5.89

EXAMPLE 41

Preparation of 3-[[2-acetylthiomethyl-3-(4-fluorophenyl)propionyl]amino]benzoic acid 3-[[2-Acetylthiomethyl-3-(4-fluorophenyl)-propionyl]amino]benzoic acid sodium salt (compound of Example 40) (0.5 g) is dissolved in water (10 ml), and the mixture is adjusted to pH 2.5 with 1 N hydrochloric acid with stirring under ice cooling, and the mixture is extracted with ethyl acetate (20 ml). The extract is washed with water and dried over anhydrous magnesium sulfate, and then ethyl acetate is distilled off to give the title compound (0.4 g).

m.p.: 172°–174° C. (amorphous)
IR (KBr; cm$^{-1}$): 1680, 1640
Elementary analysis for $C_{19}H_{18}FNO_4S$: Calcd. (%): C,60.79; H,4.83; F,5.06; N,3.73; S,8.54 Found (%): C,60.75; H,4.89; F,5.09; N,3.64; S,8.49

EXAMPLE 42

Preparation of 3-[[2-mercaptomethyl-3-(4-methoxyphenyl)propionyl]amino]benzoic acid sodium salt 3-[[2-Acetylthiomethyl-3-(4-methoxyphenyl)-propionyl]amino]benzoic acid sodium salt (compound of Example 36) (2.0 g) is dissolved in water (20 ml), and the mixture is adjusted to pH 12.0 with 1 N aqueous sodium hydroxide solution under nitrogen. After reacting at room temperature for one hour, the reaction mixture is adjusted to pH 8.0 with 10% hydrochloric acid and is purified by a medium pressure column chromatography with CHP-20P (eluant, water-acetonitrile). The fractions containing the desired compound are collected, and acetonitrile is distilled off under reduced pressure and then lyophilized to give the title compound (0.7 g).

m.p.: 161°–163° C. (amorphous)
IR (KBr; cm$^{-1}$): 1650
Elementary analysis for $C_{18}H_{18}NO_4SNa.1.25H_2O$: Calcd. (%): C,55.45; H,5.30; N,3.59; S,8.22; Na,5.90 Found (%): C,55.40; H,5.06; N,3.61; S,8.69; Na,6.37

EXAMPLE 43

Preparation of 3-[[2-mercaptomethyl-3-(4-methoxyphenyl)propionyl]amino]benzoic acid 3-[[2-Acetylthiomethyl-3-(4-methoxyphenyl)-propionyl] amino]benzoic acid sodium salt (compound of Example 36) (1.8 g) is dissolved in water (30 ml), and the mixture is adjusted to pH 12.0 with 10% aqueous sodium hydroxide solution under nitrogen. After reacting at room temperature for one hour, the reaction mixture is adjusted to pH 2.5 with 10% hydrochloric acid. The mixture is extracted with ethyl acetate (50 ml). The extract is washed with water and ethyl acetate is distilled off. The residue is purified by a medium pressure column chromatography with CHP-20P (eluant, water-acetonitrile). The fractions containing the desired compound are collected, and acetonitrile is distilled off under reduced pressure and the residue is lyophilized to give the title compound (0.6 g).

m.p.: 184°–185° C. (amorphous)
IR (KBr; cm$^{-1}$): 1680, 1650
Elementary analysis for $C_{18}H_{19}NO_4S.H_2O$: Calcd. (%): C,59.49; H,5.82; N,3.85; S,8.82 Found (%): C,59.10; H,5.28; N,3.84; S,8.64

EXAMPLE 44

Preparation of 3-[[2-mercaptomethyl-3-(4-fluorophenyl)propionyl]amino]benzoic acid 3-[[2-Acetylthiomethyl-3-(4-fluorophenyl)-propionyl]amino]benzoic acid sodium salt (compound of Example 40) (1.2 g) is dissolved in water (20 ml), and the mixture is adjusted to pH 12.0 with 10% aqueous sodium hydroxide solution under nitrogen. After reacting at room temperature for one hour, the reaction mixture is adjusted to pH 2.5 with 10% hydrochloric acid. The mixture is extracted with ethyl acetate (50 ml). The extract is washed with water and ethyl acetate is distilled off. The residue is purified by a medium pressure column chromatography with CHP-20P (eluant, water-dioxane). The fractions containing the desired compound are collected and lyophilized to give the title compound (0.6 g).

m.p.: 180°–182° C. (amorphous)
IR (KBr; cm$^{-1}$): 1680, 1650
Elementary analysis for $C_{17}H_{16}FNO_3S$: Calcd. (%): C,61.25; H,4.84; F,5.70; N,4.20; S,9.62 Found (%): C,61.11; H,4.86; F,5.70; N,4.08; S,9.63

EXAMPLE 45

Preparation of 3-[[2-acetylthiomethyl-3-(4-dimethylaminophenyl)propionyl]amino]benzoic acid A mixture of 2-acetylthiomethyl-3-(4-dimethylaminophenyl)propionic acid (2.0 g), thionyl chloride (2 ml) and chloroform (20 ml) is refluxed for 30 minutes. The reaction mixture is concentrated under reduced pressure. The residue is dissolved in tetrahydrofuran (30 ml). 3-Aminobenzoic acid (1.1 g) is suspended in water (10 ml) and the mixture is adjusted to pH 9.0 with 10% aqueous sodium hydroxide solution. To the mixture is added dropwise the above tetrahydrofuran soltuion with stirring under ice cooling. While maintaining at pH 7.5–8.0 with 1 N aqueous sodium hydroxide solution, the mixture is stirred under ice cooling for 30 minutes and further at room temperature for one hour. Tetrahydrofuran is distilled off under reduced pressure, and the resulting aqueous solution is adjusted to pH 4.5 with 1 N hydrochloric acid and purified by a column chromatography with Diaion HP-20 (eluant, water-acetonitrile). The fractions containing the desired compound are collected, and acetonitrile is distilled off under reduced pressure, and the residue is extracted with ethyl acetate. The extract is dried over anhydrous magnesium sulfate, and ethyl acetate is distilled off to give the title compound (0.7 g).

m.p.: 71°–73° C. (amorphous)
IR (KBr; cm$^{-1}$): 1680, 1660
Elementary analysis for $C_{21}H_{24}N_2O_4S$: Calcd. (%): C,62.98; H,6.04; N,6.99; S,8.01 Found (%): C,62.65; H,6.21; N,6.96; S,8.08

EXAMPLE 46

Preparation of 3-[[2-acetylthiomethyl-3-(4-methylphenyl)propionyl]amino]benzoic acid In the same manner as described in Example 45, there is prepared the title compound.
m.p.: 174°–175° C. (amorphous)
IR (KBr; cm$^{-1}$): 1680, 1650
Elementary analysis for $C_{20}H_{21}NO_4S$: Calcd. (%): C,64.67; H,5.70; N,3.77; S,8.63 Found (%): C,64.66; H,5.79; N,3.76; S,8.46

EXAMPLE 47

Preparation of 3-[[2-acetylthiomethyl-3-(4-benzyl-2-morpholinyl)propionyl]amino]benzoic acid (a mixture of diastereomers)

In the same manner as described in Example 45, there is prepared the title compound.
m.p.: 103°–105° C. (amorphous)
IR (KBr; cm$^{-1}$): 1670, 1650
Elementary analysis for $C_{24}H_{28}N_2O_5S.0.25H_2O$: Calcd. (%): C,62.52; H,6.23; N,6.08; S,6.95 Found (%): C,62.60; H,6.26; N,6.08; S,6.64

EXAMPLE 48

Preparation of 3-[[2-acetylthiomethyl-3-(3-pyridyl)propionyl]amino]benzoic acid

In the same manner as described in Example 45, there is prepared the title compound.
m.p.: >200° C. (white needles)
IR (KBr; cm$^{-1}$): 1680, 1650
Elementary analysis for $C_{18}H_{18}N_2O_4S$: Calcd. (%): C,60.32; H,5.06; N,7.82; S,8.95 Found (%): C,59.98; H,5.09; N,8.01; S,8.85

EXAMPLE 49

Preparation of 3-[[2-acetylthiomethyl-3-(3-benzisoxazolyl)propionyl]amino]benzoic acid In the same manner as described in Example 45, there is prepared the title compound.
m.p.: 185°–187° C. (amorphous) (dissolving in water-dixane, followed by lyophilization)
IR (KBr; cm$^{-1}$): 1680, 1640
Elementary analysis for $C_{20}H_{18}N_2O_5S$: Calcd. (%) C,60.23; H,4.55; N,7.03; S,8.05 Found (%): C,60.28; H,4.62; N,6.85; S,7.75

EXAMPLE 50

Preparation of 3-[[2-acetylthiomethyl-3-(2,4-difluorophenyl)propionyl]amino]benzoic acid In the same manner as described in Example 45, there is prepared the title compound.
m.p.: 164°–166° C. (amorphous) (dissolving in water-dioxane, followed by lyophilization)
IR (KBr; cm$^{-1}$): 1680, 1650
Elementary analysis for $C_{19}H_{17}F_2NO_4S$: Calcd. (%): C,58.01; H,4.36; F,9.66; N,3.56; S,8.15 Found (%): C,58.24; H,4.40; F,9.58; N,3.47; S,8.04

EXAMPLE 51

Preparation of 3-[[2-mercaptomethyl-3-(4-dimethylaminophenyl)propionyl]amino]benzoic acid 3-[[2-Acetylthiomethyl-3-(4-dimethylaminophenyl)propionyl]amino]benzoic acid (compound of Example 45) (2.6 g) is dissolved in 50% aqueous methanol (30 ml), and the mixture is adjusted to pH 12.0 with 10% aqueous sodium hydroxide solution under nitrogen. After reacting at room temperature for one hour, the reaction mixture is adjusted to pH 4.5 with 10% hydrochloric acid, and methanol is distilled off. The resulting aqueous solution is purified by a medium pressure column chromatography with CHP-20P (eluant, water-acetonitrile). The fractions containing the desired compound are collected, and acetonitrile is distilled off and the residue is lyophilized to give the title compound (0.7 g).
m.p.: 91°–93° C. (amorphous)
IR (KBr; cm$^{-1}$): 1650
Elementary analysis for $C_{19}H_{22}N_2O_3S.0.25H_2O$: Calcd. (%): C,62.87; H,6.25; N,7.72; S,8.83 Found (%): C,62.60; H,6.27; N,7.57; S,9.02

EXAMPLE 52

Preparation of 3-[[2-mercaptomethyl-3-(4-methylphenyl)propionyl]amino]benzoic acid In the same manner as described in Example 51, there is prepared the title compound.
m.p.: 188°–190° C. (amorphous)
IR (KBr; cm$^{-1}$): 1680, 1650
Elementary analysis for $C_{18}H_{19}NO_3S$: Calcd. (%): C,65.63; H,5.81; N,4.25; S,9.73 Found (%): C,65.55; H,5.97; N,4.15; S,9.91

EXAMPLE 53

Preparation of 3-[[2-mercaptomethyl-3-(4-benzyl-2-morpholinyl)propionyl]amino]benzoic acid (a mixture of diastereomers)

3-[[2-Acetylthiomethyl-3-(4-benzyl-2-morpholinyl)propionyl]amino]benzoic acid (compound of Example 47) (1.0 g) is dissolved in 50% aqueous methanol (20 ml), and the mixture is adjusted to pH 12.0 with 10% aqueous sodium hydroxide solution under nitrogen. After reacting at room temperature for one hour, the reaction mixture is adjusted to pH 4.5 with 10% hydrochloric acid, and methanol is distilled off under reduced pressure. The residue is extracted with ethyl acetate, and the extract is washed with water and ethyl acetate is distilled off. The residue is purified by a medium pressure column chromatography with CHP-20P (eluant, water-acetonitrile). The fractions containing the desired compound are collected, and acetonitrile is distilled off under reduced pressure and the residue is lyophilized to give the title compound (0.3 g).
m.p. 110°–112° C. (amorphous)
IR (KBr; cm$^{-1}$): 1660
Elementary analysis for $C_{22}H_{27}N_2O_4S$: Calcd. (%): C,63.59; H,6.55; N,6.74; S,7.72 Found (%): C,63.22; H,6.52; N,6.50; S,7.74

EXAMPLE 54

Preparation of
3-[[2-mercaptomethyl-3-(3-pyridyl)-propionyl]amino]-benzoic acid

In the same manner as described in Example 51, there is prepared the title compound.
m.p.: 94°–97° C. (amorphous)
IR (KBr; cm$^{-1}$): 1680
Elementary analysis for $C_{16}H_{16}N_2O_3S$: Calcd. (%): C,60.74; H,5.10; N,8.85; S,10.13 Found (%): C,60.32; H,5.17; N,8.78; S,9.91

EXAMPLE 55

Preparation of
3-[(2-mercaptomethyl-5-phenylpentanoyl)amino] benzoic acid

In the same manner as described in Example 51, there is prepared the title compound.
m.p.: 134°–136° C. (amorphous) (dissolving in water-dioxane, followed by lyophilization)
IR (KBr; cm$^{-1}$): 1680, 1650
Elementary analysis for $C_{19}H_{21}NO_3S$: Calcd. (%): C,66.45; H,6.16; N,4.03; S,9.34 Found (%): C,66.60; H,6.27; N,3.99; S,9.20

EXAMPLE 56

Preparation of
3-[[2-mercaptomethyl-3-(3-benzisoxazolyl)propionyl]amino]benzoic acid In the same manner as described in Example 51, there is prepared the title compound.
m.p.: 207°–209° C. (amorphous) (lyophilization product)
IR (KBr; cm$^{-1}$): 1690, 1640
Elementary analysis for $C_{18}H_{16}N_2O_4S$: Calcd. (%): C,60.66; H,4.53; N,7.86; S,9.00 Found (%): C,60.92; H,4.72; N,7.56; S,8.84

EXAMPLE 57

Preparation of
3-[[2-mercaptomethyl-3-(2,4-difluorophenyl)propionyl]amino]benzoic acid In the same manner as described in Example 51, there is prepared the title compound.
m.p.: 168°–170° C. (amorphous)
IR (KBr; cm$^{-1}$): 1680, 1650
Elementary analysis for $C_{17}H_{15}F_2NO_3S$: Calcd. (%): C,58.11; H,4.30; F,3.99; N,9.13; S,10.81 Found (%): C,58.27; H,4.40; F,3.94; N,8.99; S,10.85

EXAMPLE 58

Preparation of
3-[[2-mercaptomethyl-3-(3-pyridyl)-propionyl]amino]-benzoic acid hydrochloride 3-[[2-Mercaptomethyl-3-(3-pyridyl)propionyl]-amino]benzoic acid (compound of Example 54) (0.2 g) is dissolved in ethanol (20 ml), and thereto is added 35% ethanolic hydrochloric acid (0.3 ml), and the mixture is stirred at room temperature for 5 minutes, and ethanol is distilled off under reduced pressure. To the residue is added diethyl ether (30 ml), and the mixture is cooled. The precipitated white powder is taken by filtration to give the title compound (0.15 g).
m.p.: 69°–71° C. (amorphous)
IR (KBr; cm$^{-1}$): 1660

Elementary analysis for $C_{16}H_{16}N_2O_3S.HCl.0.5H_2O$: Calcd. (%): C,53.11; H,5.01; Cl,9.80; N,8.86; S,7.74 Found (%): C,53.30; H,5.42; Cl,9.42; N,8.34; S,7.55

EXAMPLE 59

Preparation of
3-[[2-acetylthiomethyl-3-(4-dimethylaminophenyl)propionyl]amino]-5-methylbenzoic acid hydrochloride A mixture of 2-acetylthiomethyl-3-(4-dimethylaminophenyl]propionic acid (2.9 g), thionyl chloride (3 ml) and chloroform (30 ml) is refluxed for 30 minutes. The reaction mixture is concentrated under reduced pressure. The residue is dissolved in tetrahydrofuran (30 ml). 3-Amino-5-methylbenzoic acid (1.5 g) is suspended in water (10 ml) and the mixture is adjusted to pH 9.0 with 10% aqueous sodium hydroxide solution. To the mixture is added dropwise the above tetrahydrofuran soltuion with stirring under ice cooling. While maintaining at pH 7.5 with 1 N aqueous sodium hydroxide solution, the mixture is stirred under ice cooling for 30 minutes and further at room temperature for one hour. The mixture is adjusted to pH 4.5 with 10% hydrochloric acid, and tetrahydrofuran is distilled off under reduced pressure. The resulting aqueous solution is purified by a column chromatography with Diaion HP-20 (eluant, water-acetonitrile). The fractions containing the desired compound are collected, and acetonitrile is distilled off under reduced pressure, and the residue is lyophilized to give the title compound (1.9 g).
m.p.: 127°–128° C. (amorphous)
IR (KBr; cm$^{-1}$): 1680, 1640
Elementary analysis for $C_{22}H_{26}N_2O_4S.HCl.0.25H_2O$: Calcd. (%): C,58.01; H,6.09; Cl,7.78; N,6.15; S,7.04 Found (%): C,57.98; H,6.24; Cl,7.51; N,6.08; S,6.84

EXAMPLE 60

Preparation of
3-[[2-mercaptomethyl-3-(4-dimethylaminophenyl)propionyl]amino]-5-methylbenzoic acid hydrochloride 3-[[2-Acetylthiomethyl-3-(4-dimethylaminophenyl)-propionyl] amino]-5-methylbenzoic acid hydrochloride (compound of Example 59) (1.9 g) is dissolved in 50% aqueous methanol (30 ml), and the mixture is adjusted to pH 12.0 with 10% aqueous sodium hydroxide solution under nitrogen. After reacting at room temperature for one hour, the reaction mixture is adjusted to pH 4.5 with 10% hydrochloric acid and methanol is distilled off under reduced pressure. The residue is purified by a medium pressure column chromatography with CHP-20P (eluant, water-acetonitrile). The fractions containing the desired compound are collected, and acetonitrile is distilled off under reduced pressure and the residue is extracted with ethyl acetate. The extract is washed with water, dried over anhydrous magnesium sulfate, and ethyl acetate is distilled off under reduced pressure. To the residue is added 35% ethanolic hydrochloric acid (0.5 ml), and the mixture is cooled and thereto is added diethyl ether (50 ml). The pricipitated white powder is separated by filtration to give the title compound (0.85 g). m p.: 119°–121° C. (amorphous, decomp.)
IR (KBr; cm$^{-1}$): 1680, 1640
Elementary analysis for $C_{20}H_{24}N_2O_3S.HCl.0.5H_2O$: Calcd. (%): C,57.48; H,6.27; Cl,8.48; N,6.70; S,7.67 Found (%): C,57.64; H,6.28; Cl,8.25; N,6.49; S,7.89

EXAMPLE 61

Preparation of benzyl 3-[[2-acetylthiomethyl-3-(4-dimethylaminophenyl)propionyl]amino]benzoate hydrochloride (1) Preparation of 3-(t-Butyloxycarbonylamino)-benzoic acid 3-Aminobenzoic acid (13.7 g) is mixed with water (100 ml), and the mixture is adjusted to pH 9.5 with 20% aqueous sodium hydroxide solution. To the mixture is added a solution of di-t-butyl dicarbonate (25 g) in dioxane (80 ml) with stirring under ice cooling. The mixture is stirred under ice cooling for 30 minutes and further at room temperature for 4 hours. The reaction mixture is washed with ethyl acetate (200 ml). The aqueous solution is adjusted to pH 5.0 with citric acid, and the precipitated crystals are separated by filtration and recrystallized from acetonitrile to give the title compound (22.1 g, 93%) as white needles.

m.p.: 205° C. (decomp.)
IR (KBr; cm$^{-1}$): 1680
Elementary analysis for $C_{12}H_{15}NO_4$: Calcd. (%): C,60.75; H,6.37; N,5.90 Found (%): C,60.69; H,6.49; N,5.87

(2) Preparation of cyanomethyl 3-(t-butyloxy-carbonylamino)benzoate

A mixture of 3-(t-butyloxycarbonylamino)benzoic acid (20 g), triethylamine (12.8 g), chloroacetonitrile (9.4 g) and acetone (150 ml) is refluxed for 4 hours. After acetone is distilled off under reduced pressure, the residue is dissolved in ethyl acetate (200 ml), and the solution is washed with water, and ethyl acetate is distilled off under reduced pressure. The residue is recrystallized from 80% aqueous acetonitrile solution to give the title compound (22 g, 99%) as white short needles.

m.p.: 118°-119° C.
IR (KBr; cm$^{-1}$): 1705
Elementary analysis for $C_{14}H_{16}N_2O_4$: Calcd. (%): C,60.86; H,5.84; N,10.14 Found (%): C,60.88; H,5.82; N,10.11

(3) Preparation of benzyl 3-(t-butyloxycarbonylamino)benzoate

A mixture of cyanomethyl 3-(t-butyloxycarbonylamino)benzoate (20 g), triethylamine (10.6 g), 4-dimethylaminopyridine (0.1 g) and benzyl alcohol (11.4 g) is stirred at a bath temperature of 55° C. for 15 hours. The reaction mixture is extracted with ethyl acetate (200 ml), and the extract is washed with water, and ethyl acetate is distilled off under reduced pressure. The residue is recrystallized from 80% aqueous acetonitrile solution to give the title compound (22.0 g, 93%) as white short needles.

m.p.: 151°-153° C.
IR (KBr; cm$^{-1}$): 1710, 1690
Elementary analysis for $C_{19}H_{22}NO_4$: Calcd. (%): C,69.49; H,6.75; N,4.27 Found (%): C,69.49; H,6.46; N,4.25

(4) Preparation of benzyl 3-[[2-acetylthiomethyl-3-(4-dimethylaminophenyl)propionyl]amino]benzoate hydrochloride A mixture of 2-acetylthiomethyl-3-(4-dimethylaminophenyl)propionic acid (3.0 g), thionyl chloride (3 ml) and chloroform (30 ml) is refluxed for 30 minutes. The reaction mixture is concentrated under reduced pressure. The residue is dissolved in chloroform (30 ml).

Separately, benzyl 3-(t-butyloxycarbonylamino)-benzoate (3.9 g) is mixed with trifluoroacetic acid (3 ml), and the mixture is stirred at room temperature for 30 minutes. The reaction mixture is concentrated under reduced pressure, and the residue is dissolved in chloroform (20 ml), and thereto is added dropwise the above solution of acid chloride in chloroform with stirring under ice cooling. The mixture is neutralized with triethylamine and stirred under ice cooling for 30 minutes and further at room temperature for one hour. The reaction mixture is washed with water, dried over anhydrous magnesium sulfate, and chloroform is distilled off under reduced pressure. The residue is purified by a silica gel column chromatography (eluant, chloroform-ethyl acetate). The fractions containing the desired compound are collected and concentrated under reduced pressure. To the residue are added 35% ethanolic hydrochloric acid (0.5 ml) and further diethyl ether (50 ml), and the mixture is filtered. The obtained powder is washed with diethyl ether to give the title compound (1.5 g).

m.p.: 73°-75° C. (amorphous)
IR (KBr; cm$^{-1}$): 1700, 1670
Elementary analysis for $C_{28}H_{30}N_2O_4S \cdot HCl$: Calcd. (%) C,63.81; H,5.93; Cl,6.73; N,5.31; S,6.08 Found (%): C,63.79; H,5.99; Cl,7.03; N,5.31; S,6.06

EXAMPLE 62

Preparation of benzyl 3-[[2-acetylthiomethyl-3-(3-pyridyl)propionyl]amino]-benzoate Benzyl 3-(t-butyloxycarbonylamino)benzoate (4.9 g) is mixed with trifluoroacetic acid (5 ml), and the mixture is stirred at room temperature for 30 minutes. Excess trifluoroacetic acid is distilled off under reduced pressure. The residue is dissolved in chloroform (40 ml), and thereto are added 2-acetylthiomethyl-3-(3-pyridyl)-propionic acid (3.5 g) and EDC.HCl (3.2 g), and the mixture is stirred at room temperature for 5 hours. The reaction mixture is washed with water, dried over anhydrous magnesium sulfate, and then chloroform is distilled off under reduced pressure. The residue is purified by a silica gel column chromatography (eluant, chloroform-ethyl acetate). The fractions containing the desired compound are collected and the solvent is distilled off under reduced pressure to give the title compound (1.5 g) as a colorless oily substance.

IR (KBr; cm$^{-1}$): 1710, 1680
Elementary analysis for $C_{25}H_{24}N_2O_4S$: Calcd. (%): C,66.79; H,5.61; N,6.23; S,7.13 Found (%): C,66.30; H,5.53; N,6.15; S,7.21

EXAMPLE 63

Preparation of benzyl 3-[(2-mercaptomethyl-3-phenylpropionyl)amino]benzoate

Benzyl 3-[(2-acetylthiomethyl-3-phenylpropionyl)-amino]benzoate (2.0 g) is dissolved in acetonitrile (20 ml), and thereto is added 28% aqueous ammonia (15 ml), and the mixture is stirred at room temperature for one hour. The reaction mixture is adjusted to pH 2.5 with 20% hydrochloric acid under ice cooling and is extracted with ethyl acetate (70 ml). The extract is washed with water, and ethyl acetate is distilled off under reduced pressure. The residue is purified by a medium pressure column chromatography with CHP-20P (eluant, water-acetonitrile). The fractions containing the desired compound are collected, and acetonitrile is distilled off under reduced pressure and the residue is extracted with ethyl acetate (100 ml). The extract is dried over anhydrous magnesium sulfate, and ethyl acetate is distilled off under reduced pressure to give the title compound (0.9 g) as a colorless oily substance.

IR (KBr; cm$^{-1}$): 1710, 1660

Elementary analysis for $C_{24}H_{23}NO_3S.0.25H_2O$: Calcd. (%): C,70.30; H,5.78; N,3.42; S,7.82 Found (%) C,70.59; H,5.92; N,3.32; S,7.93

EXAMPLE 64

Preparation of 3-[(2-acetylthiomethyl-3-phenylpropionyl)amino]-5-ethylbenzoic acid 3-Amino-5-ethylbenzoic acid (2.1 g) is dissolved in a 33% aqueous solution of tetrahydrofuran (30 ml) containing sodium carbonate (1.3 g), and to the mixture is added dropwise a solution of 2-acetylthiomethyl-3-phenylpropionyl chloride (3.0 g) in tetrahydrofuran (20 ml) with stirring under ice cooling, and the mixture is stirred at room temperature for one hour. Tetrahydrofuran is distilled off under reduced pressure, and the residue is extracted with ethyl acetate (100 ml). The extract is washed with saturated aqueous sodium chloride solution and dried over anhydrous sodium sulfate, and then ethyl acetate is distilled off under reduced pressure. The residue is dissolved in methanol and purified by a medium pressure column chromatography with CHP-20P (eluant, water-methanol). The fractions containing the desired compound are collected and concentrated into dryness under reduced pressure to give the title compound (2.8 g).

m.p.: 175°-177° C. (amorphous)

IR (KBr; cm$^{-1}$): 1680, 1650

Elementary analysis for $C_{21}H_{23}NO_4S$: Calcd. (%): C,65.43; H,6.01; N,3.63; S,8.32 Found (%): C,65.44; H,5.98; N,3.68; S,8.09

EXAMPLE 65

Preparation of 3-[(2-mercaptomethyl-3-phenylpropionyl)amino]-5-ethylbenzoic acid 3-[(2-Acetylthiomethyl-3-phenylpropionyl)amino]-5-ethylbenzoic acid (compound of Example 64) (1.0 g) is suspended in water (10 ml), and thereto is added pyrrolidine (0.6 g) under nitrogen, and the mixture is stirred at room temperature for 20 minutes. The reaction mixture is adjusted to pH 1 with conc. hydrochloric acid and is extracted with ethyl acetate (100 ml). The extract is washed with saturated aqueous sodium chloride solution, dried over sodium sulfate, and ethyl acetate is distilled off under reduced pressure. The residue is dissolved in methanol and purified by a medium pressure column chromatography with CHP-20P (eluant, water-methanol). The fractions containing the desired compound are collected and concentrated into dryness to give the title compound (0.3 g).

m.p.: 159°-160° C. (amorphous)

IR (KBr; cm$^{-1}$): 1680, 1640

Elementary analysis for $C_{19}H_{21}NO_3S$: Calcd. (%): C,66.45; H,6.16; N,4.08; S,9.34 Found (%): C,66.20; H,6.09; N,4.01; S,9.45

EXAMPLE 66

Preparation of 3-[(2-acetylthiomethyl-3-phenylpropionyl)amino]-5-isopropylbenzoic acid In the same manner as described in Example 64 except that 3-amino-5-isopropylbenzoic acid is used, there is prepared the title compound.

m.p.: 205°-206° C. (amorphous)

IR (KBr; cm$^{-1}$): 1680, 1650

Elementary analysis for $C_{22}H_{25}NO_4S$: Calcd. (%): C,66.14; H,6.31; N,3.51; S,8.03 Found (%): C,66.09; H,6.27; N,3.50; S,7.99

EXAMPLE 67

Preparation of 3-[(2-mercaptomethyl-3-phenylpropionyl)amino]-5-isopropylbenzoic acid In the same manner as described in Example 65, there is prepared the title compound.

m.p.: 205°-209° C. (amorphous)

IR (KBr; cm$^{-1}$): 1680, 1650

Elementary analysis for $C_{20}H_{23}NO_3S$: Calcd. (%) C,67.20; H,6.49; N,3.92; S,8.97 Found (%): C,67.07; H,6.48; N,3.87; S,8.80

EXAMPLE 68

Process a

[1] Preparation of ethyl 3-[(2-acetylthiomethyl-3-phenylpropionyl)amino]benzoate 2-Acetylthiomethyl-3-phenylpropionic acid (11.9 g) and ethyl 3-aminobenzoate (8.26 g) are dissolved in dichloromethane (150 ml), and thereto are added 4-dimethylaminopyridine (0.61 g) and EDC.HCl (10.54 g), and the mixture is stirred at room temperature overnight. The reaction mixture is washed with saturated aqueous citric acid solution, saturated aqueous sodium chloride solution and saturated aqueous sodium hydrogen carbonate solution and saturated aqueous sodium chloride solution in this order, dried over anhydrous magnesium sulfate, and the solvent is distilled off under reduced pressure. The residue is washed with diethyl ether to give the title compound (13 g).

m.p.: 89°-92° C. (amorphous),

IR (KBr; cm$^{-1}$): 1710, 1690, 1660

Elementary analysis for $C_{21}H_{23}NO_4S$: Calcd. (%): C,65.43; H,6.01; N,3.63; S,8.32 Found (%): C,65.42; H,6.14; N,3.55; S,8.19

[2] Preparation of 3-[(2-mercaptomethyl-3-phenylpropionyl)amino]benzoic acid

Ethyl 3-[(2-acetylthiomethyl-3-phenylpropionyl)amino]benzoate (6.37 g) is dissolved in methanol (100 ml), and thereto is added 1 N aqueous sodium hydroxide solution (49.5 ml) under ice cooling, and the mixture is stirred for 2 hours under nitrogen. After stirring further at room temperature overnight, the reaction mixture is acidified with saturated aqueous citric acid solution, and methanol is distilled off under reduced pressure. To the residue is added water (50 ml), and the mixture is extracted with ethyl acetate. The extract is washed with saturated aqueous sodium chloride solution, dried over anhydrous magnesium sulfate, and the solvent is distilled off under reduced pressure. The residue is purified by a medium pressure column chromatography with CHP-20P (eluant, water-acetonitrile). The fractions containing the desired compound are collected and concentrated under reduced pressure, and the precipitates are separated by filtration to give the title compound (4 g).

m.p.: 178°–180° C. (amorphous)
IR (KBr; cm$^{-1}$): 1680, 1655
Elementary analysis for $C_{17}H_{17}NO_3S$: Calcd. (%): C,64.74; H,5.43; N,4.44; S,10.17 Found (%): C,64.43; H,5.44; N,4.50; S,9.91

EXAMPLE 68

Process b

[1] Preparation of 3-[(2-acetylthiomethyl-3-phenylpropionyl)amino]benzoic acid

3-Aminobenzoic acid (1.4 g) is suspended in chloroform (50 ml), and thereto is added triethylamine (2.06 g), and to the mixture is added 2-acetylthiomethyl-3-phenylpropionyl chloride (2.61 g) with stirring under ice cooling, and the mixture is stirred for 30 minutes and further at room temperature three nights. To the reaction mixture is added water, and the mixture is acidified with hydrochloric acid and extracted with chloroform. The extract is washed with saturated aqueous sodium chloride solution, dried over anhydrous magnesium sulfate, and the solvent is distilled off under reduced pressure. The residue is purified by a medium pressure column chromatography with CHP-20P (eluant, water-acetonitrile). The fractions containing the desired compound are collected and concentrated under reduced pressure. The precipitates are separated by filtration and recrystallized from 50% aqueous ethanol to give the title compound (1.5 g).

m.p.: 172°–173° C.
IR (KBr; cm$^{-1}$): 1680, 1650
Elementary analysis for $C_{19}H_{19}NO_4S$: Calcd. (%): C,63.85; H,5.36; N,3.92; S,8.97 Found (%): C,63.59; H,5.46; N,3.91; S,9.05

[2] Preparation of 3-[(2-mercaptomethyl-3-phenylpropionyl)amino]benzoic acid

In the same manner as described in Example 68-(a)-[2] except that 3-[(2-acetylthiomethyl-3-phenylpropionyl)amino]benzoic acid is used, there is prepared the title compound.

EXAMPLE 69

Preparation of ethyl 4-[(2-acetylthiomethyl-3-phenylpropionyl)amino]benzoate

In the same manner as described in Example 68-(a)-[1] except that ethyl 4-aminobenzoate is used instead of ethyl 3-aminobenzoate, the reaction is carried out, and the product is purified by a silica gel column chromatography and a medium pressure column chromatography using CHP-20P to give the title compound.

m.p.: 119°–121° C. (amorphous)
IR (KBr; cm$^{-1}$): 1710, 1680, 1660
Elementary analysis for $C_{21}H_{23}NO_4S$: Calcd. (%): C,65.43; H,6.01; N,3.63; S,8.32 Found (%): C,65.27; H,6.01; N,3.58; S,8.14

EXAMPLE 70

Preparation of 4-[(2-mercaptomethyl-3-phenylpropionyl)amino]benzoic acid

In the same manner as described in Example 68-(a)-[2] except that ethyl 4-[(2-acetylthiomethyl-3-phenyl propionyl)amino]benzoate (compound of Example 69) is used, there is prepared the title compound.

m.p.: 181°–183° C. (amorphous)
IR (KBr; cm$^{-1}$): 1675, 1660 (shoulder)
Elementary analysis for $C_{17}H_{17}NO_3S$: Calcd. (%): C,64.74; H,5.43; N,4.44; S,10.17 Found (%): C,64.63; H,5.36; N,4.27; S,10.05

EXAMPLE 71

Preparation of 4-[(2-acetylthiomethyl-3-phenylpropionyl)amino]benzoic acid

In the same manner as described in Example 68-(b)-[1] except that 4-aminobenzoic acud is used instead of 3-aminobenzoic acid, there is prepared the title compound.

m.p.: 187°–189° C. (recrystallized from 70% aqueous ethanol)
IR KBr; cm$^{-1}$): 1660
Elementary analysis for $C_{19}H_{19}NO_4S$: Calcd. (%): C,63.85; H,5.36; N,3.92; S,8.97 Found (%): C,63.59; H,5.35; N,3.77; S,9.01

EXAMPLE 72

Preparation of benzyl 3-[(2-acetylthiomethyl-3-phenylpropionyl)amino]benzoate

3-[(2-Acetylthiomethyl-3-phenylpropionyl)amino]benzoic acid prepared in Example 68-(b)-[1] (0.3 g), 4-dimethylaminopyridine (0.01 g) and benzyl alcohol (0.1 g) are dissolved in dichloromethane (25 ml), and thereto is added EDC.HCl (0.18 g), and the mixture is stirred at room temperature three nights. The reaction mixture is washed with saturated aqueous citric acid solution, water, saturated aqueous sodium hydrogen carbonate solution and water in this order, dried over anhydrous magnesium sulfate, and then the solvent is distilled off under reduced pressure. The residue is purified by a silica gel column chromatography (eluant, chloroform) to give the title compound (0.26 g).

m.p.: 108°–109° C. (amorphous)
IR (KBr; cm$^{-1}$): 1720, 1680, 1655
Elementary analysis for $C_{26}H_{25}NO_4S$: Calcd. (%): C,69.78; H,5.63; N,3.13; S,7.16 Found (%) C,69.74; H,5.51; N,3.09; S,7.06

EXAMPLE 73

Preparation of benzyl 4-[(2-acetylthiomethyl-3-phenylpropionyl)amino]benzoate

4-[(2-Acetylthiomethyl-3-phenylpropionyl)amino]benzoic acid prepared in Example 71 is reacted in the same manner as described in Example 72 to give the title compound.

m.p.: 139°–140° C. (amorphous)
IR (KBr; cm$^{-1}$): 1710, 1685, 1660
Elementary analysis for $C_{26}H_{25}NO_4S$: Calcd. (%) C,69.78; H,5.63; N,3.13; S,7.16 Found (%): C,69.48; H,5.45; N,3.04; S,6.99

EXAMPLE 74

Preparation of benzyl 1-[(2-acetylthiomethyl-3-phenylpropionyl)amino]cyclohexanecarboxylate Benzyl 1-aminocyclohexanecarboxylate.p-toluenesulfonate and 2-acetylthiomethyl-3-phenylpropionic acid are reacted in the same manner as described in Example 68-(a)-[1] to give the title compound.

m.p.: 166°-168° C. (amorphous)
IR (KBr; cm$^{-1}$): 1710, 1680, 1660
Elementary analysis for $C_{26}H_{31}NO_4S$: Calcd. (%): C,68.85; H,6.89; N,3.09; S,7.07 Found (%): C,68.63; H,6.74; N,2.92; S,7.13

EXAMPLE 75

Preparation of benzyl 1-[(2-acetylthiomethyl-3-phenylpropionyl)amino]cyclopentanecarboxylate In the same manner as described in Example 74, the reaction is carried out and subjected to the post-treatment, and the product is washed with diisopropyl ether to give the title compound.

m.p.: 96°-100° C. (amorphous)
IR (KBr; cm$^{-1}$): 1705, 1680, 1660
Elementary analysis for $C_{25}H_{29}NO_4S.0.25H_2O$: Calcd. (%): C,67.62; H,6.70; N,3.15; S,7.22 Found (%): C,67.80; H,6.95; N,3.31; S,7.49

EXAMPLE 76

Preparation of benzyl 3-[(2-acetylthiomethyl-3-phenylpropionyl)amino]cyclohexanecarboxylate In the same manner as described in Example 74, the reaction is carried out and subjected to the post-treatment, and the product is washed with diisopropyl ether to give the title compound.

m.p.: 68°-71° C. (amorphous)
IR (KBr; cm$^{-1}$): 1715, 1680, 1630
Elementary analysis for $C_{26}H_{31}NO_4S.0.25H_2O$: Calcd. (%): C,68.17; H,6.93; N,3.06; S,7.00 Found (%) C,68.25; H,7.14; N,3.33; S,7.13

EXAMPLE 77

Preparation of 4-[(2-acetylthiomethyl-3-phenylpropionyl)aminomethyl]benzoic acid 4-Aminomethylbenzoic acid (1.50 g) and sodium hydrogen carbonate (1.68 g) are suspended in water (20 ml), and thereto is added dropwise a solution of 2-acetylthiomethyl-3-phenylpropionyl chloride (2.86 g) in tetrahydrofuran (6 ml) with vigorously stirring. After the reaction is completed, the reaction mixture is acidified with hydrochloric acid and is extracted with ethyl acetate. The extract is dried over anhydrous magnesium sulfate, and then the solvent is distilled off under reduced pressure. The residue is recrystallized from ethanol to give the title compound (1.2 g).

m.p.: 186°-188° C.
IR (KBr; cm$^{-1}$): 1680, 1640, 1610
Elementary analysis for $C_{20}H_{21}NO_4S.0.25H_2O$: Calcd. (%): C,63.90; H,5.76; N,3.73; S,8.53 Found (%): C,64.18; H,5.67; N,3.65; S,8.17

EXAMPLE 78

Preparation of 1-[(2-mercaptomethyl-3-phenylpropionyl)amino]cyclohexanecarboxylic acid In the same manner as described in Example 68-(a)-[2], the reaction is carried out to give the title compound.

m.p.: 193°-195° C. (amorphous)
IR (KBr; cm$^{-1}$): 1690, 1630
Elementary analysis for $C_{17}H_{23}NO_3S$: Calcd. (%): C,63.52; H,7.21; N,4.36; S,9.98 Found (%): C,63.33; H,7.00; N,4.18; S,9.91

EXAMPLE 79

Preparation of 1-[(2-mercaptomethyl-3-phenylpropionyl)amino]cyclopentanecarboxylic acid In the same manner as described in Example 68-(a)-[29, the reaction is carried out to give the title compound.

m.p.: 165°-167° C. (amorphous)
IR (KBr; cm$^{-1}$): 1685, 1625
Elementary analysis for $C_{16}H_{21}NO_3S$: Calcd. (%): C,62.51; H,6.89; N,4.56; S,10.43 Found (%) C,62.44; H,6.79; N,4.32; S,10.18

EXAMPLE 80

Preparation of 3-[(2-mercaptomethyl-3-phenylpropionyl)amino]cyclohexanecarboxylic acid In the same manner as described in Example 68-(a)-[2], the reaction is carried out to give the title compound.

m.p.: 174°-177° C. (amorphous)
IR (KBr: cm$^{-1}$): 1690, 1615
Elementary analysis for $C_{17}H_{23}NO_3S$: Calcd. (%): C,63.52; H,7.21; N,4.39; S,9.98 Found (%) C,63.39; H,7.25; N,4.31; S,9.90

EXAMPLE 81

Preparation of 2-[(2-acetylthiomethyl-3-phenylpropionyl)amino]benzoic acid

Methyl anthranylate (7.6 g , 2-benzylacrylic acid (8.1 g), HOBt (6.75 g), DCC (10.3 g) and DMF (150 ml) are mixed at room temperature, and the mixture is stirred for 4 hours, and the insoluble materials are filtered off. The filtrate is distilled under reduced pressure to remove the solvent, and to the residue is added ethyl acetate (150 ml). The mixture is washed with 5% hydrochloric acid, water, saturated aqueous sodium hydrogen carbonate solution and water in this order and dried over anhydrous magnesium sulfate, and then the solvent is distilled off under reduced pressure. The residue is subjected to a silica gel column chromatography. The fractions eluted with chloroform-n-hexane (1:1) are collected, and the solvent is distilled off under reduced pressure to give methyl 2-[(2-benzylacryl)amino]benzoate (3.4 g) as a yellow oily substance.

This product is dissolved in 50% aqueous methanol (50 ml) and the mixture is maintained at pH 12.0 with 15% aqueous sodium hydroxide solution at 40° C. for 30 minutes, and then methanol is distilled off under reduced pressure. The residue is adjusted to pH 2.0 with hydrochloric acid, and the precipitated white solid is separated by filtration and washed with water and recrystallized from 70% aqueous ethanol to give 2-[(2-benzylacryl)amino]benzoic acid (2.0 g) as colorless needles. This product (1.7 g) is mixed with thioacetic acid (0.9 g), and the mixture is stirred at 80° C. for one hour. Excess thioacetic acid is distilled off under reduced pressure, and to the residue is added water (30 ml). The mixture is adjusted to pH 8.0 with 10% aqueous sodium hydroxide solution under ice cooling and subjected to a column chromatography with Diaion HP-20. The fractions eluted with 5% aqueous dioxane are collected and lyophilized. The resulting colorless powder is dissolved in water (30 ml) and adjusted to pH 2.0 with hydrochloric acid under cooling. The precipitated oily substance is extracted with ethyl acetate, and the extract is washed with water, dried over anhydrous magnesium sulfate, and the solvent is distilled off under reduced pressure. The residue is recrystallized from 70% aqueous ethanol to give the title compound (0.9 g).

m.p.: 121°–122° C.
IR (KBr; cm$^{-1}$): 1660
Elementary analysis for $C_{19}H_{19}NO_4S$: Calcd. (%): C,63.85; H,5.36; N,3.92; S,8.97 Found (%): C,63.76; H,5.36; N,3.90; S,8.71

EXAMPLE 82

Preparation of benzyl 2-[(2-acetylthiomethyl-3-phenylpropionyl)amino]isobutyrate In the same manner as described in Example 68-(a)-[1], the reaction is carried out to give the title compound (2.16 g).

m.p.: 83°–85° C. (amorphous)
IR (KBr; cm$^{-1}$): 1735, 1685, 1635
Elementary analysis for $C_{23}H_{27}NO_4S$: Calcd. (%): C,66.80; H,6.58; N,3.39; S,7.75 Found (%): C,66.75; H,6.70; N,3.28; S,8.04

EXAMPLE 83

Preparation of 2-[(2-mercaptomethyl-3-phenylpropionyl)amino]isobutyric acid

The compound prepared in Example 82 is treated in the same manner as described in Example 68-(a)-[2], and the residue is purified by a medium pressure column chromatography with CHP-20P (eluant, water-acetonitrile). The fractions containing the desired compound are collected and concentrated under reduced pressure. The concentrated mixture is acidified with hydrochloric acid and extracted with ethyl acetate. The extract is washed with saturated aqueous sodium chloride solution, dried over anhydrous magnesium sulfate, and the solvent is distilled off under reduced pressure to give the title compound.

m.p.: 175°–176° C. (amorphous)
IR (KBr; cm$^{-1}$): 1700, 1640
Elementary analysis for $C_{14}H_{19}NO_3S$: Calcd. (%): C,59.76; H,6.81; N,4.98; S,11.40 Found (%): C,59.73; H,6.96; N,4.81; S,11.22

EXAMPLE 84

Preparation of benzyl 2-[(2-mercaptomethyl-3-phenylpropionyl)amino]isobutyrate

Benzyl 2-[(2-acetylthiomethyl-3-phenylpropionyl)amino]isobutyrate (0.45 g) is dissolved in a mixture of methanol (5 ml) and water (3 ml) under nitrogen, and thereto is added triethylamine (0.22 g), and the mixture is stirred at room temperature for 5 hours. After the reaction, the reaction mixture is acidified with saturated aqueous citric acid solution, and methanol is distilled off under reduced pressure. To the residue is added water, and the mixture is extracted with chloroform. The extract is washed with water and dried over anhydrous magnesium sulfate, and then distilled under reduced pressure. The residue is purified by a silica gel column chromatography (eluant, chloroform) to give the title compound (0.35 g).

m.p.: 53°–56° C. (amorphous)
IR (KBr; cm$^{-1}$): 1715, 1655
Elementary analysis for $C_{21}H_{25}NO_3S$: Calcd. (%) C,67.90; H,6.78; N,3.77; S,8.63 Found (%): C,68.00; H,7.07; N,3.67; S,8.45

EXAMPLE 85

Preparation of 4-[(2-mercaptomethyl-3-phenylpropionyl)aminomethyl]benzoic acid

In the same manner as described in Example 68-(b)-[2], the reaction is carried out to give the title compound.

m.p.: 156°–159° C. (amorphous)
IR (KBr; cm$^{-1}$): 1690, 1635
Elementary analysis for $C_{18}H_{19}NO_3S$: Calcd. (%): C,65.63; H,5.81; N,4.25; S,9.73 Found (%): C,65.55; H,5.95; N,4.27; S,9.73

EXAMPLE 86

Preparation of benzyl 4-[(2-acetylthiomethyl-3-phenylpropionyl)aminomethyl]benzoate In the same manner as described in Example 72, the reaction is carried out to give the title compound.

m.p.: 142°–143° C. (recrystallized from acetonitrile)
IR (KBr; cm$^{-1}$): 1705, 1675, 1640
Elementary analysis for $C_{27}H_{27}NO_4S$: Calcd. (%): C,70.26; H,5.90; N,3.03; S,6.95 Found (%): C,70.25; H,5.88; N,3.22; S,6.94

EXAMPLE 87

Preparation of solid solution of 3-[(2-mercaptomethyl-3-phenylpropionyl)amino]benzoic acid with glycine 3-[(2-Mercaptomethyl-3-phenylpropionyl)amino]benzoic acid (compound of Example 68) (0.77 g) is dissolved in dioxane (removing peroxide by passing through a neutral alumina column) (60 ml), and thereto is added a solution of glycine (0.18 g) in water (30 ml), and the mixture is lyophilized to give the title compound (0.95 g).

m.p.: 177°–181° C. (amorphous)
IR (KBr; cm$^{-1}$): 1675, 1655
Elementary analysis for $C_{17}H_{17}NO_3S \cdot C_2H_5NO_2$: Calcd. (%): C,58.45; H,5.68; N,7.17; S,8.21 Found (%): C,58.12; H,5.92; N,7.10; S,7.99

EXAMPLE 88

Preparation of solid solution of 3-[(2-mercaptomethyl-3-phenylpropionyl)amino]benzoic acid with L-phenylalanine In the same manner as described in Example 87 except that L-phenylalanine is used instead of glycine, there is prepared the title compound.

m.p.: 162°–165° C. (amorphous)

IR (KBr; cm$^{-1}$): 1680, 1650
Elementary analysis for $C_{17}H_{17}NO_3S.C_9H_{11}NO_2.0.75H_2O$: Calcd. (%): C,63.20; H,6.02; N,5.67; S,6.49 Found (%): C,63.36; H,5.84; N,5.50; S,6.35

EXAMPLE 89

Preparation of solid solution of 3-[(2-mercaptomethyl-3-phenylpropionyl)amino]benzoic acid with D-phenylalanine In the same manner as described in Example 87 except that D-phenylalanine is used instead of glycine, there is prepared the title compound.
m.p.: 162°-165° C. (amorphous)
IR (KBr; cm$^{-1}$): 1680, 1650
Elementary analysis for $C_{17}H_{17}NO_3S.C_9H_{11}NO_2.0.5-H_2O$: Calcd. (%): C,63.79; H,5.97; N,5.72; S,6.55 Found (%): C,63.53; H,5.81; N,5.54; S,6.25

EXAMPLE 90

Preparation of solid solution of 3-[(2-mercaptomethyl-3-phenylpropionyl)amino]benzoic acid with L-leucine In the same manner as described in Example 87 except that L-leucine is used instead of glycine, there is prepared the title compound.
m.p.: 169°-173° C. (amorphous)
IR (KBr; cm$^{-1}$): 1680, 1650
Elementary analysis for $C_{17}H_{17}NO_3S.C_6H_{13}NO_2.0.25H_2O$: Calcd. (%): C,61.24; H,6.82; N,6.21; S,7.11 Found (%): C,61.04; H,6.68; N,6.08; S,6.71

EXAMPLE 91

Preparation of 3-[(2-mercaptomethyl-3-phenylpropionyl)amino]benzoic acid L-lysine salt In the same manner as described in Example 87 except that L-lysine is used instead of glycine, there is prepared the title compound.
m.p.: 130°-133° C. (amorphous)
IR (KBr; cm$^{-1}$): 1650, 1600
Elementary analysis for $C_{17}H_{17}NO_3S.C_6H_{14}N_2O_2.0.25H_2O.0.25dioxane$: Calcd. (%): C,59.06; H,6.92; N,8.61; S,6.57 Found (%): C,59.01; H,7.25; N,8.72; S,6.80

EXAMPLE 92

Preparation of solid solution of 3-[(2-mercaptomethyl-3-phenylpropionyl)amino]benzoic acid with L-asparagine In the same manner as described in Example 87 except that L-asparagine is used instead of glycine, there is prepared the title compound.
m.p.: 168°-173° C. (amorphous)
IR (KBr; cm$^{-1}$): 1690, 1670, 1650
Elementary analysis for $C_{17}H_{17}NO_3S.C_4H_8N_2O_3.0.5-H_2O.0.25dioxane$: Calcd. (%): C,55.22; H,5.90; N,8.78; S,6.70 Found (%): C,55.24; H,6.05; N,8.57; S,6.84

EXAMPLE 93

Preparation of solid solution of 3-[(2-mercaptomethyl-3-phenylpropionyl)amino]benzoic acid with L-aspartic acid In the same manner as described in Example 87 except that L-aspartic acid is used instead of glycine, there is prepared the title compound.
m.p.: 173°-179° C. (amorphous)

IR (KBr; cm$^{-1}$): 1680, 1650
Elementary analysis for $C_{17}H_{17}NO_3S.C_4H_7NO_4.0.5-H_2O$: Calcd. (%): C,55.13; H,5.51; N,6.12: S,7.01 Found (%): C,55.14; H,5.58; N,5.97; S,6.73

EXAMPLE 94

Preparation of solid solution of 3-[(2-acetylthiomethyl-3-phenylpropionyl)amino]benzoic acid with glycine In the same manner as described in Example 87, there is prepared the title compound.
m.p.: 165°-168° C. (amorphous)
IR (KBr; cm$^{-1}$): 1680, 1650, 1605
Elementary analysis for $C_{19}H_{19}NO_4S.C_2H_5NO_2.dioxane$: Calcd. (%): C,57.68; H,6.20; N,5.38; S,6.16 Found (%): C,57.66; H,6.15; N,5.54; S,6.32

EXAMPLE 95

Preparation of solid solution of 3-[(2-acetylthiomethyl-3-phenylpropionyl)amino]-4-methylbenzoic acid with glycine In the same manner as described in Example 87, there is prepared the title compound.
m.p.: 196°-198° C. (amorphous)
IR (KBr; cm$^{-1}$): 1685, 1650, 1610
Elementary analysis for $C_{20}H_{21}NO_4S.C_2H_5NO_2.0.1-H_2O$: Calcd. (%): C,58.94; H,5.89; N,6.25; S,7.15 Found (%): C,58.69; H,5.82; N,6.44; S,6.98

EXAMPLE 96

Preparation of solid solution of 3-[[2-acetylthio methyl-3-(4-methoxyphenyl)propionyl]amino]benzoic acid with glycine In the same manner as described in Example 87, there is prepared the title compound.
m.p.:126°-128° C. (amorphous)
IR (KBr; cm$^{-1}$): 1680, 1650
Elementary analysis for $C_{20}H_{21}NO_5S.C_2H_5NO_2.0.25H_2O$: Calcd. (%): C,56.58; H,5.72; N,6.00; S,6.87 Found (%): C,56.63; H,5.76; N,6.30; S,6.86

EXAMPLE 97

Preparation of solid solution of 3-[(2-acetylthiomethyl-5-phenylpentanoyl)amino]benzoic acid with glycine In the same manner as described in Example 87, there is prepared the title compound.
m.p.: 141°-143° C. (amorphous)
IR (KBr; cm$^{-1}$): 1680, 1650
Elementary analysis for $C_{21}H_{24}NO_4S.C_2H_5NO_2$: Calcd. (%): C,59.85; H,6.33; N,6.07; S,6.95 Found (%): C,59.58; H,5.99; N,6.12; S,6.96

EXAMPLE 98

Preparation of solid solution of 3-[[2-acetylthiomethyl-3-(4-dimethylaminophenyl)propionyl]amino]benzoic acid with glycine In the same manner as described in Example 87, there is prepared the title compound.
m.p.: 74°-76° C. (amorphous)
IR (KBr; cm$^{-1}$): 1680, 1660
Elementary analysis for $C_{21}H_{24}N_2O_4S.C_2H_5NO_2.0.75H_2O$: Calcd. (%): C,56.48; H,6.29; N,8.59; S,6.56 Found (%): C,56.51; H,6.45; N,8.58; S,6.27

EXAMPLE 99

Preparation of solid solution of 3-[[2-mercaptomethyl-3-(4-dimethylaminophenyl)propionyl]amino]benzoic acid with glycine In the same manner as described in Example 87, there is prepared the title compound.
m.p.: 93°–96° C. (amorphous)
IR (KBr; cm$^{-1}$): 1680, 1660
Elementary analysis for $C_{19}H_{22}N_2O_3S \cdot C_2H_5NO_2 \cdot 0.5H_2O$: Calcd. (%): C,57.00; H,6.38; N,9.50; S,7.25 Found (%): C,56.74; H,6.44; N,9.56; S,7.24

EXAMPLE 100

Preparation of solid solution of 3-[[2-acetylthiomethyl-3-(3-pyridyl)propionyl]amino]benzoic acid with glycine In the same manner as described in Example 87, there is prepared the title compound.
m.p.: 193°–195° C. (amorphous)
IR (KBr; cm$^{-1}$): 1680, 1660
Elementary analysis for $C_{18}H_{18}N_2O_4S \cdot C_2H_5NO_2 \cdot 0.25H_2O$: Calcd. (%): C,54.85; H,5.41; N,9.59; S,7.32 Found (%): C,54.63; H,5.53; N,9.77; S,7.13

EXAMPLE 101

Preparation of solid solution of 3-[[2-mercaptomethyl-3-(3-pyridyl)propionyl]amino]benzoic acid with glycine In the same manner as described in Example 87, there is prepared the title compound.
m.p.: 113°–116° C. (amorphous)
IR (KBr; cm$^{-1}$): 1680, 1650
Elementary analysis for $C_{16}H_{16}N_2O_3S \cdot C_2H_5NO_2 \cdot 0.75H_2O$: Calcd. (%): C,53.39; H,5.60; N,10.38; S,7.92 Found (%): C,53.41; H,5.61; N,10.20; S,7.53

EXAMPLE 102

Preparation of solid solution of 3-[(2-mercaptomethyl-3-phenylpropionyl)amino]-4-methylbenzoic acid with glycine In the same manner as described in Example 87, there is prepared the title compound.
m.p.: 166°–173° C. (amorphous)
IR (KBr; cm$^{-1}$): 1680, 1650, 1640, 1605
Elementary analysis for $C_{18}H_{19}NO_3S \cdot C_2H_5NO_2 \cdot 0.5H_2O$: Calcd. (%): C,58.10; H,6.09; N,6.77; S,7.75 Found (%): C,57.84; H,5.90; N,7.14; S,7.63

EXAMPLE 103

Preparation of solid solution of 3-[(2-acetylthiomethyl-3-phenylpropionyl)amino]-5-ethylbenzoic acid with glycine In the same manner as described in Example 87, there is prepared the title compound.
m.p.: 166°–169° C. (amorphous)
IR (KBr; cm$^{-1}$): 1690, 1660, 1600
Elementary analysis for $C_{21}H_{23}NO_4S \cdot C_2H_5NO_2 \cdot 0.5H_2O$: Calcd. (%): C,58.83; H,6.23; N,5.97; S,6.83 Found (%): C,58.67; H,6.10; N,6.07; S,6.58

EXAMPLE 104

Preparation of solid solution of 3-[(2-mercaptomethyl-3-phenylpropionyl)amino]-2-methylbenzoic acid with glycine In the same manner as described in Example 87, there is prepared the title compound.
m.p.: 86°–98° C. (amorphous)
IR (KBr; cm$^{-1}$): 1690, 1650, 1600
Elementary analysis for $C_{18}H_{19}NO_3S \cdot C_2H_5NO_2 \cdot H_2O \cdot 0.2\text{dioxane}$: Calcd. (%): C,56.76; H,6.32; N,6.37; S,7.29 Found (%): C,56.48; H,5.93; N,6.55; S,7.07

EXAMPLE 105

Preparation of solid solution of 3-[(2-mercaptomethyl-3-phenylpropionyl)amino]-5-methylbenzoic acid with glycine In the same manner as described in Example 87, there is prepared the title compound.
m.p.: 105°–112° C. (amorphous)
IR (KBr; cm$^{-1}$): 1690, 1660, 1600
Elementary analysis for $C_{18}H_{19}NO_3S \cdot C_2H_5NO_2 \cdot 0.75H_2O \cdot 0.25\text{dioxane}$: Calcd. (%): C,57.32; H,6.30; N,6.37; S,7.29 Found (%): C,57.54; H,5.90; N,6.48; S,6.95

EXAMPLE 106

Preparation of solid solution of 3-[(2-mercaptomethyl-3-phenylpropionyl)amino]benzoic acid with 3-aminobenzoic acid 3-[(2-Mercaptomethyl-3-phenylpropionyl)amino]benzoic acid (compound of Example 68) (0.16 g) and 3-aminobenzoic acid (0.07 g) are dissolved in dioxane (removing peroxide by passing through a neutral alumina column) (30 ml), and thereto is added water (10 ml), and the mixture is lyophilized. The resulting oily substance is dried over phosphorus pentoxide under reduced pressure to give the title compound (0.23 g).
IR (KBr; cm$^{-1}$): 1675, 1650
Elementary analysis for $C_{17}H_{17}NO_3S \cdot C_7H_7NO_2 \cdot 0.3\text{dioxane}$: Calcd. (%): C,63.19; H,5.56; N,5.85; S,6.69 Found (%): C,63.10; H,5.60; N,5.87; S,6.41

EXAMPLE 107

Preparation of 3-[(2-mercaptomethyl-3-phenylpropionyl)amino]benzoic acid·2,6-di-O-methyl-β-cyclodextrin inclusion compound In the same manner as described in Example 87 except that 2,6-di-O-methyl-β-cyclodextrin is used instead of the amino acid, there is prepared the title compound.
m.p.: 136°–142° C. (amorphous)
IR (KBr; cm$^{-1}$): 1715, 1685, 1610
Elementary analysis for $C_{17}H_{17}NO_3S \cdot C_{56}H_{98}O_{35} \cdot H_2O$: Calcd. (%): C,52.67; H,7.08; N,0.84; S,1.93 Found (%): C,52.41; H,7.19; N,0.76; S,2.00

EXAMPLE 108

Preparation of 3-[(2-mercaptomethyl-3-phenylpropionyl)amino]benzoic acid sodium salt In the same manner as described in Example 42, there is prepared the title compound.
m.p.: 160°–165° C. (amorphous)
IR (KBr; cm$^{-1}$): 1650, 1605

Elementary analysis for $C_{17}H_{16}NO_3SNa.0.25H_2O$:
Calcd. (%): C,59.73; H,4.86; N,4.10; S,9.38; Na,6.72
Found (%): C,59.49; H,4.79; N,4.26; S,9.29; Na,6.76

EXAMPLE 109

Preparation of N,N'-[3,3'-dithiobis(2-benzylpropionyl)]bis(3-aminobenzoic acid) (a mixture of diastereomers)

3-[(2 Mercaptomethyl-3-phenylpropionyl)amino]benzoic acid (compound of Example 68) (3 g) is dissolved in aqueous ethanol (100 ml), and thereto is added 0.1 N aqueous iodine solution (30 ml) with stirring at room temperature. After reacting for 2 hours, an aqueous sodium thiosulfate solution is added to the mixture. Ethanol is distilled off under reduced pressure, and the mixture is acidified with 10% hydrochloric acid and extracted with ethyl acetate. The extract is washed with saturated aqueous sodium chloride solution, dried over anhydrous sodium sulfate, and ethyl acetate is distilled off under reduced pressure. The residue is purified by a medium pressure column chromatography with CHP-20P (eluant, water-acetonitrile). The fractions containing the desired compound are collected and concentrated under reduced pressure. The precipitates are separated by filtration to give the title compound (2.28 g).
m.p.: 220°-230° C. (amorphous)
IR (KBr; cm$^{-1}$): 1685, 1650
Elementary analysis for $C_{34}H_{32}N_2O_6S_2$: Calcd. (%): C,64.95; H,5.13; N,4.46; S,10.20 Found (%): C,65.02; H,5.28; N,4.28; S,9.82

EXAMPLE 110

Preparation of isopentyl 3-[(2-acetylthiomethyl-3-phenylpropionyl)amino]benzoate In the same manner as described in Example 61, the reaction is carried out, and at the final step the product is purified by a column chromatography using Diaion HP 20 to give the title compound.
m.p.: 96°-98° C. (colorless needles) (recrystallized from 80% aqueous acetonitrile solution)
IR (KBr; cm$^{-1}$): 1705, 1695, 1660
Elementary analysis for $C_{24}H_{29}NO_4S$: Calcd. (%) C,67.42; H,6.84; N,3.28; S,7.50 Found (%): C,67.43; H,6.78; N,3.29; S,7.25

EXAMPLE 111

Preparation of cyclohexylmethyl 3-[(2-acetylthiomethyl-3-phenylpropionyl)amino]benzoate In the same manner as described in Example 110, there is prepared the title compound as an oily substance.
IR (film; cm$^{-1}$): 1720, 1690, 1660
Elementary analysis for $C_{26}H_{30}NO_4S$: Calcd. (%): C,69.00; H,6.68; N,3.09; S,7.08 Found (%): C,68.82; H,6.92; N,3.20; S,6.95

EXAMPLE 112

Preparation of 2-piperidinoethyl 3-[(2-acetylthiomethyl-3-phenylpropionyl)amino]benzoate In the same manner as described in Example 110, there is prepared the title compound as an oily substance.

IR (film; cm$^{-1}$): 1720, 1710, 1680
Elementary analysis for $C_{26}H_{32}N_2O_4S.0.7CF_3COOH.0.7H_2O$: Calcd. (%): C,58.66; H,6.13; F,7.11; N,4.99; S,5.72 Found (%): C,58.36; H,5.91; F,7.40; N,4.99; S,5.89

EXAMPLE 113

Preparation of 1-methyl-2-piperidinylmethyl 3-[(2-acetylthiomethyl-3-phenylpropionyl)amino]benzoate (a mixture of diastereomers)

In the same manner as described in Example 110, there is prepared the title compound.
IR (KBr; cm$^{-1}$): 1720, 1690, 1670
Elementary analysis for $C_{26}H_{32}N_2O_4S.0.75CF_3COOH.H_2O$: Calcd (%): C,57.73; H,6.12; F,7.47; N,4.90; S,5.60 Found (%): C,58.15; H,6.20; F,7.11; N,4.94; S,5.66

EXAMPLE 114

Preparation of 2-dimethylaminoethyl 3-[(2-acetylthiomethyl-3-phenylpropionyl)amino]benzoate hydrochloride In the same manner as described in Example 61, there is prepared the title compound.
m.p.: 31°-32° C. (amorphous)
IR (KBr; cm$^{-1}$): 1710, 1680
Elementary analysis for $C_{23}H_{28}N_2O_4S.HCl.0.25H_2O$: Calcd. (%) C,58.84; H,6.33; Cl,7.55; N,5.97; S,6.83 Found (%): C,58.85; H,6.42; Cl,7.69; N,5.99; S, 6.78

EXAMPLE 115

Preparation of 3-pyridylmethyl 3-[(2-acetylthiomethyl-3-phenylpropionyl)amino]benzoate hydrochloride In the same manner as described in Example 61, there is prepared the title compound.
m.p.: 69°-72° C. (amorphous)
IR (KBr; cm$^{-1}$): 1710, 1680
Elementary analysis for $C_{25}H_{24}N_2O_4S.HCl$: Calcd. (%): C,61.91; H,5.20; Cl,7.31; N,5.78; S,6.61 Found (%) C,61.83; H,5.47; Cl,6.83; N,5.67; S,6.74

EXAMPLE 116

Preparation of cyanomethyl 3-[(2-acethylthiomethyl-3-phenylpropionyl)amino]benzoate Cyanomethyl 3-(t-butyloxycarbonylamino)benzoate [compound of Example 61-(2)] (6.9 g), anisole (one drop) and trifluoroacetic acid (10 ml) are mixed. The mixture is stirred under ice cooling for 10 minutes and further at room temperature for 30 minutes. Excess trifluoroacetic acid is distilled off under reduced pressure. To the residue is added 60% aqueuous tetrahydrofuan (30 ml), and thereto is added dropwise a solution of 2-acetylthiomethyl-3-phenylpropionyl chloride (5 g) in tetrahydrofuran (20 ml) with stirring under ice cooling while maintaining at pH 7.0-7.5 with triethylamine, and the mixture is stirred at room temperature for 2 hours. Tetrahydrofuran is distilled off under reduced pressure, and the residue is extracted with ethyl acetate (100 ml). The extract is washed with water, dried over anhydrous sodium sulfate, and ethyl acetate is distilled off under reduced pressure. The residue is purified by a silica gel column chromatography (eluant, chloroform-ethyl acetate). The fractions containing the desired compound are collected and concentrated under reduced pressure to give the title compound (3.5 g) as an oily substance.

IR (film; cm$^{-1}$): 1730, 1680, 1660

Elementary analysis for $C_{21}H_{20}N_2O_4S$: Calcd. (%) C,63.62; H,5.08; N,7.07; S,8.09 Found (%): C,63.27; H,5.28; N,7.41; S,8.08

EXAMPLE 117

Preparation of 2-phenoxyethyl 3-[(2-acetylthiomethyl-3-phenylpropionyl)amino]benzoate Cyanomethyl 3-[(2 acetylthiomethyl-3-phenylpropionyl)amino]benzoate (compound of Example 116) (4 g), 2-phenoxyethanol (3 g), 4-dimethylaminopyridine (0.1 g) and triethylamine (2 g) are mixed, and the mixture is stirred at 60° C. for 15 hours and extracted with ethyl acetate (50 ml). The extract is washed with 10% hydrochloric acid and water, and ethyl acetate is distilled off under reduced pressure. The residue is dissolved in 50% aqueous acetonitrile and purified by a column chromatography using Diaion HP-20 (eluant, water-acetonitrile). The fractions containing the desired compound are collected, and acetonitrile is distilled off under reduced pressure. The aqueous solution is extracted with ethyl acetate (100 ml). The extract is dried over anhydrous magnesium sulfate, and ethyl acetate is distilled off under reduced pressure to give the title compound (2.5 g).

m.p.: 90°-92° C. (amorphous)

IR (KBr; cm$^{31\ 1}$): 1720, 1690, 1660

Elementary analysis for $C_{27}H_{27}NO_5S$: Calcd. (%): C,67.90; H,5.70; N,2.93; S,6.71 Found (%): C,67.51; H,5.61; N,2.88; S,6.59

EXAMPLE 118

Preparation of pivaloyloxymethyl 3-[(2-acetylthiomethyl-3-phenylpropionyl)amino]benzoate (1) 3-(t-Butyloxycarbonylamino)benzoic acid sodium salt (10 g), DMF (60 ml) and potassium iodide (6.3 g) are mixed, and thereto is added dropwise pivaloyloxymethyl chloride (6 g) under ice cooling. The mixture is stirred at room temperature for 15 hours, and thereto is added ethyl acetate (200 ml). The mixture is washed with water, and ethyl acetate is distilled off under reduced pressure. The residue is recrystallized from 70% aqueous acetonitrile to give pivaloyloxymethyl 3-(t-butyloxycarbonylamino)benzoate (11.9 g).

m.p.: 88°-89° C. (colorless needles)

IR (KBr; cm$^{-1}$): 1740, 1725, 1695

Elementary analysis for $C_{18}H_{25}NO_6$: Calcd. (%): C,61.52; H,7.17; N,3.99 Found (%): C,61.78; H,7.43; N,4.08

(2) The compound prepared in the above (1) (3.5 g) is mixed with trifluoroacetic acid (3 ml), and the mixture is stirred at room temperature for 30 minutes. The reaction mixture is concentrated under reduced pressure and dissolved in water (20 ml). The solution is added dropwise to a solution of 2-acetylthiomethyl-3-phenylpropionyl chloride (2.5 g) in tetrahydrofuran (30 ml) with stirring under ice cooling. While maintaining at pH 7.0-7.5 with 10% aqueous sodium hydroxide solution, the mixture is stirred under ice cooling for 30 minutes and further at room temperature for one hour, and then adjusted to pH 3.0 with 20% hydrochloric acid. Tetrahydrofuran is distilled off under reduced pressure, and the residue is extracted with ethyl acetate (50 ml). The extract is washed with water, and ethyl acetate is distilled off under reduced pressure. The residue is dissolved in 50% aqueous acetonitrile and purified by a medium pressure column chromatography with CHP-20P (eluant, water-acetonitrile). The fractions containing the desired compound are collected, and acetonitrile is distilled off under reduced pressure. The residue is extracted with ethyl acetate (100 ml), and the extract is dried over anhydrous magnesium sulfate, and ethyl acetate is distilled off under reduced pressure to give the title compound (3 g) as a yellow oily substance.

IR (film; cm$^{-1}$): 1735, 1680, 1660

Elementary analysis for $C_{25}H_{29}NO_6S$: Calcd. (%): C,63.68; H,6.20; N,2.97; S,6.80 Found (%): C,63.39; H,6.48; N,3.09; S,6.52

EXAMPLE 119

Preparation of pivaloyloxymethyl 3-[[2-acetylthiomethyl-3-(3-pyridyl)propionyl]amino]benzoate hydrochloride In the same manner as described in Example 118, there is prepared the title compound.

m.p.: 68°-70° C. (amorphous)

IR (KBr; cm$^{-1}$): 1730, 1680

Elementary analysis for $C_{24}H_{28}N_2O_6S \cdot HCl$: Calcd. (%): C,56.63; H,5.74; Cl,6.96; N,5.50; S,6.30 Found (%): C,56.29; H,5.94; Cl,6.62; N,5.40; S,6.11

EXAMPLE 120

Preparation of pivaloyloxymethyl 3-[[2-acetylthiomethyl-3-(4-dimethylaminophenyl)propionyl]amino]benzoate hydrochloride In the same manner as described in Example 118, there is prepared the title compound. IR (KBr; cm$^{-1}$): 1730, 1680

Elementary analysis for $C_{27}H_{34}N_2O_6S \cdot HCl \cdot 0.75H_2O$: Calcd. (%): C,57.44; H,6.52; Cl,6.28; N,4.96; S,5.68 Found (%): C,57.21; H,6.72; Cl,6.54; N,5.13; S,5.86

EXAMPLE 121

Preparation of 4-(t-butyloxycarbonylaminomethyl)-benzyl 3-[(2-acetylthiomethyl-3-phenylpropionyl)amino]-benzoate In the same manner as described in Example 72, there is prepared the title compound as a caramel-like substance. IR: (KBr; cm$^{-1}$): 1710 (shoulder), 1690, 1650 (shoulder)

Elementary analysis for $C_{32}H_{36}N_2O_6S \cdot 0.5H_2O$: Calcd. (%): C,65.62; H,6.37; N,4.78; S,5.47 Found (%): C,65.44; H,6.29; N,4.67; S,5.28

EXAMPLE 122

Preparation of 4-aminomethylbenzyl 3-[(2-acetylthiomethyl-3-phenylpropionyl)amino]benzoate hydrochloride 4-(t-Butyloxycarbonylaminomethyl)benzyl 3-[(2-acetylthiomethyl 3-phenylpropionyl)amino]benzoate (compound of Example 121) (0.73 g) is dissolved in 1M hydrochloric acid-acetic acid solution (20 ml), and the mixture is reacted at room temperature for 45 minutes. The reaction mixture is added slowly to diethyl ether (100 ml) with stirring under ice cooling. The precipitates are separated by filtration and washed with diethyl ether to give the title compound (0.61 g). m.p.: 111°-113° C. (amorphous) IR (KBr; cm$^{-1}$): 1710, 1685, 1650

Elementary analysis for $C_{27}H_{28}N_2O_4S \cdot HCl \cdot 0.25H_2O$:
Calcd. (%): C,62.66; H,5.75; Cl,6.85; N,5.41; S,6.20
Found (%): C,62.77; H,5.92; Cl,7.06; N,5.30; S,5.94

EXAMPLE 123

Preparation of 2-bromoethyl 3-[(2-acetylthiomethyl-3-phenylpropionyl)amino]benzoate In the same manner as described in Example 72, there is prepared the title compound. m.p.: 85°–88° C. (amorphous) IR (KBr; cm$^{-1}$): 1720, 1690, 1660

Elementary analysis for $C_{21}H_{22}BrNO_4S$: Calcd. (%): C,54.32; H,4.78; Br,17.21; N,3.02; S,6.90 Found (%): C,54.61; H,4.80; Br,17.37; N,2.95; S,6.80

EXAMPLE 124

Preparation of 2-hydroxyethyl 3-[(2-acetylthiomethyl-3-phenylpropionyl)amino]benzoate 2-Bromoethyl 3-[(2-acetylthiomethyl-3-phenylpropionyl)amino]benzoate (compound of Example 123) (0.63 g) and 3-pyridinecarboxamide (0.17 g) are dissolved in methanol (10 ml), and the mixture is refluxed overnight. Methanol is distilled off under reduced pressure, and the residue is dissolved in ethyl acetate, washed with water and dried over anhydrous magnesium sulfate. Ethyl acetate is distilled off under reduced pressure. The residue is purified by a medium pressure column chromatography with silica gel (eluant, chloroform). The fractions containing the desired compound are collected, and chloroform is distilled off under reduced pressure to give the title compound (0.3 g) as an oily substance. IR (film; cm$^{-1}$): 1715, 1685, 1660 Mass spectrum (SIMS) [M+H]$^+$: m/z 402

EXAMPLE 125

Preparation of 2-[3-[(2-acetylthiomethyl-3-phenylpropionyl)amino]benzoyl]-1, 3-dihexadecanoylpropane-1,2,3-triol In the same manner as described in Example 72, there is prepared the title compound. m.p.: 65°–67° C. (amorphous) IR (KBr; cm$^{-1}$): 1740, 1725, 1690, 1660

Elementary analysis for $C_{54}H_{85}NO_8S \cdot 0.5$n-hexane Calcd. (%): C,71.96; H,9.75; N,1.47; S,3.37 Found (%): C,71.73; H,9.84; N,1.46; S,3.03

EXAMPLE 126

Preparation of diethylaminocarbonylmethyl 3-[(2-acetylthiomethyl-3-phenylpropionyl)amino]benzoate 3-[(2-Acetylthiomethyl-3-phenylpropionyl)amino]benzoic acid (compound of Example 68-(b)-[1]) (0.72 g) and potassium iodide (0.37 g) are dissolved in DMF, and thereto are added triethylamine (0.2 g) and 2-chloro-N,N-diethylacetamide (0.33 g) with stirring at room temperature, and the mixture is reacted three nights. The reaction mixture is mixed with water and extracted with ethyl acetate. The extract is washed with water, dried over anhydrous magnesium sulfate, and ethyl acetate is distilled off under reduced pressure. The residue is purified by a medium pressure column chromatography using silica gel (eluant, chloroform). The fractions containing the desired compound are collected, and chloroform is distilled off under reduced pressure to give the title compound (0.71 g). m.p.: 143°–144° C. (amorphous) IR (KBr; cm$^{-1}$): 1725, 1690, 1635

Elementary analysis for $C_{25}H_{30}N_2O_5S$: Calcd. (%): C,63.81; H,6.43; N,5.95; S,6.81 Found (%): C,63.85; H,6.37; N,6.00; S,6.99

EXAMPLE 127

Preparation of N-[3-[(2-acetylthiomethyl-3-phenylpropionyl)amino]benzoyl]glycine benzyl ester (1) Cyanomethyl 3-(t-butyloxycarbonylamino)-benzoate [compound of Example 61-(2)] (27.6 g), glycine benzyl ester·p-toluenesulfonate (33.7 g), triethylamine (20.2 g) and 4-dimethylaminopyridine (0.2 g) are mixed. The mixture is stirred at 80° C. two nights. The reaction mixture is extracted with ethyl acetate (200 ml). The extract is washed with water, and ethyl acetate is distilled off under reduced pressure. The residue is purified by a silica gel column chromatography (eluant, chloroform-ethyl acetate). The fractions containing the desired compound are collected, and the solvent is distilled off under reduced pressure. The residue is recrystallized from 70% aqueous acetonitrile to give N-[3-(t butyloxycarbonylamino)benzoyl]glycine benzyl ester (7.2 g). m.p.: 171°–173° C. (colorless needles) IR (KBr; cm$^{-1}$): 1725, 1695, 1640

Elementary analysis for $C_{21}H_{24}N_2O_5$: Calcd. (%): C,65.61; H,6.29; N,7.29 Found (%): C,65.56; H,6.38; N,7.36

(2) The compound prepared in the above (1) (3.8 g) is mixed with trifluoroacetic acid (2.5 ml), and the mixture is stirred at room temperature for 30 minutes, and trifluoroacetic acid is distilled off under reduced pressure. The residue is dissolved in 80% aqueous tetrahydrofuran (20 ml). The solution is added dropwise to a solution of 2-acetylthiomethyl-3-phenylpropionyl chloride (2.6 g) in chloroform. While maintaining at pH 7.0–7.5 with triethylamine, the mixture is stirred under ice cooling for 30 minutes and further at room temperature for one hour, and then chloroform and tetrahydrofuran are distilled off under reduced pressure. The residue is extracted with ethyl acetate (100 ml). The extract is washed with water, and ethyl acetate is distilled off under reduced pressure. The residue is purified by a column chromatography using Diaion HP-20 (eluant, water-acetonitrile). The fractions containing the desired compound are collected, and acetonitrile is distilled off under reduced pressure. The aqueous solution is extracted with ethyl acetate, and the extract is dried over anhydrous magnesium sulfate, and ethyl acetate is distilled off under reduced pressure to give the title compound (2.5 g). m.p.: 122°–123° C. (amorphous) IR (KBr; cm$^{-1}$): 1730, 1680, 1650, 1640

Elementary analysis for $C_{28}H_{28}N_2O_5S$: Calcd. (%): C,66.65; H,5.59; N,5.55; S,6.35 Found (%): C,66.53; H,5.77; N,5.40; S,6.60

EXAMPLE 128

Preparation of N-[3-[(2-acetylthiomethyl-3-phenylpropionyl)amino]benzoyl]-L-phenylalanine benzyl ester (a mixture of diastereomers):

In the same manner as described in Example 127, there is prepared the title compound. m.p.: 89°–91° C. (amorphous) IR (KBr; cm$^{-1}$): 1730, 1680, 1640

Elementary analysis for $C_{35}H_{24}N_3O_5S$: Calcd. (%): C,70.69; H,5.76; N,4.71; S,5.39 Found (%): C,71.13; H,6.01; N,4.38; S,5.40

EXAMPLE 129

Preparation of ethyl 3-[(2-mercaptomethyl-3-phenylpropionyl)amino]benzoate

Ethyl 3-[(2-acetylthiomethyl-3-phenylpropionyl)-amino]benzoate (compound of Example 68-(a)-[1]) (2.0 g) is dissolved in a 80% aqueous acetonitrile, and thereto is added pyrrolidine (0.5 g), and the mixture is stirred at room temperature for 30 minutes. The mixture is adjusted to pH 5.0 with 10% hydrochloric acid, and acetonitrile is distilled off under reduced pressure, and the residue is extracted with ethyl acetate (50 ml). The extract is washed with water, and ethyl acetate is distilled off under reduced pressure. The residue is purified by a medium pressure column chromatography with CHP-20P (eluant, water-acetonitrile). The fractions containing the desired compound are collected, and acetonitrile is distilled off under reduced pressure. The aqueous solution is extracted with ethyl acetate (50 ml), and the extract is dried over anhydrous magnesium sulfate, and ethyl acetate is distilled off under reduced pressure to give the title compound (0.5 g) as an oily substance. IR (film; cm$^{-1}$): 1710, 1660 Elementary analysis for $C_{19}H_{21}NO_3S$: Calcd. (%): C,66.45; H,6.16; N,4.08; S,9.34 Found (%): C,66.37; H,6.25; N,4.04; S,9.05

EXAMPLE 130

Preparation of methyl 3-[(2-mercaptomethyl-3-phenylpropionyl)amino]benzoate

In the same manner as described in Example 129, there is prepared the title compound as an oily substance. IR (film; cm$^{-1}$): 1720, 1660

Elementary analysis for $C_{18}H_{19}NO_3S$: Calcd. (%): C,65.63; H,5.81; N,4.25; S,9.73 Found (%): C,65.27; H,5.87; N,4.48; S,9.57

EXAMPLE 131

Preparation of isopentyl 3-[(2-mercaptomethyl-3-phenylpropionyl)amino]benzoate

In the same manner as described in Example 129, there is prepared the title compound as an oily substance. IR (film; cm$^{-1}$): 1710, 1660

Elementary analysis for $C_{22}H_{27}NO_3S$: Calcd. (%): C,68.54; H,7.06; N,3.63; S,8.32 Found (%): C,68.32; H,6.99; N,3.78; S,8.53

EXAMPLE 132

Preparation of cyclohexylmethyl 3-[(2-mercaptomethyl-3-phenylpropionyl)amino]benzoate In the same manner as described in Example 129, there is prepared the title compound as an oily substance. IR (film; cm$^{-1}$): 1720, 1660

Elementary analysis for $C_{24}H_{28}NO_3S.0.25H_2O$: Calcd. (%): C,69.45; H,6.92; N,3.37; S,7.82 Found (%): C,69.68; H,7.13; N,3.33; S,7.73

EXAMPLE 133

Preparation of 2-piperidinoethyl 3-[(2-mercaptomethyl-3-phenylpropionyl)amino]benzoate In the same manner as described in Example 129 except the crude product obtained in Example 112 is used, there is prepared the title compound. IR (film; cm$^{-1}$): 1720, 1670 Elementary analysis for $C_{24}H_{30}N_2O_3S.CF_3COOH$: Calcd. (%): C,57.77; H,5.78; F,10.54; N,5.18; S,5.93 Found (%): C,57.36; H,5.80; F,10.25; N,5.16; S,6.33

EXAMPLE 134

Preparation of 1-methyl-2-piperidinylmethyl 3-[(2-mercaptomethyl 3 phenylpropionyl)amino]benzoate (a mixture of diastereomers)

In the same manner as described in Example 129 except that the crude product obtained in Example 113 is used, there is prepared the title compound. m.p.: 68°-69° C. (amorphous) IR (KBr; cm$^{-1}$): 1715, 1660

Elementary analysis for $C_{24}H_{30}N_2O_3S.0.9CF_3COOH.0.5H_2O$: Calcd. (%): C,57.58; H,5.97; F,9.53; N,5.21; S,5.96 Found (%): C,57.77; H,5.91; F,9.50; N,5.15; S,6.10

EXAMPLE 135

Preparation of 2-dimethylaminoethyl 3-[(2-mercaptomethyl-3-phenylpropionyl)amino]benzoate In the same manner as described in Example 129 except that the crude product obtained in Example 114 is used, there is prepared the title compound as an oily substance. IR (film; cm$^{-1}$): 1720, 1670

Elementary analysis for $C_{21}H_{26}N_2O_3S.0.5CF_3COOH.H_2O$: Calcd. (%): C,57.25; H,6.22; F,6.17; N,6.07; S,6.95 Found (%): C,56.82; H,5.97; F,6.10; N,6.08; S,7.19

EXAMPLE 136

Preparation of 3-pyridylmethyl 3-[(2-mercaptomethyl-3-phenylpropionyl)amino]benzoate:

In the same manner as described in Example 129 except that the crude product obtained in Example 115 is used, there is prepared the title compound as an oily substance. IR (film; cm$^{-1}$): 1700, 1680

Elementary analysis for $C_{23}H_{22}N_2O_3S.0.25H_2O$: Calcd. (%): C,67.21; H,5.52; N,6.82; S,7.80 Found (%): C,67.34; H,5.44; N,6.62; S,7.84

EXAMPLE 137

Preparation of 2 phenoxyethyl 3-[(2-mercaptomethyl-3-phenylpropionyl)amino]benzoate In the same manner as described in Example 129, there is prepared the title compound as an oily substance. m.p.: 98°-100° C. (amorphous) IR (KBr; cm$^{-1}$): 1720, 1660

Elementary analysis for $C_{25}H_{25}NO_4S.0.25H_2O$: Calcd. (%): C,68.24; H,5.84; N,3.18; S,7.29 Found (%): C,68.34; H,5.65; N,3.10; S,7.05

EXAMPLE 138

Preparation of pivaloyloxymethyl 3-[(2-mercaptomethyl-3-phenylpropionyl)amino]benzoate (1) 2-Acetylthiomethyl-3-phenylpropionic acid (18.5 g) is mixed with 70% aqueous methanol (100 ml), and the mixture is stirred at room temperature for one hour under nitrogen while maintaining at pH 13.0 with 20% aqueous sodium hydroxide solution, and thereafter the mixture is adjusted to pH 2.0 with 20% hydrochloric acid, and methanol is distilled off under reduced pressure. The residue is purified by a column chromatography using Diaion HP-20 (eluant, water-acetonitrile). The fractions containing the desired compound are collected and acetonitrile is distilled off under reduced pressure. The aqueous solution is extracted with ethyl acetate. The extract is dried over anhydrous magnesium sulfate, and ethyl acetate is distilled off under reduced pressure to give 2-mercaptomethyl-3-phenylpropionic acid (8 g) as a colorless oily substance. IR (film; cm$^{-1}$): 1700

Elementary analysis for $C_{10}H_{12}O_2S$: Calcd. (%): C,61.20; H,6.16; S,16.34 Found (%): C,61.30; H,6.07; S,16.56

(2) A mixture of the compound prepared in the above (1) (3.9 g), thionyl chloride (3 ml) and chloroform (30 ml) is refluxed for 30 minutes. The reaction mixture is concentrated under reduced pressure, and the residue is dissolved in chloroform (30 ml).

Separately, pivaloyloxymethyl 3-(t-butyloxycarbonylamino)benzoate [compound of Example 118-(1)] (7 g) is mixed with trifluoroacetic acid (7 ml), and the mixture is stirred at room temperature for 30 minutes. The reaction mixture (containing pivaloyloxymethyl 3-aminobenzoate) is concentrated under reduced pressure and dissolved in tetrahyrofuran (30 ml). To the solution is added dropwise the solution of the acid chloride prepared above in chloroform with stirring under ice cooling. After neutralizing with triethylamine, the mixture is stirred under ice cooling for 30 minutes and further at room temperature for one hour, and concentrated under reduced pressure, and the residue is extracted with ethyl acetate (100 ml). The extract is washed with water, and ethyl acetate is distilled off under reduced pressure. To the residue are added acetonitrile (50 ml), acetic acid (10 ml) and zinc dust (5 g), and the mixture is stirred at room temperature for one hour. After filtering off zinc dust, the filtrate is concentrated and extracted with ethyl acetate (100 ml). The extract is washed with water, dried over anhydrous magnesium sulfate, and ethyl acetate is distilled off under reduced pressure. The residue is purified by a medium pressure column chromatography using silica gel (eluant, chloroform-methanol). The fractions containing the desired compound are collected, and the solvent is distilled off under reduced pressure to give the title compound (2.5 g) as an oily substance. IR (film; cm$^{-1}$): 1740, 1690, 1660

Elementary analysis for $C_{23}H_{27}NO_5S$: Calcd. (%): C,64.31; H,6.34; N,3.26; S,7.46 Found (%): C,64.10; H,6.61; N,3.38; S,7.58

EXAMPLE 139

Preparation of 4-(t butyloxycarbonylaminomethyl)-benzyl 3-[(2-mercaptomethyl-3-phenylpropionyl)amino]-benzoate:

N,N'-[3,3'-dithiobis(2-benzylpropionyl)]bis(3-aminobenzoic acid) (compound of Example 109) (0.61 g), 4-dimethylaminopyridine (0.02 g) and 4-(t-butyloxycarbonylaminomethyl)benzyl alcohol (0.46 g) are suspended in dichloromethane (50 ml), and thereto is added EDC.HCl (0.41 g), and the mixture is stirred at room temperature three nights. The reaction mixture is washed with saturated aqueous sodium chloride solution, dried over anhydrous magnesium sulfte, and the solvent is distilled off under reduced pressure. The residue is dissolved in methanol (30 ml) and thereto are added acetic acid (4 ml) and zinc dust (1.3 g), and the mixtue is stirred at room temperature overnight. After methanol is distilled off under reduced pressure, the residue is mixed with water (30 ml) and extracted with ethyl acetate. The extract is washed with water, dried over anhydrous magnesium sulfate, and ethyl acetate is distilled off under reduced pressure. The residue is purified by a medium pressure column chromatography using silica gel (eluant, chloroform). The fractions containing the desired compound are collected, and chloroform is distilled off under reduced pressure to give the title compound (0.6 g) as a caramelar substance. IR (KBr; cm$^{-1}$): 1715, 1680

Elementary analysis for $C_{30}H_{34}N_2O_5S \cdot 0.5H_2O$: Calcd. (%): C,66.28; H,6.49; N,5.15; S,5.90 Found (%): C,66.14; H,6.37; N,5.03; S,5.93

EXAMPLE 140

Preparation of 4 aminomethylbenzyl 3-[(2-mercaptomethyl-3-phenylpropionyl)amino]benzoate hydrochloride In the same manner as described in Example 122, there is prepared the title compound. m.p.: 85°-90° C. (amorphous) IR (KBr; cm$^{-1}$): 1715, 1650

Elementary analysis for $C_{25}H_{26}N_2O_3S \cdot HCl \cdot CH_3COOH$ Calcd. (%): C,61.06; H,5.88; Cl,6.68; N,5.28; S,6.04 Found (%): C,61.32; H,5.88; Cl,6.26; N,5.44; S,6.28

EXAMPLE 141

Preparation of 2-[3-[(2-mercaptomethyl-3-phenylpropionyl)amino]-benzoyl]-1, 3-dihexadecanoylpropane-1,2,3-triol:

In the same manner as described in Example 139, there is prepared the title compound. m.p.: 66°-68° C. (amorphous) IR (KBr; cm$^{-1}$): 1740, 1730, 1660

Elementary analysis for $C_{52}H_{83}NO_7S$: Calcd. (%): C,72.10; H,9.66; N,1.62; S,3.70 Found (%): C,72.16; H,9.59; N,1.56; S,3.72

EXAMPLE 142

Preparation of diethylaminocarbonylmethyl 3-[(2-mercaptomethyl-3-phenylpropionyl)amino]benzoate N,N'-[3,3'-dithiobis(2-benzylpropionyl)]bis(3-aminobenzoic acid) (compound of Example 109) (0.68 g) and potassium iodide (0.54 g) are dissolved in DMF (6 ml), and thereto are added triethylamine (0.22 g) and 2-chloro-N,N-diethylacetamide (0.49 g) with stirring at room temperature. After reacting overnight, the reaction mixture is mixed with water and extracted with ethyl acetate. The extract is washed with water and dried over anhydrous magnesium sulfate, and then ethyl acetate is distilled off under reduced pressure. The residue is dissolved in methanol (35 ml) and thereto are added water (one drop), acetic acid (2 ml) and zinc dust (0.77 g), and the mixture is stirred at room temperature overnight. After methanol is distilled off under reduced pressure, the mixture is mixed with water (30 ml) and extracted with ethyl acetate. The extract is washed with water, dried over anhydrous magnesium sulfate, and ethyl acetate is distilled off under reduced pressure. The residue is purified by a medium pressure column chromatography with CHP-20P (eluant, water-acetonitrile). The fractions containing the desired compound are collected and concentrated under reduced pressure, and the precipitates are separated by filtration to give the title compound (0.47 g). m.p.: 160°–163° C. (amorphous) IR (KBr; cm$^{-1}$): 1720, 1680, 1630

Elementary analysis for $C_{23}H_{28}N_2O_4S \cdot 0.25H_2O$: Calcd. (%): C,63.79; H,6.63; N,6.47; S,7.40 Found (%): C,64.05; H,6.59; N,6.62; S,7.16

EXAMPLE 143

Preparation of N [3 [(2 mercaptomethyl-3-phenylpropionyl)amino]benzoyl]glycine

In the same manner as described in Example 68-(a)-[2], there is prepared the title compound. m.p.: 80°–83° C. (amorphous) IR (KBr; cm$^{-1}$): 1720, 1650

Elementary analysis for $C_{19}H_{20}N_2O_4S \cdot 0.25H_2O$: Calcd. (%): C,60.54; H,5.48; N,7.43; S,8.51 Found (%): C,60.74; H,5.41; N,7.52; S,8.32

EXAMPLE 144

Preparation of N-[3-[(2-mercaptomethyl-3-phenylpropionyl)amino]benzoyl]-L-phenylalanine (a mixture of diastereomers)

In the same manner as described in Example 68-(a)-[2], there is prepared the title compound. m.p.: 83°–85° C. (amorphous) IR (KBr; cm$^{-1}$): 1720, 1640

Elementary analysis for $C_{26}H_{26}N_2O_4S \cdot 0.5H_2O$: Calcd. (%): C,66.22; H,5.77; N,5.94; S,6.80 Found (%): C,66.49; H,5.93; N,5.83; S,6.91

EXAMPLE 145

Preparation of 3-[(2-phenylacetylthiomethyl-3-phenylpropionyl)amino]-2-methylbenzoic acid 3-[(2-Mercaptomethyl-3-phenylpropionyl)amino]-2-methylbenzoic acid (compound of Example 7) (0.66 g) is dissolved in 1N aqueous sodium hydroxide solution, and the mixture is added dropwise to a solution of phenylacetyl chloride (0.31 g) in tetrahydrofuran (20 ml) under ice cooling. The mixture is adjusted to pH 7.6 with 1N aqueous sodium hydroxide solution and stirred at the same temperature for 30 minutes and further at room temperature for one hour, and then acidified with hydrochloric acid. Tetrahydrofuran is distilled off under reduced pressure, and the residue is extracted with ethyl acetate (80 ml). The extract is washed with saturated aqueous sodium chloride solution and dried over anhydrous sodium sulfate, and then ethyl acetate is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (0.54 g). m.p.: 135°–137° C. (amorphous) IR (KBr; cm$^{-1}$): 1680, 1640

Elementary analysis for $C_{26}H_{25}NO_4S$: Calcd. (%): C,69.78; H,5.63; N,3.13; S,7.16 Found (%): C,69.56; H,5.62; N,3.30; S,7.02

EXAMPLE 146

Preparation of 3-[[2-(1-naphthalenecarbonylthiomethyl-3-phenylpropionyl)amino]-2-methylbenzoic acid In the same manner as described in Example 145, there is prepared the title compound. m.p.: 139°–150° C. (amorphous) IR (KBr; cm$^{-1}$): 1680, 1670, 1650

Elementary analysis for $C_{29}H_{25}NO_4S$: Calcd. (%): C,72.03; H,5.21; N,2.90; S,6.63 Found (%): C,71.65; H,5.18; N,2.94; S,6.34

EXAMPLE 147

Preparation of 3-[[2-(2-furancarbonylthiomethyl)-3-phenylpropionyl]amino]-2-methylbenzoic acid In the same manner as described in Example 145, there is prepared the title compound. m.p.: 113°–116° C. (amorphous) IR (KBr; cm$^{-1}$): 1680, 1650, 1640

Elementary analysis for $C_{23}H_{21}NO_5S$: Calcd. (%): C,65.23; H,5.00; N,3.31; S,7.57 Found (%): C,64.99; H,4.93; N,3.44; S,7.78

EXAMPLE 148

Preparation of 3-[(2-decanoylthiomethyl-2-phenylpropionyl)amino]-2-methylbenzoic acid In the same manner as described in Example 145, there is prepared the title compound. m.p.: 105°–111° C. (amorphous) IR (KBr; cm$^{-1}$): 1690, 1740

Elementary analysis for $C_{28}H_{37}NO_4S$: Calcd. (%): C,69.53; H,7.71; N,2.90; S,6.63 Found (%): C,69.54; H,7.63; N,2.99; S,6.64

EXAMPLE 149

Preparation of 3-[(2 phenoxyacetylthiomethyl-3-phenylpropionyl)amino]-2-methylbenzoic acid In the same manner as described in Example 145, there is prepared the title compound. m.p.: 130°–132° C. (amorphous) IR (KBr; cm$^{-1}$): 1680, 1645

Elementary analysis for $C_{26}H_{25}NO_5S$: Calcd. (%): C,67.37; H,5.44; N,3.02; S,6.92 Found (%): C,67.30; H,5.28; N,3.11; S,7.03

EXAMPLE 150

Preparation of 3-[[2-(2-thienylacetylthiomethyl)-3-phenylpropionyl]amino]-2-methylbenzoic acid In the same manner as described in Example 145, there is prepared the title compound. m.p.: 134°–137° C. (amorphous) IR (KBr; cm$^{-1}$): 1685, 1645

Elementary analysis for $C_{24}H_{23}NO_4S_2$: Calcd. (%): C,63.55; H,5.11; N,3.09; S,14.14 Found (%) C,63.63; H,4.93; N,3.17; S,13.94

EXAMPLE 151

Preparation of 3-[[2-(3-pyridinecarbonylthiomethyl)-3-phenylpropionyl]amino]-2-methylbenzoic acid In the same manner as described in Example 145, there is prepared the title compound. m.p.: 80°–86° C. (amorphous) IR (KBr; cm$^{-1}$): 1660, 1650

Elementary analysis for $C_{24}H_{22}N_2O_4S \cdot 0.75H_2O \cdot 0.25$ dioxane: Calcd. (%): C,63.88; H,5.47; N,5.96; S,6.82 Found (%): C,63.94; H,5.24; N,6.07; S,6.58

EXAMPLE 152

Preparation of 3-[(2-butyrylthiomethyl-3-phenyl-propionyl)amino]-2-methylbenzoic acid In the same manner as described in Example 145, there is prepared the title compound. m p.: 136°–141° C. (amorphous) IR (KBr; cm$^{-1}$): 1685, 1655, 1650

Elementary analysis for $C_{22}H_{25}NO_4S$: Calcd. (%): C,66.14; H,6.31; N,3.51; S,8.03 Found (%): C,66.15; H,6.23; N,3.64; S,7.76

EXAMPLE 153

Preparation of 3-[(2-isobutyrylthiomethyl-3-phenyl-propionyl)amino]-2-methylbenzoic acid In the same manner as described in Example 145, there is prepared the title compound. m.p.: 178°–183° C. (amorphous) IR (KBr; cm$^{-1}$): 1680, 1650

Elementary analysis for $C_{22}H_{25}NO_4S$: Calcd. (%): C,66.14; H,6.31; N,3.51; S,8.03 Found (%): C,66.22; H,6.19; N,3.61; S,7.86

EXAMPLE 154

Preparation of 3-[(2-valerylthiomethyl-3-phenylpropionyl)amino]-2-methylbenzoic acid In the same manner as described in Example 145, there is prepared the title compound. m.p.: 113°–114° C. (amorphous) IR (KBr; cm$^{-1}$): 1690, 1645

Elementary analysis for $C_{23}H_{27}NO_4S$: Calcd. (%): C,66.80; H,6.58; N,3.39; S,7.75 Found (%): C,66.90; H,6.45; N,3.52; S,7.98

EXAMPLE 155

Preparation of 3-[(2-isovalerylthiomethyl-3-phenylpropionyl)amino]-2-methylbenzoic acid In the same manner as described in Example 145, there is prepared the title compound. m.p.: 118°–120° C. (amorphous) IR (KBr; cm$^{-1}$): 1690, 1650

Elementary analysis for $C_{23}H_{27}NO_4S$: Calcd. (%): C,66.80; H,6.58; N,3.39; S,7.75 Found (%): C,66.80; H,6.53; N,3.50; S,7.74

EXAMPLE 156

Preparation of 3-[[2-(2-thiophenecarbonylthiomethyl)-3-phenylpropionyl]amino]-2-methylbenzoic acid In the same manner as described in Example 145, there is prepared the title compound. m.p.: 164°–167° C. (amorphous) IR (KBr; cm$^{-1}$): 1690, 1650, 1630

Elementary analysis for $C_{23}H_{21}NO_4S_2$: Calcd. (%): C,62.85; H,4.82; N,3.19; S,14.59 Found (%): C,62.93; H,4.88; N,3.25; S,14.45

EXAMPLE 157

Preparation of 3-[(2-pivaloylthiomethyl-3 phenylpropionyl)amino]-2-methylbenzoic acid In the same manner as described in Example 145, there is prepared the title compound. m p.: 117°–120° C. (amorphous) IR (KBr; cm$^{-1}$): 1680, 1650

Elementary analysis for $C_{23}H_{27}NO_4S$: Calcd. (%): C,66.80; H,6.58; N,3.39; S,7.75 Found (%): C,66.91; H,6.56; N,3.48; S,7.95

EXAMPLE 158

Preparation of 3-[(2-benzoylthiomethyl-3 phenylpropionyl)amino]2 methylbenzoic acid In the same manner as described in Example 3, there is prepared the title compound. m.p.: 204°–205° C. (amorphous) IR (KBr; cm$^{-1}$): 1685, 1665, 1650

Elementary analysis for $C_{25}H_{23}NO_4S$: Calcd. (%): C,69.26; H,5.35; N,3.23; S,7.40 Found (%): C,69.05; H,5.20; N,3.08; S,7.40

EXAMPLE 159

Preparation of 3 [(2-dimethylaminocarbonylthiomethyl-3-phenylpropionyl)amino]-2-methylbenzoic acid 3-[(2-Mercaptomethyl-3-phenylpropionyl)amino-2-methylbenzoic acid (compound of Example 7) (0.66 g) is dissolved in pyridine (2 ml), and thereto is added dimethylaminocarbonyl chloride (0.26 g) with stirring under ice cooling, and the mixture is stirred under ice cooling for 2 hours and further at room temperature for 2 hours. To the reaction mixture is added ethyl acetate (50 ml) and the mixture is washed with saturated aqueous citric acid solution and water, dried over anhydrous magnesium sulfate, and ethyl acetate is distilled off under reduced pressure. The residue is purified by a medium pressure column chromatography with CHP-20P (eluant, water-acetonitrile). The fractions containing the desired compound are collected and concentrated under reduced pressure, and the precipitates are separated by filtration to give the title compound (0.23 g). m.p.: 84°–87° C. (amorphous) IR (KBr; cm$^{-1}$): 1710, 1690, 1650

Elementary analysis for $C_{21}H_{24}N_2O_4S$: Calcd. (%): C,62.98; H,6.04; N,6.99; S,8.01 Found (%): C,62.91; H,6.15; N,7.05; S,7.79

EXAMPLE 160

Preparation of 3-[(2-dimethylaminocarbonylthiomethyl-3-phenylpropionyl)amino]-2-methylbenzoic N, N-dimethylcarbamic anhydride In Example 159, when the product is purified by a medium pressure column chromatography, fractions different from those of the desired compound of Example 159 are collected, concentrated under reduced pressure, and extracted with ethyl acetate. The extract is dried over anhydrous magnesium sulfate, and the solvent is distilled off under reduced pressure to give the title compound (0.38 g) as an oily substance. IR (film; cm$^{-1}$): 1760, 1720, 1655

Elementary analysis for $C_{24}H_{29}N_3O_5S$: Calcd. (%): C,61.13; H,6.20; N,8.91; S,6.80 Found (%): C,61.01; H,6.26; N,8.75; S,6.79

EXAMPLE 161

Preparation of 3-[(2-propionylthiomethyl-3-phenylpropionyl)amino]-2-methylbenzoic acid In the same manner as described in Example 159, there is prepared the title compound. m.p. 163°–165° C. (amorphous) IR (KBr; cm$^{-1}$): 1690, 1650

Elementary analysis for $C_{21}H_{23}NO_4S$: Calcd. (%): C,65.43; H,6.01; N,3.63; S,8.32 Found (%): C,65.35; H,5.85; N,3.78; S,8.43

EXAMPLE 162

Preparation of 3-[(2-cyclohexanecarbonylthiomethyl-3-phenylpropionyl)amino]-2-methylbenzoic acid In the same manner as described in Example 159, there is prepared the title compound. m.p.: 117°–120° C. (amorphous) IR (KBr; cm$^{-1}$): 1685, 1645

Elementary analysis for $C_{25}H_{29}NO_4S$: Calcd. (%): C,68.31; H,6.65; N,3.19; S,7.29 Found (%): C,68.07; H,6.45; N,3.35; S,7.34

EXAMPLE 163

Preparation of 3-[(2-isobutyloxycarbonylthiomethyl-3-phenylpropionyl)amino]-2-methylbenzoic acid 3-[(2-Mercaptomethyl-3-phenylpropionyl)amino]-2-methylbenzoic acid (compound of Example 7) (0.66 g) is dissolved in a mixture of saturated aqueous sodium hydrogen carbonate solution and tetrahydrofuran (1 ml), and to the mixture is added a solution of isobutyl chloroformate (0.33 g) in tetrahydrofuran (5 ml) with stirring under ice cooling, and the mixture is stirred under ice cooling for 30 minutes and further at room temperature for one hour. The reaction mixture is acidified with 4N hydrochloric acid and extracted with ethyl acetate. The extract is washed with water and dried over anhydrous magnesium sulfate, and the solvent is distilled off under reduced pressure. The residue is purified by a medium pressure column chromatography with CHP-20P (eluant, water-acetonitrile). The fractions containing the desired compound are collected and concentrated under reduced pressure, and the precipitates are separated by filtration to give the title compound (0.31 g). m.p.: 165°–167° C. (amorphous) IR (KBr; cm$^{-1}$): 1700, 1650

Elementary analysis for $C_{23}H_{27}NO_5S$: Calcd. (%): C,64.31; H,6.34; N,3.26; S,7.46 Found (%): C,64.43; H,6.27; N,3.48; S,7.36

EXAMPLE 164

Preparation of 3-[(2-isobutyloxycarbonylthiomethyl-3-phenylpropionyl)amino]-2-methylbenzoic monoisobutyl carbonic anhydride In Example 163, when the product is purified by a medium pressure column chromatography, fractions different from those of the desired compound of Example 163 are collected and concentrated under reduced pressure to give the title compound (0.23 g) as an oily substance.

IR (film; cm$^{-1}$): 1800, 1740, 1710, 1650

Elementary analysis for $C_{28}H_{35}NO_7S$: Calcd. (%): C,63.50; H,6.66; N,2.64; S,6.05 Found (%): C,63.75; H,6.44; N,2.61; S,5.90

EXAMPLE 165

Preparation of 3-[[2-[N-(t-butyloxycarbonyl)glycylthiomethyl]-3-phenylpropionyl]amino]benzoic acid 3-[(2-Mercaptomethyl-3-phenylpropionyl)amino]benzoic acid (compound of Example 68-(a)-[2]) (0.5 g) and N-(t-butyloxycarbonyl)glycine N-hydroxysuccinimide ester (0.51 g) are dissolved in acetonitrile (40 ml) and thereto is added triethylamine (0.5 ml), and the mixture is stirred at room temperature for 40 minutes. Acetonitrile is distilled off under reduced pressure, and the residue is extracted with ethyl acetate (50 ml). The extract is washed with 10% aqueous citric acid solution and saturated aqueous sodium chloride solution, and then ethyl acetate is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (0.54 g). m.p.: 76°–80° C. (amorphous) IR (KBr; cm$^{-1}$): 1690

Elementary analysis for $C_{24}H_{28}N_2O_6S \cdot 0.5H_2O$: Calcd. (%): C,59.86; H,6.07; N,5.82; S,6.66 Found (%): C,60.21; H,6.31; N,5.75; S,6.16

EXAMPLE 166

Preparation of 3-[(2-glycylthiomethyl-3-phenylpropionyl)amino]benzoic acid

3-[[2-[N-(t-butyloxycarbonyl)glycylthiomethyl]-3-phenylpropionyl]amino]benzoic acid (compound of Example 165) (0.43 g) is dissolved in trifluoroacetic acid (3 ml), and the mixture is stirrred at room temperature for 30 minutes and adjusted to pH 4.0 with aqueous sodium hydrogen carbonate solution, and then is purified by a medium pressure column chromatography with CHP-20P (eluant, water-acetonitrile). The fractions containing the desired compound are collected and concentrated under reduced pressure, and thereto is added dioxane, and the solution is lyophilized to give the title compound (0.22 g). m.p.: 91°–96° C. (amorphous) IR (KBr; cm$^{-1}$): 1690, 1660

Elementary analysis for $C_{19}H_{20}N_2O_4S \cdot 0.5H_2O \cdot 0.5$dioxane: Calcd. (%): C,59.28; H,5.92; N,6.58; S,7.54 Found (%): C,59.52; H,5.78; N,6.74; S,7.12

EXAMPLE 167

Preparation of 3-[[2-N-cyclohexanecarbonyl-D-alanylthiomethyl-3-phenylpropionyl)amino]-2-methylbenzoic acid (a mixture of diastereomers)

N-Cyclohexanecarbonyl-D-alanine (0.3 g) is dissolved in tetrahydrofuran (5 ml) and thereto is added carbonyldiimidazole (0.3 g) with stirring under cooling with ice-ethanol and the mixture is stirred at the same temperature for one hour. To the mixture is added 3-[(2-mercaptomethyl-3-phenylpropionyl)amino]-2-methylbenzoic acid (compound of Example 7) (0.5 g), and the mixture is stirred for 30 minutes and further at room temperature for 5 hours. After the reaction, the reaction mixture is concentrated under reduced pressure, and thereto is added water (30 ml). The mixture is adjusted to pH 3 with saturated aqueous citric acid solution and extracted with ethyl acetate. The extract is washed with water and dried over anhydrous magnesium sulfate, and the solvent is distilled off under reduced pressure. The residue is purified by a medium pressure column chromatography with CHP-20P (eluant, water-acetonitrile). The fractions containing the desired compound are collected and concentrated under reduced pressure. The precipitates are separated by filtration to give the title compound (0.49 g). m.p.: 175°–180° C. (amorphous) IR (KBr; cm$^{-1}$): 1685, 1650

Elementary analysis for $C_{28}H_{34}N_2O_5S$: Calcd. (%): C,65.86; H,6.71; N,5.49; S,6.28 Found (%): C,65.57; H,6.75; N,5.51; S,6.01

EXAMPLE 168

Preparation of 4-[(2-acetylthiomethyl-3-phenylpropionyl)amino]-2-chlorobenzoic acid In the same manner as described in Example 27, there is prepared the title compound. m.p.: 145°–148° C. (amorphous) IR (KBr; cm$^{-1}$): 1690, 1660

Elementary analysis for $C_{19}H_{18}ClNO_4S$: Calcd. (%): C,58.24; H,4.63; Cl,9.05; N,3.57; S,8.18 Found (%): C,58.50; H,4.77; Cl,8.86; N,3.59; S,8.20

EXAMPLE 169

Preparation of 5-[(2-acetylthiomethyl-3-phenylpropionyl)amino]-2-hydroxybenzoic acid In the same manner as described in Example 27, there is prepared the title compound. m.p.: 185°–188° C. (amorphous) IR (KBr; cm$^{-1}$): 1690, 1670, 1655

Elementary analysis for $C_{19}H_{19}NO_5S$: Calcd. (%): C,61.11; H,5.13; N,3.75; S,8.59 Found (%) C,61.07; H,5.16; N,3.75; S,8.66

EXAMPLE 170

Preparation of 3-[(2-acetylthiomethyl-3-phenylpropionyl)amino]-2,5-dimethylbenzoic acid In the same manner as described in Example 64, there is prepared the title compound. m.p. 182°–186° C. (recrystallized from aqueous methanol) IR (KBr; cm$^{-1}$): 1690, 1650

Elementary analysis for $C_{21}H_{23}NO_4S$: Calcd. (%): C,65.43; H,6.01; N,3.63; S,8.32 Found (%): C,65.22; H,5.85; N,3.57; S,8.38

EXAMPLE 171

Preparation of 4-[(2-acetylthiomethyl-3-phenylpropionyl)amino]-2-hydroxybenzoic acid In the same manner as described in Example 27, there is prepared the title compound. m.p.: 141°–142° C. (amorphous) IR (KBr; cm$^{-1}$): 1680, 1650

Elementary analysis for $C_{19}H_{19}NO_5S$: Calcd. (%) C,61.11; H,5.13; N,3.75; S,8.59 Found (%) C,61.00; H,5.07; N,3.73; S,8.34

EXAMPLE 172

Preparation of 3-[(2-acetylthiomethyl-3-phenylpropionyl)amino]-2-naphthalenecarboxylic acid In the same manner as described in Example 27, there is prepared the title compound. m.p.: 138°–141° C. (amorphous)
IR (KBr; cm$^{-1}$): 1680, 1670

Elementary analysis for $C_{23}H_{21}NO_4S$: Calcd. (%): C,67.79; H,5.19; N,3.44; S,7.87 Found (%) C,67.80; H,5.24; N,3.34; S,7.72

EXAMPLE 173

Preparation of 3-[(2-acetylthiomethyl-3-phenylpropionyl)amino]-5-trifluoromethylbenzoic acid In the same manner as described in Example 64, there is prepared the title compound. m.p.: 62°–67° C. (amorphous) IR (KBr; cm$^{-1}$): 1700, 1660

Elementary analysis for $C_{20}H_{18}F_3NO_4S$: Calcd. (%): C,56.47; H,4.26; F,13.40; N,3.29; S,7.54 Found (%): C,56.25; H,4.21; F,13.27; N,3.22; S,7.99

EXAMPLE 174

Preparation of 3-[(2-acetylthiomethyl-4-methylpentanoyl)amino]benzoic acid

In the same manner as described in Example 27, there is prepared the title compound. m.p.: 184°–186° C. (colorless needles) (recrystallized from 70% aqueous acetonitrile)
cm-1): 1690, 1660 IR (KBr; cm$^{-1}$): 1690, 1660

Elementary analysis for $C_{16}H_{21}NO_4S$: Calcd. (%): C,59.42; H,6.55; N,4.33; S,9.91 Found (%): C,59.52; H,6.43; N,4.34; S,9.66

EXAMPLE 175

Preparation of 3-[(2-acetylthiomethyl-4-methylpentanoyl)amino]-2-methylbenzoic acid In the same manner as described in Example 27, there is prepared the title compound. m.p.: 154°–156° C. (amorphous) IR (KBr; cm$^{-1}$): 1690, 1650

Elementary analysis for $C_{17}H_{23}NO_4S$: Calcd. (%): C,60.51; H,6.87; N,4.15; S,9.50 Found (%): C,60.72; H,6.85; N,4.16; S,9.70

EXAMPLE 176

Preparation of 3-[(2-acetylthiomethyl-4-methylpentanoyl)amino]-5-methylbenzoic acid In the same manner as described in Example 27, there is prepared the title compound. m.p. 185°–187° C. (colorless short needles) (recrystallized from 80% aqueous acetonitrile) IR (KBr; cm$^{-1}$) 1700, 1680, 1650

Elementary analysis for $C_{17}H_{23}NO_4S$: Calcd. (%): C,60.51; H,6.87; N,4.15; S,9.50 Found (%): C,60.63; H,6.88; N,4.15; S,9.73

EXAMPLE 177

Preparation of 3-[(2-acetylthiomethyl-3-phenylpropionyl)amino]-2,6-dimethylbenzoic acid:

In the same manner as described in Example 64, there is prepared the title compound. m.p.: 187°–189° C. (amorphous) IR (KBr; cm$^{-1}$): 1680, 1630

Elementary analysis for $C_{21}H_{24}NO_4S$: Calcd. (%): C,65.43; H,6.01; N,3.63; S,8.32 Found (%): C,65.31; H,5.92; N,3.62; S,8.16

EXAMPLE 178

Preparation of 3-[[2-acetylthiomethyl-3-(4-methylphenyl)propionyl]amino]-2-methylbenzoic acid In the same manner as described in Example 27, there is prepared the title compound. m.p.: 206°–208° C. (colorless short needles) (recrystallized from 90% aqueous acetonitrile) IR (KBr; cm$^-$): 1680, 1650

Elementary analysis for $C_{21}H_{23}NO_4S$: Calcd. (%): C,65.43; H,6.01; N,3.63; S,8.31 Found (%): C,65.58; H,5.91; N,3.53; S,8.40

EXAMPLE 179

Preparation of 3-[(2-acetylthiomethyl-3-phenylpropionyl)amino]-4-(1-pyrrolidinylmethyl)benzoic acid (1) 4-Bromomethyl-3-nitrobenzoic acid (10 g) is dissolved in dichloromethane (100 ml) and thereto is added dropwise pyrrolidine (8 g) with stirring under ice cooling, and the mixture is stirred at room temperature for 30 minutes. Dichloromethane is distilled off under reduced pressure, and the residue is dissolved in conc. hydrochloric acid (40 ml) and thereto is added water (10 ml) with stirring under ice cooling and further is added tin (5.4 g), and the mixture is stirred under ice cooling for 1.5 hour. The reaction mixture is neutralized with 10N aqueous sodium hydroxide solution, and the catalyst is filtered off and the filtrate is concentrated. The residue is dissolved in water and purified by a medium pressure column chromatography with CHP-20P (eluant, water-acetonitrile). The fractions containing the desired compound are collected, and concentrated into dryness under reduced pressure to give 3-amino-4-(1-pyrrolidinylmethyl)benzoic acid (7.2 g).

(2) The compound prepared in the above (1) (2.8 g) is dissolved in a 60% aqueous solution of tetrahydrofuran (25 ml) containing sodium hydrogen carbonate (1.1 g), and to the mixture is added dropwise a solution of 2-acetylthiomethyl-3-phenylpropionyl chloride (2.1 g) in tetrahydrofuran (10 ml) with stirring under ice cooling, and the mixture is stirred at room temperature for one hour. Tetrahydrofuran is distilled off under reduced pressure, and the residue is dissolved in a mixture of water and acetonitrile and purified by a medium pressure column chromatography with CHP-20P (eluant, water-acetonitrile). The fractions containing the desired compound are collected and concentrated into dryness under reduced pressure to give the title compound (0.25 g). m.p.: 95°–98° C. (amorphous) IR (KBr; cm$^{-1}$): 1690

Elementary analysis for $C_{24}H_{28}N_2O_4S.0.75H_2O$: Calcd. (%) C,63.48; H,6.55; N,6.17; S,7.06 Found (%) C,63.58; H,6.33; N,6.21; S,7.08

EXAMPLE 180

Preparation of 4-[(2-mercaptomethyl-3-phenylpropionyl)amino]-2-chlorobenzoic acid In the same manner as described in Example 2, there is prepared the title compound. m.p.: 65°–70° C. (amorphous) IR (KBr; cm$^{-1}$): 1690

Elementary analysis for $C_{17}H_{16}ClNO_3S.0.4H_2O.0.4$dioxane: Calcd. (%): C,56.95; H,5.14; Cl,9.04; N,3.57; S,8.17 Found (%): C,57.10; H,4.84; Cl,9.10; N,3.81; S,7.92

EXAMPLE 181

Preparation of 5-[(2-mercaptomethyl-3-phenylpropionyl)amino]-2-hydroxybenzoic acid In the same manner as described in Example 2, there is prepared the title compound. m.p.: 206°–209° C. (amorphous) IR (KBr; cm$^{-1}$): 1650, 1620

Elementary analysis for $C_{17}H_{17}NO_4S$: Calcd. (%): C,61.62; H,5.17; N,4.23; S,9.68 Found (%): C,61.69; H,5.25; N,4.17; S,9.67

EXAMPLE 182

Preparation of 3-[(2-mercaptomethyl-3-phenylpropionyl)amino]-2,5-dimethylbenzoic acid In the same manner as described in Example 65, there is prepared the title compound. m.p.: 180°–182° C. (recrystallized from aqueous acetonitrile) IR (KBr; cm$^{-1}$): 1690, 1650

Elementary analysis for $C_{19}H_{21}NO_3S$: Calcd. (%): C,66.45; H,6.16; N,4.08; S,9.34 Found (%): C,66.52; H,6.08; N,4.06; S,9.21

EXAMPLE 183

Preparation of 4-[(2-mercaptomethyl-3-phenylpropionyl)amino]-2-hydroxybenzoic acid:

In the same manner as described in Example 2, there is prepared the title compound. m.p 166°–170° C. (amorphous) IR (KBr; cm$^{-1}$): 1650

Elementary analysis for $C_{17}H_{17}NO_4S$: Calcd. (%): C,61.62; H,5.17; N,4.23; S,9.68 Found (%): C,61.70; H,5.14; N,4.08; S,9.32

EXAMPLE 184

Preparation of 3-[(2-mercaptomethyl-3-phenylpropionyl)amino]-2-naphthalenecarboxylic acid In the same manner as described in Example 2, there is prepared the title compound. m.p.: 180°–182° C. (amorphous) IR (KBr; cm-1): 1680, 1660, 1650

Elementary analysis for $C_{21}H_{19}NO_3S$: Calcd. (%): C,69.02; H,5.24; N,3.83; S,8.77 Found (%): C,68.95; H,5.20; N,3.82; S,8.68

EXAMPLE 185

Preparation of 3-[(2-mercaptomethyl-3-phenylpropionyl)amino]-5-trifluoromethylbenzoic acid In the same manner as described in Example 65, there is prepared the title compound. m.p.: 71°–74° C. (amorphous) IR (KBr; cm$^{-1}$): 1700, 1660

Elementary analysis for $C_{18}H_{16}F_3NO_3S$: Calcd. (%) C,56.39; H,4.21; F,14.87; N,3.65; S,8.36 Found (%) C,56.16; H,4.18; F,15.03; N,3.68; S,8.86

EXAMPLE 186

Preparation of 3-[(2-mercaptomethyl-4-methylpentanoyl)amino]benzoic acid

In the same manner as described in Example 2, there is prepared the title compound. m.p.: >200° C. (amorphous) IR (KBr; cm$^{-1}$): 1700, 1680, 1650

Elementary analysis for $C_{14}H_{19}NO_3S$: Calcd. (%) C,59.76; H,6.81; N,4.98; S,11.40 Found (%): C,60.04; H,6.67; N,5.03; S,11.16

EXAMPLE 187

Preparation of 3-[(2-mercaptomethyl-4-methylpentanoyl)amino]-2-methylbenzoic acid 3-[(2-Acetylthiomethyl-4-methylpentanoyl)amino]-2-methylbenzoic acid (compound of Example 175) (3 g), 70% aqueous methanol (30 ml) and pyrrolidine (2.2 g) are mixed, and the mixture is stirred at room temperature for 30 minutes. The reaction mixture is adjusted to pH 3.0 with 10% hydrochloric acid, and methanol is distilled off under reduced pressure. The precipitated crystals are separated by filtration and dissolved in 50% aqueous acetonitrile and purified by a column chromatography using Diaion HP-20 (eluant, water-acetonitrile). The fractions containing the desired compound are collected and acetonitrile is distilled off under reduced pressure, and the precipitated crystals are separated by filtration to give the title compound (2 g). m.p.: 166°–168° C. (colorless needles) IR (KBr; cm$^{-1}$): 1690, 1660

Elementary analysis for $C_{15}H_{21}NO_3S$: Calcd. (%): C,60.99; H,7.17; N,4.74; S,10.85 Found (%): C,60.80; H,7.17; N,4.73; S,10.91

EXAMPLE 188

Preparation of 3-[(2-mercaptomethyl-4-methylpentanoyl)amino]-5-methylbenzoic acid In the same manner as described in Example 187, there is prepared the title compound. m.p.: 193°–195° C. (amorphous) IR (KBr; cm$^{-1}$): 1690, 1650

Elementary analysis for $C_{15}H_{21}NO_3S$: Calcd. (%): C,60.99; H,7.17; N,4.74; S,10.85 Found (%): C,61.16; H,7.15; N,4.81; S,10.72

EXAMPLE 189

Preparation of solid solution of 3-[(2-mercaptomethyl-4-methylpentanoyl)amino]-5-methylbenzoic acid with glycine In the same manner as described in Example 87, there is prepared the title compound. m.p.: 187°–189° C. (amorphous) IR (KBr; cm$^{-1}$): 1710 (weak), 1680, 1650

Elementary analysis for $C_{15}H_{21}NO_3S \cdot C_2H_5NO_2 \cdot 0.75H_2O$: Calcd. (%): C,53.18; H,7.22; N,7.30; S,8.35 Found (%): C,53.65; H,6.98; N,7.67; S,7.92

EXAMPLE 190

Preparation of 3-[(2-mercaptomethyl-3-phenylpropionyl)amino]-2,6-dimethylbenzoic acid In the same manner as described in Example 65, there is prepared the title compound. m.p.: 180°–181° C. (amorphous) IR (KBr; cm$^{-1}$): 1680, 1640

Elementary analysis for $C_{19}H_{21}NO_3S$: Calcd. (%): C,66.45; H,6.16; N,4.08; S,9.34 Found (%): C,66.47; H,5.89; N,4.20; S,9.07

EXAMPLE 191

Preparation of 3-[[2-mercaptomethyl-3-(4-methylphenyl)propionyl]amino]-2-methylbenzoic acid In the same manner as described in Example 187, there is prepared the title compound. m.p.: 194°–196° C. (amorphous) IR (KBr; cm$^{-1}$): 1690, 1650

Elementary analysis for $C_{19}H_{21}NO_3S$: Calcd. (%): C,66.45; H,6.16; N,4.08; S,9.34 Found (%): C,66.42; H,6.19; N,4.15; S,9.22

EXAMPLE 192

Preparation of N,N'-[3,3'-dithiobis(2-benzylpropionyl)]bis[3-amino-4-(1-pyrrolidinylmethyl) benzoic acid (a mixture of diastereomers)

3-[(2-Acetylthiomethyl-3-phenylpropionyl)amino]-4-(1-pyrrolidinylmethyl)benzoic acid (compound of Example 179) (0.2 g) is dissolved in 1N aqueous sodium hydroxide solution (1 ml), and the mixture is stirred at room temperature for 30 minutes. The reaction mixture is neutralized with 10% hydrochloric acid and purified by a medium pressure column chromatography with CHP-20P (eluant, water-acetonitrile). The fractions containing the desired compound are collected and concentrated into dryness to give the title compound (0.1 g). m.p.: 113°–116° C. (amorphous) IR (KBr; cm$^{-1}$): 1680, 1600

Elementary analysis for $C_{44}H_{50}N_4O_6S_2 \cdot 0.75H_2O$: Calcd. (%): C,65.36; H,6.42; N,6.93; S,7.93 Found (%): C,65.08; H,6.46; N,6.76; S,8.13

EXAMPLE 193

Preparation of N,N'-[3,3'-dithiobis(2-benzylpropionyl)]bis(3-amino-4-dimethylaminomethylbenzoic acid) (a mixture of diastereomers)

In the same manner as described in Example 192, there is prepared the title compound. m.p.: 115°–118° C. (amorphous) IR (KBr; cm$^{-1}$): 1680, 1600

Elementary analysis for $C_{40}H_{46}N_4O_6S_2 \cdot 0.5H_2O$: Calcd. (%): C,63.89; H,6.30; N,7.45; S,8.53 Found (%): C,63.86; H,6.43; N,7.49; S,8.28

EXAMPLE 194

Preparation of 3-[(3-mercapto-2-benzylbutanoyl)-amino]benzoic acid (a mixture of diastereomers)

(1) Methyl 2-acetyl-3-phenylpropionate (60 g) is dissolved in methanol (300 ml), and thereto is added portionwise sodium boro hydride (2.9 g) with stirring under ice cooling, and the mixture is stirred under ice cooling from 2 hours. The reaction mixture is adjusted to pH 1 with 10% hydrochloric acid, and methanol is distilled off under reduced pressure. The residue is extracted with ethyl acetate. The extract is washed with diluted aqueous sodium hydrogen carbonate solution and saturated aqueous sodium chloride solution, dried over anhydrous sodium sulfate, and ethyl acetate is distilled off under reduced pressure to give methyl 2-(1-hydroxyethyl)-3-phenylpropionate (60.4 g). IR (film; cm$^{-1}$): 3400 (broad), 1730

(2) The compound prepared in the above (1) (60 g) is dissolved in dioxane (240 ml) and thereto is added 6N aqueous sodium hydroxide solution (62 ml) with stirring under ice cooling, and the mixture is stirred at room temperature for one hour. The reaction mixture is adjusted to pH 1 with 10% hydrochloric acid, and dioxane is distilled off under reduced pressure, and the residue is extracted with ethyl acetate. The extract is washed with diluted aqueous sodium hydrogen carbonate solution and saturated aqueous sodium chloride solution, dried over anhydrous sodium sulfate, and ethyl acetate is distilled off under reduced pressure to give 2-(1-hydroxyethyl)-3-phenylpropionic acid (54.3 g). IR (KBr; cm$^{-1}$): 1700

(3) The compound prepared in the above (2) (5 g) and ethyl 3-aminobenzoate (4.3 g) are suspended in dichloromethane (25 ml), and thereto is added EDC.HCl (4.9 g). The mixture is stirred at room temperature for one hour. The reaction mixture is diluted with dichloromethane and washed with 10% hydrochloric acid, diluted aqueous sodium hydrogen carbonate solution and saturated aqueous sodium chloride solution in this order, dried over anhydrous sodium sulfate, and dichloromethane is distilled off under reduced pressure. The residue is dissolved in dichloromethane (25 ml) and thereto is added triethylamine (3.5 g) and further added dropwise methanesulfonyl chloride (3.9 g) with stirring under ice cooling, and the mixture is stirred at room temperature for one hour. The reaction mixture is diluted with dichloromethane and washed with 10% hydrochloric acid, diluted aqueous sodium hydrogen carbonate solution and saturated aqueous sodium chloride solution in this order, dried over anhydrous sodium sulfate, and dichloromethane is distilled off under reduced pressure. The residue is dissolved in ethanol (100 ml) and thereto is added potassium thioacetate (3.2 g), and the mixture is refluxed for 48 hours. Ethanol is distilled off under reduced pressure, and the residue is extracted with ethyl acetate. The extract is washed with 10% hydrochloric acid, diluted aqueous sodium hydrogen carbonate solution and saturated aqueous sodium chloride solution in this order, and ethyl acetate is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give ethyl 3-[(3-acetylthio-2-benzylbutanoyl)amino]benzoate (1.4 g). IR (film; cm$^{-1}$): 1720, 1690, 1660

(4) The compound prepared in the above (3) (0.9 g) is dissolved in dioxane (9 ml), and thereto is added 1N aqueous sodium hydroxide solution (7.3 ml) with stirring under ice cooling, and the mixture is stirred at room temperature for one hour under nitrogen. The mixture is adjusted to pH 1 with 10% hydrochloric acid. Dioxane is distilled off under reduced pressure, and the residue is extracted with ethyl acetate. The extract is washed with saturated aqueous sodium chloride solution and dried over anhydrous sodium sulfate, and then ethyl acetate is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (0.4 g). m.p.: 192°-196° C. (amorphous) IR (KBr; cm$^{-1}$): 1690, 1650, 1590

Elementary analysis for $C_{18}H_{19}NO_3S$: Calcd. (%): C,65.63; H,5.81; N,4.25; S,9.73 Found (%): C,65.42; H,5.75; N,4.30; S,9.68

EXAMPLE 195

Preparation of 3-[(3-acetylthio-2-benzylbutanoyl)amino]benzoic acid (a mixture of diastereomers)

3-[(3-Mercapto-2-benzylbutanoyl)amino]benzoic acid (compound of Example 194) (1.7 g) is suspended in dichloromethane (17 ml), and thereto is added triethylamine (0.52 g) with stirring under ice cooling. To the mixture are further added dropwise acetyl chloride (0.51 g) and triethylamine (0.52 g) simultaneously, and the mixture is stirred at room temperature for one hour. The reaction mixture is diluted with dichloromethane and washed with 10% hydrochloric acid and saturated aqueous sodium chloride solution and dried over anhydrous sodium sulfate, and then dichloromethane is distilled off under reduced pressure. The residue is dissolved in acetonitrile and purified by a medium pressure column chromatography with CHP-20P (eluant, water-acetonitrile). The fractions containing the desired compound are collected and concentrated into dryness under reduced pressure to give the title compound (0.6 g). m.p.: 180°-182° C. (amorphous) IR (KBr; cm$^{-1}$): 1680, 1650

Elementary analysis for $C_{20}H_{21}NO_4S$: Calcd. (%): C,64.67; H,5.70; N,3.77; S,8.63 Found (%): C,64.37; H,5.68; N,3.80; S,8.75

EXAMPLE 196

Preparation of 3-[(2-propionylthiomethyl-3-phenylpropionyl)amino]-5-methylbenzoic acid In the same manner as described in Example 145, there is prepared the title compound. m.p.: 151°-153° C. (amorphous) IR (KBr; cm$^{-1}$): 1690, 1660

Elementary analysis for $C_{21}H_{23}NO_4S$: Calcd. (%): C,65.43; H,6.01; N,3.63; S,8.32 Found (%): C,65.46; H,5.92; N,3.55; S,8.45

EXAMPLE 197

Preparation of 3-[(2-propionylthiomethyl-3-phenylpropionyl)amino]-5-methylbenzoic acid sodium salt In the same manner as described in Example 42, there is prepared the title compound. m.p.: 130°-133° C. (amorphous) IR (KBr; cm$^{-1}$): 1680, 1660

Elementary analysis for $C_{21}H_{22}NO_4SNa$ $0.25H_2O$: Calcd. (%): C,61.23; H,5.51; N,3.40; S,7.78; Na,5.58 Found (%): C,61.39; H,5.45; N,3.39; S,7.52; Na,5.73

EXAMPLE 198

Preparation of 3-[(2-n-butyrylthiomethyl-3-phenylpropionyl)amino]-5-methylbenzoic acid In the same manner as described in Example 145, there is prepared the title compound. m.p.: 134°–137° C. (amorphous) IR (KBr; cm$^{-1}$): 1690, 1655

Elementary analysis for $C_{22}H_{25}NO_4S$: Calcd. (%): C,66.14; H,6.31; N,3.51; S,8.03 Found (%): C,66.14; H,6.16; N,3.48; S,8.12

EXAMPLE 199

Preparation of 3-[(2-valerylthiomethyl-3-phenylpropionyl)amino]-5-methylbenzoic acid In the same manner as described in Example 145, there is prepared the title compound. m.p.: 151°–153° C. (amorphous) IR (KBr; cm$^1$): 1690, 1660

Elementary analysis for $C_{23}H_{27}NO_4S$: Calcd. (%): C,66.80; H,6.58; N,3.39; S,7.75 Found (%): C,66.71; H,6.53; N,3.38; S,7.54

EXAMPLE 200

Preparation of 3-[(2-isovalerylthiomethyl-3-phenylpropionyl)amino]-5-methylbenzoic acid In the same manner as described in Example 145, there is prepared the title compound. m.p.: 153°–157° C. (amorphous) IR (KBr; cm$^{-1}$): 1690, 1660

Elementary analysis for $C_{23}H_{27}NO_4S$: Calcd. (%) C,66.80; H,6.58; N,3.39; S,7.75 Found (%): C,66.64; H,6.59; N,3.37; S,7.62

What is claimed is:

1. An N-substituted mercaptopropanamide derivative of the formula:

$$R_4-CO-S-CH_2-CH-CONH-X-R_3$$
$$\phantom{R_4-CO-S-CH_2-}|$$
$$\phantom{R_4-CO-S-CH_2-}CH_2$$
$$\phantom{R_4-CO-S-CH_2-}|$$
$$\phantom{R_4-CO-S-CH_2-}Ph$$

wherein $R_4$ is a $C_1$–$C_4$ alkyl group, and —X—$R_3$ is

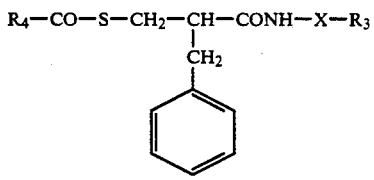

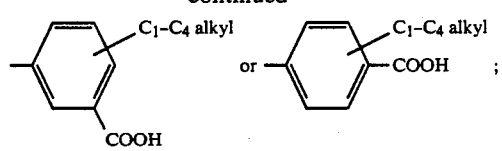

or a pharmaceutically acceptable salt thereof.

2. The compound according to claim 1, wherein —X—$R_3$ is

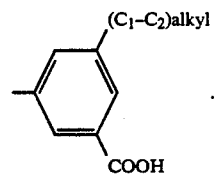

3. The compound according to claim 1, wherein $R_1$ is ($C_1$–$C_2$)alkyl-CO-S.

4. The compound according to claim 1, wherein $R_1$ is propionylthio.

5. The compound according to claim 1, wherein $R_1$ is acetyl thio.

6. The compound according to any one of claims 1, 3, 4 or 5, which is 3-[(2-propionyolthiomethyl-3-phenylpropionyl) amino]-5-methylbenzoic acid.

7. The compound according to any one of claims 1, 3, 4 or 6, which is 3-[(2-acethylthiomethyl-3-phenylpropionyl) amino]-5-methylbenzoic acid.

8. The compound according to any one of claims 1, 3 or 5, which is 3-[(2-acetylthiomethyl-3-phenylpropionyl)amino]-2-methylbenzoic acid.

9. The compound according to any one of claims 1, 3, 4 or 6 which is 3-[(2-acetylthiomethyl-3-phenylpropionyl) amino]-5-ethylbenzoic acid.

10. A pharmaceutical composition for the treatment of mild to moderate pain, which comprises an effective amount of the compound as set forth in claim 1 in admixture with a pharmaceutically acceptable carrier or diluent.

11. The composition according to claim 10, which comprises an effective amount of 3-[(2-propionylthiomethyl-3-phenylpropionyl) amino]-5-methylbenzoic acid in admixture with a pharmaceutically acceptable carrier or diluent.

12. A method for the treatment of mild to moderate pain, which comprises administering an effective amount of the compound as set forth in claim 1 to patients suffering from the pain.

13. The method according to claim 12, which comprises administering an effective amount of 3-[(2-propionylthiomethyl-3-phenylpropionyl) amino]-5-methylbenzoic acid to patients suffering from the pain.

* * * * *